(12) United States Patent
Yanofsky et al.

(10) Patent No.: US 7,273,968 B2
(45) Date of Patent: Sep. 25, 2007

(54) COMBINATIONS OF GENES FOR PRODUCING SEED PLANTS EXHIBITING MODULATED REPRODUCTIVE DEVELOPMENT

(75) Inventors: Martin F. Yanofsky, San Diego, CA (US); Soraya Pelaz, Madrid (ES); Gary Ditta, Poway, CA (US)

(73) Assignee: The Regents of the University of California, Oakland, CA (US)

( * ) Notice: Subject to any disclaimer, the term of this patent is extended or adjusted under 35 U.S.C. 154(b) by 328 days.

(21) Appl. No.: 10/794,923

(22) Filed: Mar. 4, 2004

(65) Prior Publication Data

US 2004/0229366 A1     Nov. 18, 2004

Related U.S. Application Data

(63) Continuation of application No. 09/853,450, filed on May 9, 2001, now Pat. No. 6,828,478.

(51) Int. Cl.
*C12N 15/82* (2006.01)
*A01H 5/00* (2006.01)

(52) U.S. Cl. .................. 800/298; 800/290; 800/287; 800/278

(58) Field of Classification Search ................ 800/298, 800/290, 287, 278
See application file for complete search history.

(56) References Cited

U.S. PATENT DOCUMENTS

| 5,844,119 A | 12/1998 | Weigel |
| 6,127,123 A | 10/2000 | Yanofsky |
| 6,828,478 B2 | 12/2004 | Yanofsky et al. |

FOREIGN PATENT DOCUMENTS

WO    WO97/46079 A1    12/1997

OTHER PUBLICATIONS

Tzeng et al (2003, Plant Physiology 133:1091-1101).*
Bowie et al, Science 247:1306-1310, 1990.*
McConnell et al, Nature 411 (6838):709-713, 2001.*
Davies, B. "Alteration of Tobacco Floral Organ Identity by Expression of Combinations of Antirrhinum MADS-box Genes" *The Plant Journal.* 1996, vol. 10, No. 4, pp. 663-677, entire document.
Honma, T., et al., Complexes of MADS-box Proteins are Sufficient to Convert Leaves into Floral Organs. *Nature.* Jan. 25, 2001. vol. 409, pp. 525-529, entire document.

Benfey, Philip N. et al.; "The CaMV 35S enhancer contains at least two domains which can confer different developmental and tissue-specific expression patterns"; 1989, *The EMBO Journal*, vol. 8, No. 8, pp. 2195-2202.
Benfey, Philip N. et al.; The Cauliflower Mosaic Virus 35S Promoter: Combinational Regulation of Transcription in Plants; 1990, *Science*, vol. 250, pp. 959-966.
Bowie, James U. et al.; "Deciphering the Message in Protein Sequences: Tolerance to Amino Acid Substitutions"; 1990, *Science*, vol. 247, pp. 1306-1310.
Hao, Dongyun et al.; "Unique Mode of GCC Box Recognition by the DNA-binding Domain of Ethylene-responsive Element-binding Factor (ERF Domain) in Plant"; 1998, *The Journal of Biological Chemistry*, vol. 273, No. 41, pp. 26857-26861.
Honma, Takashi et al.; "Complexes of MADS-box proteins are sufficient to convert leaves into floral organs"; 2001, *Nature*, vol. 409, pp. 525-529.
Izawa, Takeshi et al.; "Plant bZIP Protein DNA Binding Specificity"; 1993, *J. Mol. Biol.*, vol. 230, pp. 1131-1144.
Kagaya, Yasuaki et al.; "The promoter from the rice nuclear gene encoding chloroplast aldolase confers mesophyll-specific and light-regulated expression in transgenic tobacco"; 1995, *Mol. Gen. Genet*, vol. 248, pp. 668-674.
Krizek, Beth Allyn et al.; "Mapping the protein regions responsible for the functional specificities of the *Arabidopsis* MADS domain"; 1996, *Proceedings of the National Academy of Science*, vol. 93, pp. 4063-4070.
Liljegren, Sarah J. et al.; "Interactions among *Apetala1, Leafy*, and *Terminal Flower1* Specify Meristem Fate"; 1999, *Plant Cell*, vol. 11, No. 6, pp. 1007-1018.
McConnell, Jane R. et al.; "Role of *Phabulosa* and *Phavoluta* in determining radial patterning in shoots"; 2001, *Nature*, vol. 411, pp. 709-713.
Moonan, Francis et al.; "Analysis of Genotypic Diversity amoung North, South, and Central American Isolates of *Sugarcane Yellow Leaf Virus*: Evidence for Colombian Origins and for Intraspecific Spatial Phylogenetic Variation"; 2002, *Journal of Virology*, vol. 76, No. 3, pp. 1339-1348.
Pelaz, Soraya et al.; "B and C floral organ identity functions require *SEPALLATA* MADS-box genes"; 2000, *Nature*, vol. 405, pp. 2000-2003.
Pelaz, Soraya et al.; "*Apetala1* and *Sepallata3* interact to promote flower development"; 2001, *The Plant Journal*, vol. 26, No. 4, pp. 385-394.
Pelaz, Soraya et al.; "Conversion of leaves into petals in *Arabidopsis*"; 2001, *Current Biology*, vol. 11, No. 3, pp. 182-184.

* cited by examiner

*Primary Examiner*—Stuart F. Baum
(74) *Attorney, Agent, or Firm*—Townsend and Townsend and Crew LLP

(57) ABSTRACT

The present invention provides plants that exhibit modulated reproductive development and methods of modulating the timing of reproductive development in plants.

16 Claims, No Drawings

COMBINATIONS OF GENES FOR PRODUCING SEED PLANTS EXHIBITING MODULATED REPRODUCTIVE DEVELOPMENT

STATEMENT AS TO RIGHTS TO INVENTIONS MADE UNDER FEDERALLY SPONSORED RESEARCH AND DEVELOPMENT

This work was supported by grant DCB-9018749 awarded by the National Science Foundation and by grant USDA 93-37304 awarded by the United States Department of Agriculture. The United States Government has certain rights in this invention.

BACKGROUND OF THE INVENTION

A flower is the reproductive structure of a flowering plant. Following fertilization, the ovary of the flower becomes a fruit and bears seeds. As a practical consequence, production of fruit and seed-derived crops such as grapes, beans, corn, wheat, rice and hops is dependent upon flowering.

Early in the life cycle of a flowering plant, vegetative growth occurs, and roots, stems and leaves are formed. During the later period of reproductive growth, flowers as well as new shoots or branches develop. However, the factors responsible for the transition from vegetative to reproductive growth, and the onset of flowering, are poorly understood.

A variety of external signals, such as length of daylight and temperature, affect the time of flowering. The time of flowering also is subject to genetic controls that prevent young plants from flowering prematurely. Thus, the pattern of genes expressed in a plant is an important determinant of the time of flowering.

Given these external signals and genetic controls, a relatively fixed period of vegetative growth precedes flowering in a particular plant species. The length of time required for a crop to mature to flowering limits the geographic location in which it can be grown and can be an important determinant of yield. In addition, since the time of flowering determines when a plant is reproductively mature, the pace of a plant breeding program also depends upon the length of time required for a plant to flower.

Traditionally, plant breeding involves generating hybrids of existing plants, which are examined for improved yield or quality. The improvement of existing plant crops through plant breeding is central to increasing the amount of food grown in the world since the amount of land suitable for agriculture is limited. For example, the development of new strains of wheat, corn and rice through plant breeding has increased the yield of these crops grown in underdeveloped countries such as Mexico, India and Pakistan. Unfortunately, plant breeding is inherently a slow process since plants must be reproductively mature before selective breeding can proceed.

For some plant species, the length of time needed to mature to flowering is so long that selective breeding, which requires several rounds of backcrossing progeny plants with their parents, is impractical. For example, perennial trees such as walnut, hickory, oak, maple and cherry do not flower for several years after planting. As a result, breeding of such plant species for insect or disease-resistance or to produce improved wood or fruit, for example, would require decades, even if only a few rounds of selection were performed.

Methods of promoting early reproductive development can make breeding of long generation seed plants such as trees practical for the first time. Methods of promoting early reproductive development also would be useful for shortening growth periods, thereby broadening the geographic range in which a crop such as rice, corn or coffee can be grown. Unfortunately, methods for promoting early reproductive development in a seed plant have not yet been described. Thus, there is a need for methods that promote early reproductive development. The present invention satisfies this need and provides related advantages as well.

DEFINITIONS

As used herein, the term "transgenic" refers to a seed plant that contains in its genome an exogenous nucleic acid molecule, which can be derived from the same or a different plant species. The exogenous nucleic acid molecule can be a gene regulatory element such as a promoter, enhancer or other regulatory element or can contain a coding sequence, which can be linked to a heterologous gene regulatory element.

As used herein, the term "seed plant" means an angiosperm or a gymnosperm. The term "angiosperm," as used herein, means a seed-bearing plant whose seeds are borne in a mature ovary (fruit). An angiosperm commonly is recognized as a flowering plant. The term "gymnosperm," as used herein, means a seed-bearing plant with seeds not enclosed in an ovary.

Angiosperms are divided into two broad classes based on the number of cotyledons, which are seed leaves that generally store or absorb food. Thus, a monocotyledonous angiosperm is an angiosperm having a single cotyledon, and a dicotyledonous angiosperm is an angiosperm having two cotyledons. Angiosperms are well known and produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms encompass a variety of flowering plants, including, for example, cereal plants, leguminous plants, oilseed plants, hardwood trees, fruit-bearing plants and ornamental flowers, which general classes are not necessarily exclusive. Such angiosperms include for example, a cereal plant, which produces an edible grain cereal. Such cereal plants include, for example, corn, rice, wheat, barley, oat, rye, orchard grass, guinea grass, sorghum and turf grass. In addition, a leguminous plant is an angiosperm that is a member of the pea family (Fabaceae) and produces a characteristic fruit known as a legume. Examples of leguminous plants include, for example, soybean, pea, chickpea, moth bean, broad bean, kidney bean, lima bean, lentil, cowpea, dry bean, and peanut. Examples of legumes also include alfalfa, birdsfoot trefoil, clover and sainfoin. An oilseed plant also is an angiosperm with seeds that are useful as a source of oil. Examples of oilseed plants include soybean, sunflower, rapeseed and cottonseed.

An angiosperm also can be a hardwood tree, which is a perennial woody plant that generally has a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut and willow. Trees are useful, for example, as a source of pulp, paper, structural material and fuel.

An angiosperm also can be a fruit-bearing plant, which produces a mature, ripened ovary (usually containing seeds)

that is suitable for human or animal consumption. For example, hops are a member of the mulberry family prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, orchid, lily, tulip and chrysanthemum, snapdragon, camellia, carnation and petunia plants. The skilled artisan will recognize that the methods of the invention can be practiced using these or other angiosperms, as desired.

Gymnosperms encompass four divisions: cycads, ginkgo, conifers and gnetophytes. The conifers are the most widespread of living gymnosperms and frequently are cultivated for structural wood or for pulp or paper. Conifers include redwood trees, pines, firs, spruces, hemlocks, Douglas firs, cypresses, junipers and yews. The skilled artisan will recognize that the methods of the invention can be practiced with these and other gymnosperms.

As used herein, the term "non-naturally occurring seed plant" means a seed plant containing a genome that has been modified by man. A transgenic seed plant, for example, is a non-naturally occurring seed plant that contains an exogenous nucleic acid molecule and, therefore, has a genome that has been modified by man. Furthermore, a seed plant that contains, for example, a mutation in an endogenous floral meristem identity gene regulatory element as a result of calculated exposure to a mutagenic agent also contains a genome that has been modified by man. In contrast, a seed plant containing a spontaneous or naturally occurring mutation is not a "non-naturally occurring seed plant" and, therefore, is not encompassed within the invention.

"Reproductive development" refers to the production of floral organs, including but not limited to sepals, petal, stamens, carpels as well as polen, ovules and/or seed. "Reproductive development" initiates upon the development of the floral meristem, typically derived from a shoot meristem.

The term "recombinant nucleic acid molecule," as used herein, means a non-naturally occurring nucleic acid molecule that has been manipulated in vitro such that it is genetically distinguishable from a naturally occurring nucleic acid molecule. A recombinant nucleic acid molecule of the invention comprises two nucleic acid molecules that have been manipulated in vitro such that the two nucleic acid molecules are operably linked.

As used herein, the term "inducible regulatory element" means a nucleic acid molecule that confers conditional expression upon an operably linked nucleic acid molecule, where expression of the operably linked nucleic acid molecule is increased in the presence of a particular inducing agent as compared to expression of the nucleic acid molecule in the absence of the inducing agent. In a method of the invention, a useful inducible regulatory element has the following characteristics: confers low level expression upon an operably linked nucleic acid molecule in the absence of an inducing agent; confers high level expression upon an operably linked nucleic acid molecule in the presence of an appropriate inducing agent; and utilizes an inducing agent that does not interfere substantially with the normal physiology of a transgenic seed plant treated with the inducing agent. It is recognized, for example, that subsequent to introduction into a seed plant, a particularly useful inducible regulatory element is one that confers an extremely low level of expression upon an operably linked nucleic acid molecule in the absence of inducing agent. Such an inducible regulatory element is considered to be tightly regulated.

The term "operably linked," as used in reference to a regulatory element, such as a promoter or inducible regulatory element, and a nucleic acid molecule encoding a floral meristem identity gene product, means that the regulatory element confers regulated expression upon the operably linked nucleic acid molecule encoding the floral meristem identity gene product. Thus, the term operably linked, as used herein in reference to an inducible regulatory element and a nucleic acid molecule encoding a floral meristem identity gene product, means that the inducible regulatory element is linked to the nucleic acid molecule encoding a floral meristem identity gene product such that the inducible regulatory element increases expression of the floral meristem identity gene product in the presence of the appropriate inducing agent. It is recognized that two nucleic acid molecules that are operably linked contain, at a minimum, all elements essential for transcription, including, for example, a TATA box. One skilled in the art knows, for example, that an inducible regulatory element that lacks minimal promoter elements can be combined with a nucleic acid molecule having minimal promoter elements and a nucleic acid molecule encoding a floral meristem identity gene product such that expression of the floral meristem identity gene product can be increased in the presence of the appropriate inducing agent.

As used herein in reference to a nucleic acid molecule of the invention, the terms "sense" and "antisense" have their commonly understood meanings.

As used herein in reference to a nucleic acid molecule of the invention, the term "fragment" means a portion of the nucleic acid sequence containing at least about 50 base pairs to the full-length of the nucleic acid molecule. In contrast to an active fragment, as defined herein, a fragment of a nucleic acid molecule need not encode a functional portion of a gene product.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

The phrase "host cell" refers to a cell from any organism. Preferred host cells are derived from plants, bacteria, yeast, fungi, insects or other animals. Methods for introducing polynucleotide sequences into various types of host cells are well known in the art.

The "biological activity of a polypeptide" refers to any molecular activity or phenotype that is caused by the polypeptide. For example, the ability to transfer a phosphate to a substrate or the ability to bind a specific DNA sequence is a biological activity. One biological activity of of the gene products of the invention is the ability to modulate the time of development of reproductive structures in plants.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by reference to a specific nucleic acid sequence.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "nucleic acid encoding a gene product". In addition, the term specifically includes those sequences substantially identical (determined as described below) with an polynucleotide sequence disclosed here and that encode polypeptides that are either mutants of wild type polypeptides or retain the function of the polypeptide (e.g., resulting from conservative substitutions of amino acids in the polypeptides). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 95%, or 99%. compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Bid.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Nati. Acad. Sci. USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

BRIEF SUMMARY OF THE INVENTION

The present invention provides a non-naturally occurring seed plant, the plant comprising: (1) a first ectopically expressed polynucleotide encoding an APETALA1 gene product at least 50% identical to SEQ ID NO:2, SEQ ID NO:4, SEQ ID NO:6 or SEQ ID NO:8 or a CAULIFLOWER gene product at least 50% identical to SEQ ID NO:10 or SEQ ID NO:12; and (2) a second ectopically expressed nucleic acid molecule encoding a SEP1 gene product at least 50% identical to SEQ ID NO:28, a SEP2 gene product at least 50% identical to SEQ ID NO:30, a SEP3 gene product at least 50% identical to SEQ ID NO:32 or an AGL24 gene product at least 50% identical to SEQ ID NO:38. in some embodiments, the non-naturally occurring seed plant is characterized by early reproductive development. In some embodiments, expression of the first ectopically expressed polynucleotide is increased in a tissue of a plant compared to a wild type plant. In some embodiments, expression of the second ectopically expressed polynucleotide is increased in a tissue of a plant compared to a wild type plant. In some embodiments, expression of the first ectopically expressed polynucleotide is decreased in a tissue of a plant compared to a wild type plant. In some aspects, expression of the second ectopically expressed polynucleotide is decreased in a tissue of a plant compared to a wild type plant.

The invention provides for an endogenous first ectopically expressed polynucleotide comprising a modified gene regulatory element. Alternatively, the invention provides for an endogenous second ectopically expressed polynucleotide comprising a modified gene regulatory element. For example, the non-naturally occurring seed plant is a transgenic plant comprising a first exogenous gene regulatory element operably linked to the first ectopically expressible polynucleotide and a second exogenous gene regulatory element operably linked to the second ectopically expressible polynucleotide. In some aspects, the first polynucleotide is operably linked to the first exogenous gene regulatory element in a sense orientation. In some aspects, the first polynucleotide is operably linked to the first exogenous gene regulatory element in an antisense orientation. In some aspects, the second polynucleotide is operably linked to the second exogenous gene regulatory element in a sense orientation. In some aspects, the second polynucleotide is operably linked to the second exogenous gene regulatory element in an antisense orientation.

The invention also provides methods of modulating the timing of reproductive development in a plant, the methods comprising ectopically expressing a first polynucleotide encoding an APETALA1 gene product at least 50% identical to SEQ ID NO:2, SEQ ID NO:4, SEQ ID NO:6 or SEQ ID NO:8 or a CAULIFLOWER gene product at least 50% identical to SEQ ID NO:10 or SEQ ID NO:12; and ectopically expressing a second nucleic acid molecule encoding a SEP1 gene product at least 50% identical to SEQ ID NO:28, a SEP2 gene product at least 50% identical to SEQ ID NO:30, a SEP3 gene product at least 50% identical to SEQ ID NO:32 or an AGL24 gene product at least 50% identical to SEQ ID NO:38. For example, in one aspect, the invention provides for introducing a first ectopically expressed nucleic acid molecule comprising a first polynucleotide encoding an APETALA1 gene product at least 50% identical to SEQ ID NO:2, SEQ ID NO:4, SEQ ID NO:6 or SEQ ID NO:8 or a CAULIFLOWER gene product at least 50% identical to SEQ ID NO:10 or SEQ ID NO:12; and introducing a second ectopically expressed nucleic acid molecule comprising a second polynucleotide encoding a SEP1 gene product at least 50% identical to SEQ ID NO:28, a SEP2 gene product at least 50% identical to SEQ ID NO:30, a SEP3 gene product at least 50% identical to SEQ ID NO:32 or an AGL24 gene product at least 50% identical to SEQ ID NO:38.

DETAILED DESCRIPTION OF THE INVENTION

The present invention provides the surprising finding that ectopic expression of certain MADS-box-containing gene products, such as SEP1, SEP2, SEP3 or AGL24, combined with the ectopic expression of AP1, CAL or LFY gene products, result in modulated reproductive development. Thus, this invention provides plants comprising such ectopically expressible gene products as well as methods of modulating the timing of reproductive development in plants.

A flower, like a leaf or shoot, is derived from the shoot apical meristem, which is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, *Ann. Rev. Plant Physiol. Plant Mol. Biol.* 46:167-188 (1995), which is incorporated herein by reference).

Once induced, shoot apical meristem either persists and produces floral meristem, which gives rise to flowers, and lateral meristem, which gives rise to branches, or is itself converted to floral meristem. Floral meristem differentiates into a single flower having a fixed number of floral organs in a whorled arrangement. Dicots, for example, contain four whorls (concentric rings), in which sepals (first whorl) and petals (second whorl) surround stamens (third whorl) and carpels (fourth whorl).

Following the transition from vegetative to reproductive development in *Arabidopsis*, flower meristems arise on the flanks of the shoot apical (inflorescence) meristem and subsequently develop into flowers with four organ types (sepals, petals, stamens and carpels). Flower meristem identity is specified in part by the APETALA1 (AP1), CALIFLOWER (CAL) and LEAFY (LFY) genes. In ap1 mutants, the sepals are transformed to leaf-like organs and the petals fail to develop. In the axils of these leaf-like organs, secondary flowers arise which repeat the same pattern as the primary ones. Although cal single mutants appear wild type, ap1 cal double mutants display a massive proliferation of inflorescence-like meristems in positions that would normally be occupied by solitary flowers. The functional redundancy shared by AP1 and CAL can be explained in part by the fact that these two genes encode related members of the MADS box family of regulatory proteins (Bowman et al., *Development* 119, 721-743 (1993); Gustafson-Brown et al., *Cell* 76, 131-143 (1994); Kempin et al., *Science* 267, 522-525 (1995); Mandel et al., *Nature* 360, 273-277 (1992)).

Genetic studies led to the proposal of the ABC model that explains how the individual and combined activities of the ABC genes specify the four organ types of the typical eudicot flower. A alone specifies sepals, A and B specify petals, B and C specify stamens, and C alone specifies carpels. In *Arabidopsis*, the A-function genes are AP1 and APETALA2 (AP2), B-function genes are APETALA3 (AP3), PISTILLATA (PI), and the C-function gene is AGAMOUS (AG). In addition, recent studies have shown that a trio of closely related genes, SEPALLATA1/2/3 (SEP1/2/3), are required for petal, stamen and carpel identity, and are thus necessary for the activities of the B- and C-function genes (Pelaz et al., *Nature* 405, 200-203 (2000)). Remarkably, with the exception of the AP2 gene, all of the other organ identity genes belong to the extended family of MADS-box genes, a family that is known to include more than 44 distinct sequences in *Arabidopsis* (Alvarez-Buylla et al., *Proc. Natl. Acad. Sci. USA* 97, 5328-5333 (2000); Davies and Schwarz-Sommer, In *Plant Promoters and Transcription Factors (Results and Problems in Cell Differentiation* 20), (ed. L. Nover), pp. 235-258 (1994); Purugganan et al., *Genetics* 140, 345-356 (1995); Rounsley et al., *Plant Cell* 7, 1259-1269 (1995)).

MADS-domain proteins, well characterized in yeast (MCM1, Ammererer, *Genes Dev.* 4, 299-312 (1990)) and mammals (SRF, Norman et al., *Cell* 55, 989-1003 (1988)) form dimers that bind to DNA and form ternary complexes with many unrelated proteins (Lamb and McKnight, *Trends Biochem. Sci.* 16, 417-422 (1991); Shore and Sharrocks, *Eur. J. Chem.* 229, 1-13 (1995)). A number of studies have shown that heterodimers and ternary complexes of plant MADS-domain proteins can occur, and given the overlapping expression pattern of numerous MADS-box genes, such interactions greatly increase the regulatory complexity of MADS-box genes (Davies et al., *EMBO J.* 15, 4330-4343 (1996); Egea-Cortines et al., *EMBO J.* 18, 5370-5379 (1999); Fan et al., *Plant J.* 11, 999-1010 (1997)). The regulatory specificity of these genes is achieved through protein-protein interactions and not through different intrinsic DNA binding specificities (Krizek and Meyerowitz, *Proc. Natl. Acad. Sci. USA* 93, 4063-4070 (1996); Shore and Sharrocks, *Eur. J. Chem.* 229, 1-13 (1995)). MADS box proteins are composed of four different domains, designated M, I, K and C. The MADS (M) domain, is highly conserved among these proteins, and is responsible for the binding to DNA in addition to its participation in homodimer formation of some proteins. The I region also participates in homodimer formation (Krizek and Meyerowitz, supra; Riechmann et al., *Proc. Natl. Acad. Sci. USA* 93, 4793-4798 (1996)). Adjacent to the I region is the K-domain, so named, due to its similarity to the coiled-coil domain of keratin. It is absent in the non-plant proteins, and has been implicated in protein-protein interaction (Fan et al., supra; Krizek and Meyerowitz, supra; Mizukami et al., *Plant Cell* 8, 831-845 (1996); Moon et al., *Plant Physiol.* 120, 1193-1203 (1999); Riechmann et al., supra). The C-terminal region has been proposed to be involved in transcriptional activation (Huang et al., *Plant Mol. Biol.* 28, 549-567 (1995)), and also to play a role in the formation of ternary complexes (Egea-Cortines et al., *EMBO J.* 18, 5370-5379 (1999)).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

By convention herein, a wild-type gene sequence is represented in upper case italic letters (for example, APETALA1), and a wild-type gene product is represented in upper case non-italic letters (APETALA1). Further, a mutant gene allele is represented in lower case italic letters (ap1), and a mutant gene product is represented in lower case non-italic letters (ap1).

Genetic studies have identified a number of genes involved in regulating flower development. These genes can be classified into different groups depending on their function. Flowering time genes, for example, are involved in floral induction and regulate the transition from vegetative to reproductive growth. In comparison, the floral meristem identity genes, which are the subject matter of the present invention as disclosed herein, encode proteins that promote the conversion of shoot meristem to floral meristem in an angiosperm. In addition, floral organ identity genes encode proteins that determine whether sepals, petals, stamens or carpels are formed during floral development (Yanofsky, supra, 1995; Weigel, *Ann. Rev. Genetics* 29:19-39 (1995), which is incorporated herein by reference). Some of the floral meristem identity gene products also have a role in specifying floral organ identity.

Floral meristem identity genes have been identified by characterizing genetic mutations that prevent or alter floral meristem formation. Among floral meristem identity gene mutations in *Arabidopsis thaliana*, those in the gene LEAFY (LFY) generally have the strongest effect on floral meristem identity. Mutations in LFY completely transform the basalmost flowers into secondary shoots and have variable effects on later-arising (apical) flowers. In comparison, mutations in the floral meristem identity gene APETALA1 (AP1) result in replacement of a few basal flowers by inflorescence shoots that are not subtended by leaves. An apical flower produced in an ap1 mutant has an indeterminate structure, in which a flower arises within a flower. These mutant phenotypes indicate that both AP1 and LFY contribute to establishing the identity of the floral meristem although neither gene is absolutely required. The phenotype of lfy ap1 double mutants, in which structures with flower-like characteristics are very rare, indicates that LFY and AP1 encode partially redundant activities.

In addition to the LFY and AP1 genes, a third locus that greatly enhances the ap1 mutant phenotype has been identified in *Arabidopsis*. This locus, designated CAULIFLOWER (CAL), derives its name from the resulting "cauliflower" phenotype, which is strikingly similar to the common garden variety of cauliflower (Kempin et al., *Science* 267:522-525 (1995), which is incorporated herein by reference). In an ap1 cal double mutant, floral meristem behaves as shoot meristem in that there is a massive proliferation of meristems in the position that normally would be occupied by a single flower. However, an *Arabidopsis* mutant lacking only CAL, such as cal-1, has a normal phenotype, indicating that AP1 can substitute for the loss of CAL in these plants. In addition, because floral meristem that forms in an ap1 mutant behaves as shoot meristem in an ap1 cal double mutant, CAL can largely substitute for AP1 in specifying floral meristem. These genetic data indicate that CAL and AP1 encode activities that are partially redundant in converting shoot meristem to floral meristem.

Other genetic loci play at least minor roles in specifying floral meristem identity. For example, although a mutation in APETALA2 (AP2) alone does not result in altered inflorescence characteristics, ap2 ap1 double mutants have indeterminate flowers (flowers with shoot-like characteristics; Bowman et al., *Development* 119:721-743 (1993), which is incorporated herein by reference). Also, mutations in the CLAVATA1 (CLV1) gene result in an enlarged meristem and lead to a variety of phenotypes (Clark et al., *Development* 119:397-418 (1993)). In a cly1 ap1 double mutant, formation of flowers is initiated, but the center of each flower often develops as an indeterminate inflorescence. Thus, mutations in CLAVATA1 result in the loss of floral meristem identity in the center of wild-type flowers. Genetic evidence also indicates that the gene product of UNUSUAL FLORAL ORGANS (UFO) plays a role in determining the identity of floral meristem. Additional floral meristem identity genes associated with altered floral meristem formation remain to be isolated.

Mutations in another locus, designated TERMINAL FLOWER (TFL), produce phenotypes that generally are reversed as compared to mutations in the floral meristem identity genes. For example, tfl mutants flower early, and the indeterminate apical and lateral meristems develop as determinate floral meristems (Alvarez et al., *Plant J.* 2:103-116 (1992)). These characteristics indicate that the TFL promotes maintenance of shoot meristem. TFL also acts directly or indirectly to negatively regulate AP1 and LFY expression in shoot meristem since these AP1 and LFY are ectopically expressed in the shoot meristem of tfl mutants (Gustafson-Brown et al., *Cell* 76:131-143 (1994); Weigel et al., *Cell* 69:843-859 (1992)). It is recognized that a plant having a mutation in TFL can have a phenotype similar to a non-naturally occurring seed plant of the invention. Such tfl mutants, however, which have a mutation in an endogenous TERMINAL FLOWER gene, are explicitly excluded from the scope of the present invention.

The results of such genetic studies indicate that several floral meristem identity gene products, including AP1, CAL and LFY, act redundantly to convert shoot meristem to floral meristem in an angiosperm. As disclosed herein, ectopic expression of a single floral meristem identity gene product such as AP1, CAL or LFY is sufficient to convert shoot meristem to floral meristem in an angiosperm. Thus, the present invention provides a non-naturally occurring seed plant such as an angiosperm or gymnosperm that contains a first or second ectopically expressible nucleic acid molecule encoding a first floral meristem identity gene product, provided that such ectopic expression is not due to a mutation in an endogenous TERMINAL FLOWER gene.

As disclosed herein, an ectopically expressible nucleic acid molecule encoding a floral meristem identity gene product can be, for example, a transgene encoding a floral meristem identity gene product under control of a heterologous gene regulatory element. In addition, such an ectopically expressible nucleic acid molecule can be an endogenous floral meristem identity gene coding sequence that is placed under control of a heterologous gene regulatory element. The ectopically expressible nucleic acid molecule also can be, for example, an endogenous floral meristem identity gene having a modified gene regulatory element such that the endogenous floral meristem identity gene is no longer subject to negative regulation by TFL.

The term "ectopically expressible" is used herein to refer to a nucleic acid molecule encoding a floral meristem identity gene product that can be expressed in a tissue other than a tissue in which it normally is expressed or at a time other than the time at which it normally is expressed, provided that the floral meristem identity gene product is not expressed from its native, naturally occurring promoter. Ectopic expression of a floral meristem identity gene product is a result of the expression of the gene coding region from a heterologous promoter or from a modified variant of its own promoter, such that expression of the floral meristem identity gene product is no longer in the tissue in which it normally is expressed or at the time at which it normally is expressed. An exogenous nucleic acid molecule encoding an AP1 gene product under control of its native, wild type promoter, for example, does not constitute an ectopically expressible nucleic acid molecule encoding a floral meristem identity gene product. However, a nucleic acid molecule encoding an AP1 gene product under control of a constitutive promoter, which results in expression of AP1 in a tissue such as shoot meristem where it is not normally expressed, is an ectopically expressible nucleic acid molecule as defined herein.

Actual ectopic expression of a floral meristem identity gene is dependent on various factors and can be constitutive or inducible expression. For example, AP1, which normally is expressed in floral meristem, is ectopically expressible in the shoot meristem of an angiosperm. When a floral meristem identity gene product such as AP1, CAL or LFY is ectopically expressed in shoot meristem in an angiosperm, the shoot meristem is converted to floral meristem and early reproductive development can occur (see WO 97/46078, incorporated herein by reference).

An ectopically expressible nucleic acid molecule encoding a floral meristem identity gene product can be expressed prior to the time in development at which the corresponding endogenous gene normally is expressed. For example, an *Arabidopsis* plant grown under continuous light conditions expresses AP1 just prior to day 18, when normal reproductive development (flowering) begins. However, AP1 can be ectopically expressed in shoot meristem prior to day 18, resulting in early conversion of shoot meristem to floral meristem and early reproductive development. See WO 97/46078. As disclosed in Example ID of WO 97/46078, a transgenic *Arabidopsis* plant that ectopically expresses AP1 in shoot meristem under control of a constitutive promoter can flower at day 10, which is earlier than the time of reproductive development for a non-transgenic plant grown under the same conditions (day 18). It is recognized that in some transgenic seed plants containing, for example, an exogenous nucleic acid molecule encoding AP1 under control of a constitutive promoter, neither the exogenous nor endogenous AP1 will be expressed. Such transgenic plants in which AP1 gene expression is cosuppressed, although not characterized by early reproductive development, also can be valuable as disclosed below.

I. Floral Meristem Gene Products

As used herein, the term "floral meristem identity gene product" means a gene product that promotes conversion of shoot meristem to floral meristem in an angiosperm. Expression of a floral meristem identity gene product such as AP1, CAL or LFY in shoot meristem can convert shoot meristem to floral meristem in an angiosperm. Furthermore, ectopic expression of a floral meristem identity gene product also can promote early reproductive development.

A floral meristem identity gene product is distinguishable from a late flowering gene product or an early flowering gene product. The use of a late flowering gene product or an early flowering gene product is not encompassed within the scope of the present invention. In addition, reference is made herein to an "inactive" floral meristem identity gene product, as exemplified by the product of the *Brassica oleracea* var. *botrytis* CAL gene (BobCAL) (see below). Expression of an inactive floral meristem identity gene product in an angiosperm does not result in the conversion of shoot meristem to floral meristem in the angiosperm. An inactive floral meristem identity gene product such as BobCAL is excluded from the meaning of the term "floral meristem identity gene product" as defined herein.

A. AP1

A floral meristem identity gene product can be, for example, an AP1 gene product having the amino acid sequence of SEQ ID NO: 2, which is a 256 amino acid gene product encoded by the *Arabidopsis thaliana* AP1 cDNA. The *Arabidopsis* AP1 cDNA encodes a highly conserved MADS domain, which can function as a DNA-binding domain, and a K domain, which has structural similarity to the coiled-coil domain of keratins and can be involved in protein-protein interactions.

As used herein, the term "APETALA1," "AP1" or "AP1 gene product" means a floral meristem identity gene product that is characterized, in part, by having an amino acid sequence substantially identical to the amino acid sequence of SEQ ID NO: 2 in the region from amino acid 1 to amino acid 163 or with the amino acid sequence of SEQ ID NO: 8 in the region from amino acid 1 to amino acid 163. Alternatively, "AP1 gene product" refers to a gene product substantially identical to SEQ ID NO:2 or SEQ ID NO:8. Like other floral meristem identity gene products, AP1 promotes conversion of shoot meristem to floral meristem in an angiosperm. An AP1 gene product useful in the invention can be, for example, *Arabidopsis* AP1 having the amino acid sequence of SEQ ID NO: 2; *Brassica oleracea* AP1 having the amino acid sequence of SEQ ID NO: 4; *Brassica oleracea* var. *botrytis* AP1 having the amino acid sequence of SEQ ID NO: 6 or *Zea mays* AP1 having the amino acid sequence of SEQ ID NO: 8.

In wild-type *Arabidopsis*, AP1 RNA is expressed in flowers but is not detectable in roots, stems or leaves (Mandel et al., *Nature* 360:273-277 (1992), which is incorporated herein by reference). The earliest detectable expression of AP1 RNA is in young floral meristem at the time it initially forms on the flanks of shoot meristem. Expression of AP1 increases as the floral meristem increases in size; no AP1 expression is detectable in shoot meristem. In later stages of development, AP1 expression ceases in cells that will give rise to reproductive organs of a flower (stamens and carpels), but is maintained in cells that will give rise to non-reproductive organs (sepals and petals; Mandel, supra, 1992). Thus, in nature, AP1 expression is restricted to floral meristem and to certain regions of the flowers that develop from this meristemic tissue.

B. CAL

CAULIFLOWER (CAL) is another example of a floral meristem identity gene product. As used herein, the term "CAULIFLOWER," "CAL" or "CAL gene product" means a floral meristem identity gene product that is characterized, in part, by substantial identity to an amino acid sequence of SEQ ID NO: 10 in the region from amino acid 1 to amino acid 160 or with the amino acid sequence of SEQ ID NO: 12 in the region from amino acid 1 to amino acid 160. Alternatively, "CAL gene product" refers to a gene product substantially identical to SEQ ID NO:10 or SEQ ID NO:12.

A CAL gene product is exemplified by the *Arabidopsis* CAL gene product, which has the amino acid sequence of SEQ ID NO: 10, or the *Brassica oleracea* CAL gene product, which has the amino acid sequence of SEQ ID NO:12. As disclosed herein, CAL, like AP1, contains a MADS domain and a K domain. The MADS domains of CAL and AP1 differ in only five of 56 amino acid residues, where four of the five differences represent conservative amino acid replacements. Over the entire sequence, the *Arabidopsis* CAL and *Arabidopsis* AP1 sequences (SEQ ID NOS: 10 and 2) are 76% identical and are 88% similar if conservative amino acid substitutions are allowed.

Similar to the expression pattern of AP1, CAL RNA is expressed in young floral meristem in *Arabidopsis*. However, in contrast to AP1 expression, which is high throughout sepal and petal development, CAL expression is low in these organs. Thus, in nature, CAL is expressed in floral meristem and, to a lesser extent, in the organs of developed flowers.

The skilled artisan will recognize that, due to the high sequence conservation between AP1 and CAL, a novel ortholog can be categorized as both a CAL and an AP1, as defined herein. However, if desired, an AP1 ortholog can be distinguished from a CAL ortholog by demonstrating a greater similarity to *Arabidopsis* AP1 than to any other MADS box gene, such as CAL, as set forth in Purugganan et al. (*Genetics* 140:345-356 (1995), which is incorporated herein by reference). Furthermore, AP1 can be distinguished from CAL by its ability to complement, or restore a wild-type phenotype, when introduced into a strong ap1 mutant. For example, introduction of *Arabidopsis* AP1 (AGL7)

complements the phenotype of the strong ap1-1 mutant; however, introduction of CAL (AGL10) into a cal-1 ap1-1 mutant plant yields the ap1-1 single mutant phenotype, demonstrating that CAL cannot complement the ap1-1 mutation (see, for example, Mandel et al., supra, 1992; Kempin et al., supra, 1995). Thus, AP1 can be distinguished from CAL, if desired, by the ability of a nucleic acid molecule encoding AP1 to complement a strong ap1 mutant such as ap1-1 or ap1-15.

C. LFY

LEAFY (LFY) is yet another example of a floral meristem identity gene product. As used herein, the term "LEAFY" or "LFY" or "LFY gene product" means a floral meristem identity gene product that is characterized, in part, by having an amino acid sequence that has substantial identity with the amino acid sequence of SEQ ID NO:16. In nature, LFY is expressed in floral meristem as well as during vegetative development. As disclosed herein, ectopic expression in shoot meristem of a floral meristem identity gene product, which normally is expressed in floral meristem, can convert shoot meristem to floral meristem in an angiosperm. Under appropriate conditions, ectopic expression in shoot meristem of a floral meristem identity gene product such as AP1, CAL, LFY, or a combination thereof, can promote early reproductive development.

D. Floral Meristem Gene Product Orthologs

Flower development in *Arabidopsis* is recognized in the art as a model for flower development in angiosperms in general. Gene orthologs corresponding to the *Arabidopsis* genes involved in the early steps of flower formation have been identified in distantly related angiosperm species, and these gene orthologs show remarkably similar patterns of RNA expression. Mutations in gene orthologs also result in phenotypes that correspond to the phenotype produced by a similar mutation in *Arabidopsis*. For example, orthologs of the *Arabidopsis* floral meristem identity genes AP1 and LFY and the *Arabidopsis* organ identity genes AGAMOUS, APETALA3 and PISTILLATA have been isolated from monocots such as maize and, where characterized, reveal the anticipated RNA expression patterns and related mutant phenotypes (Schmidt et al., *Plant Cell* 5:729-737 (1993); and Veit et al., *Plant Cell* 5:1205-1215 (1993), each of which is incorporated herein by reference). Furthermore, a gene ortholog can be functionally interchangeable in that it can function across distantly related species boundaries (Mandel et al., *Cell* 71:133-143 (1992), which is incorporated herein by reference). Taken together, these data suggest that the underlying mechanisms controlling the initiation and proper development of flowers are conserved across distantly related dicot and monocot boundaries.

Floral meristem identity genes in particular are conserved among distantly related *angiosperm* and *gymnosperm* species. For example, a gene ortholog of *Arabidopsis* AP1 has been isolated from *Antirrhinum majus* (snapdragon; Huijser et al., *EMBO J.* 11:1239-1249 (1992), which is incorporated herein by reference). An ortholog of *Arabidopsis* AP1 also has been isolated from *Brassica oleracea* var. *botrytis* (cauliflower, see SEQ ID NO:6), *Zea Mays* (maize; see SEQ ID NO:8) and rice (OsMADS14 (*Plant Physiology* 120:1193-1203 (1999)). Furthermore, AP1 ortholgs also can be isolated from gymnosperms. Similarly, gene orthologs of *Arabidopsis* LFY have been isolated from angiosperms such as *Antirrhinum majus*, tobacco and poplar tree and from gymnosperms such as Douglas fir (Coen et al., *Cell*, 63:1311-1322 (1990); Kelly et al., *Plant Cell* 7:225-234 (1995); and Rottmann et al., *Cell Biochem. Suppl.* 17B: 23 (1993); Strauss et al., *Molec. Breed* 1:5-26 (1995), each of which is incorporated herein by reference). The conservation of floral meristem identity gene products in non-flowering plants such as coniferous trees indicates that floral meristem identity genes can promote the reproductive development of gymnosperms as well as angiosperms.

The characterization of ap1 and lfy mutants also indicates that floral meristem identity gene products such as AP1 and LFY function similarly in distantly related plant species. For example, a mutation in the *Antirrhinum* AP1 ortholog results in a phenotype similar to the *Arabidopsis* ap1 indeterminate flower within a flower phenotype (Huijser et al., supra, 1992). In addition, a mutation in the *Antirrhinum* LFY ortholog results in a phenotype similar to the *Arabidopsis* lfy mutant phenotype (Coen et al., supra, 1995)

A floral meristem identity gene product also can function across species boundaries. For example, introduction of a nucleic acid molecule encoding *Arabidopsis* LFY into a heterologous seed plant such as tobacco or aspen results in early reproductive development (Weigel and Nilsson, *Nature* 377:495-500 (1995), which is incorporated herein by reference). As disclosed herein, a nucleic acid molecule encoding an *Arabidopsis* API gene product (SEQ ID NO: 1) or an *Arabidopsis* CAL gene product (SEQ ID NO: 9) can be introduced into a heterologous seed plant such as corn, wheat, rice or pine and, upon ectopic expression, can promote early reproductive development in the transgenic seed plant. Furthermore, as disclosed herein, the conserved nature of the AP1, CAL and LFY coding sequences among diverse seed plant species allows a nucleic acid molecule encoding a floral meristem identity gene product isolated from essentially any seed plant to be introduced into essentially any other seed plant, wherein, upon appropriate expression of the introduced nucleic acid molecule in the seed plant, the floral meristem identity gene product promotes early reproductive development in the seed plant.

If desired, a novel AP1, CAL or LFY coding sequence can be isolated from a seed plant using a nucleotide sequence as a probe and methods well known in the art of molecular biology (Sambrook et al. (eds.), *Molecular Cloning: A Laboratory Manual* (Second Edition), Plainview, N.Y.: Cold Spring Harbor Laboratory Press (1989), which is incorporated herein by reference). As exemplified herein and discussed in detail below (see Example VA), an AP1 ortholog from *Zea Mays* (maize; SEQ ID NO: 7) was isolated using the *Arabidopsis* AP1 cDNA (SEQ ID NO: 1) as a probe.

II. AGAMOUS-Like Gene Products

Modulation of expression of the gene products described below, either alone, or in combination with the ectopic expression of AP1 or CAL, results in the modulation of the development of reproductive development in plants.

A. SEP1, SEP2 and SEP3

SEP1, SEP2 and SEP3 (previously known as AGL2, AGL4 and AGL9, respectively) are a class of floral organ identity gene products that are required for development of stamens and carpels (Pelaz, et al., *Nature* 405:200-203 (2000)). The SEP gene products are functionally redundant. Therefore, inactivation of only one SEP gene product does not typically result in the development of a mutant floral phenotype. Ectopic or increased expression of a SEP gene product results in early development of reproductive structures. Delay of reproductive development typically requires the reduction of expression of at least two and sometimes all three SEP gene products due to the redundancy of their function.

As used herein, the term "SEP1" or "SEP1 gene product" means a floral meristem identity gene product, or active fragment thereof, that is characterized, in part, by having an amino acid sequence substantially identical to SEQ ID NO: 28. The term "SEP2" or "SEP2 gene product" means a floral meristem identity gene product, or active fragment thereof, that is characterized, in part, by having an amino acid sequence substantially identical to SEQ ID NO: 30. SEP1 and SEP2 sequences were previously described in Ma et al., *Genes & Development* 5:484-495 (1991). An exemplary SEP1 nucleic acid sequence is displayed as SEQ ID NO:27. An exemplary SEP2 nucleic acid sequence is displayed as SEQ ID NO:29. The term "SEP3" or "SEP3 gene product" means a floral meristem identity gene product, or active fragment thereof, that is characterized, in part, by having an amino acid sequence substantially identical to SEQ ID NO: 32. SEP3 sequences were previously described in Mandel et al., *Sex. Plant Reprod.* 11:22-28 (1998). An exemplary SEP3 nucleic acid sequence is displayed as SEQ ID NO:31.

B. AGL20

As used herein, the term "AGL20" or "AGL20 gene product" means a gene product that is characterized, in part, by having an amino acid sequence substantially identical to SEQ ID NO: 34. AGL20 is also known as "SOC1." See, e.g., Samach et al. *Science* 288:1613-1616 (2000). Reduction of endogenous expression of AGL20 results in delayed development of reproductive structures in plants. An exemplary AGL20 nucleic acid sequence is displayed as SEQ ID NO:33.

C. AGL22

As used herein, the term "AGL22" or "AGL22 gene product" means a gene product that is characterized, in part, by having an amino acid sequence substantially identical to SEQ ID NO: 36. Decreased expression of an AGL22 gene product results in early development of reproductive structures. AGL22 is also known as "SVP." An exemplary AGL22 nucleic acid sequence is displayed as SEQ ID NO:35.

D. AGL24

As used herein, the term "AGL24" or "AGL24 gene product" means a gene product that is characterized, in part, by having an amino acid sequence substantially identical to SEQ ID NO: 38. An exemplary AGL24 nucleic acid sequence is displayed as SEQ ID NO:37. Ectopic or increased expression of AGL24 results in early development of reproductive structures in plants. Reduced expression of endogenous AGL24 results in delayed development of reproductive structures in plants.

E. AGL27

As used herein, the term "AGL27" or "AGL27 gene product" means a gene product that is characterized, in part, by having an amino acid sequence substantially identical to SEQ ID NOS:40 or 41. An exemplary AGL27 cDNA nucleic acid sequence is displayed as SEQ ID NO:39. An alternatively spliced AGL27 cDNA, and resulting translated product, are displayed as SEQ ID NO:49 and SEQ ID NO:50.

III. Effect of Gene Products of the Invention on Timing of Reproductive Development As described in U.S. Pat. No. 6,002,069, ectopic expression of the AP1 or CAL gene products results in the early development of reproductive structures in plants. The present invention demonstrates that ectopic expression of a number of other genes in combination with the ectopic expression of AP1 or CAL, leads to significantly earlier timing of reproductive development than plants ectopically expressing AP1 or CAL alone. In one embodiment, the invention provides a non-naturally occurring seed plant that contains a first ectopically expressible nucleic acid molecule encoding a floral meristem identity gene product, provided that the first nucleic acid molecule is not ectopically expressed due to a mutation in an endogenous TERMINAL FLOWER gene, and a second ectopically expressible nucleic acid molecule encoding SEP1, SEP2, SEP3 or AGL24, wherein the plant is characterized by modulated timing of reproductive development.

As used herein, the term "characterized by early reproductive development," when used in reference to a non-naturally occurring seed plant of the invention, means a non-naturally occurring seed plant that forms reproductive structures at an earlier stage than when reproductive structures form on a corresponding naturally occurring seed plant that is grown under the same conditions and that does not ectopically express a floral meristem identity gene product. In addition, "characterized by early reproductive development" also refers to the formation of reproduction structures at an earlier stage than a plant identical except for the lack of ectopic expression of the nucleic acids of the invention (e.g., polynucleotides substantially similar to nucleic acid molecules encoding SEQ ID NO:2, SEQ ID NO:4, SEQ ID NO:6, SEQ ID NO:8, SEQ ID NO:10, SEQ ID NO:12, SEQ ID NO:28, SEQ ID NO:30, SEQ ID NO:32, SEQ ID NO:34, SEQ ID NO:36, SEQ ID NO:38 or SEQ ID NOS:40 or 41). Note that "stage," as used above, refers to either the amount of time from germination of seed or the number of leaves that a plant produces prior to initiation of reproductive structures. Similarly, "characterized by late reproductive development" or "characterized by delayed reproductive development" refers to the delayed development of reproductive structures compared to a naturally-occurring seed plant or to a plant, natural or transgenic, that does not ectopically express a nucleic acid of the invention. The reproductive structure of an angiosperm, for example, is a flower, and the reproductive structure of a coniferous plant is a cone. For a particular naturally occurring seed plant, reproductive development occurs at a well-defined time that depends, in part, on genetic factors as well as on environmental conditions, such as day length and temperature. Thus, given a defined set of environmental condition and lacking ectopic expression of a floral meristem identity gene product, a naturally occurring seed plant will undergo reproductive development at a relatively fixed time.

It is recognized that various transgenic plants that are characterized by altered timing of reproductive development have been described previously. Such transgenic plants, as discussed herein, are distinguishable from a non-naturally occurring seed plant of the invention or are explicitly excluded from the present invention. The product of a "late-flowering gene" can promote early reproductive development. However, a late flowering gene product is not a floral meristem identity gene product since it does not specify the conversion of shoot meristem to floral meristem in an angiosperm. Therefore, a transgenic plant expressing a late-flowering gene product is distinguishable from a non-naturally occurring seed plant of the invention. For example, a transgenic plant expressing the late-flowering gene, CONSTANS (CO), flowers earlier than the corresponding wild type plant, but does not contain an ectopically expressible nucleic acid molecule encoding a floral meristem identity gene product (Putterill et al., *Cell* 80:847-857 (1995)). Thus, the early-flowering transgenic plant described by Putterill et al. is not a non-naturally occurring seed plant as defined herein.

Early reproductive development also has been observed in a transgenic tobacco plant expressing an exogenous rice MADS domain gene. Although the product of the rice MADS domain gene promotes early reproductive development, it does not specify the identity of floral meristem and, thus, cannot convert shoot meristem to floral meristem in an angiosperm (Chung et al., *Plant Mol. Biol.* 26:657-665 (1994)). Therefore, an early-flowering transgenic plant containing this rice MADS domain gene, like an early-flowering transgenic plant containing CONSTANS, is distinguishable from an early-flowering non-naturally occurring seed plant of the invention.

Mutations in a class of genes known as "early-flowering genes" also produce plants characterized by early reproductive development. Such early-flowering genes include, for example, EARLY FLOWERING 1-3 (ELF1, ELF2, ELF3); EMBRYONIC FLOWER 1,2 (EMF1, EMF2); LONG HYPOCOTYL 1,2 (HY1, HY2); PHYTOCHROME B (PHYB), SPINDLY (SPY) and TERMINAL FLOWER (TFL) (Weigel, supra, 1995). The wild type product of an early-flowering gene retards reproductive development and is distinguishable from a floral meristem identity gene product in that an early-flowering gene product does not promote conversion of shoot meristem to floral meristem in an angiosperm. A plant that flowers early due to the loss of an early-flowering gene product function is distinct from a non-naturally occurring seed plant of the invention characterized by early reproductive development since such a plant does not contain an ectopically expressible nucleic acid molecule encoding a floral meristem identity gene product.

An *Arabidopsis* plant having a mutation in the TERMINAL FLOWER (TFL) gene is characterized by early reproductive development and by the conversion of shoots to flowers (Alvarez et al., *Plant J.* 2:103-116 (1992), which is incorporated herein by reference). However, TFL is not a floral meristem identity gene product, as defined herein. Specifically, it is the loss of TFL that promotes conversion of shoot meristem to floral meristem. Since the function of TFL is to antagonize formation of floral meristem, a tfl mutant, which lacks functional TFL, converts shoot meristem to floral meristem prematurely. Although TFL is not a floral meristem identity gene product and does not itself convert shoot meristem to floral meristem, the loss of TFL can result in a plant with an ectopically expressed floral meristem identity gene product. However, such a tfl mutant, in which a mutation in an endogenous TERMINAL FLOWER gene results in conversion of shoot meristem to floral meristem, is excluded explicitly from the present invention.

In various embodiments, the present invention provides a non-naturally occurring seed plant containing a first ectopically expressible nucleic acid molecule encoding a first floral meristem identity gene product, provided that the first nucleic acid molecule is not ectopically expressed due to a mutation in an endogenous TERMINAL FLOWER gene. If desired, a non-naturally occurring seed plant of the invention can contain a second ectopically expressible nucleic acid molecule encoding SEP1, SE2, SEP3, AGL20, AGL22, AGL24, or AGL27, provided that the first or second nucleic acid molecule is not ectopically expressed due to a mutation in an endogenous TERMINAL FLOWER gene.

An ectopically expressible nucleic acid molecule encoding a floral meristem identity gene product can be expressed, as desired, either constitutively or inducibly. Such an ectopically expressible nucleic acid molecule encoding a floral meristem identity gene product can be an endogenous floral meristem identity gene that has, for example, a mutation in a gene regulatory element. An ectopically expressible nucleic acid molecule encoding a floral meristem identity gene product also can be an endogenous nucleic acid molecule encoding a floral meristem identity gene product that is linked to an exogenous, heterologous gene regulatory element that confers ectopic expression. In addition, an ectopically expressible nucleic acid molecule encoding a floral meristem identity gene product can be an exogenous nucleic acid molecule that encodes a floral meristem identity gene product under control of a heterologous gene regulatory element.

A non-naturally occurring seed plant of the invention can contain an endogenous floral meristem identity gene having a modified gene regulatory element. The term "modified gene regulatory element," as used herein in reference to the regulatory element of a floral meristem identity gene, means a regulatory element having a mutation that results in ectopic expression of the linked endogenous floral meristem identity gene. Such a gene regulatory element can be, for example, a promoter or enhancer element and can be positioned 5' or 3' to the coding sequence or within an intronic sequence of the floral meristem identity gene. A modified gene regulatory element can have, for example, a nucleotide insertion, deletion or substitution that is produced, for example, by chemical mutagenesis using a mutagen such as ethylmethane sulfonate or by insertional mutagenesis using a transposable element. A modified gene regulatory element can be a functionally inactivated binding site for TFL or a functionally inactivated binding site for a gene product regulated by TFL, such that modification of the gene regulatory element results in ectopic expression of the linked floral meristem identity gene product, for example, in the shoot meristem of an angiosperm.

The present invention also provides a transgenic seed plant containing a first exogenous gene promoter that regulates a first ectopically expressible nucleic acid molecule encoding a first floral meristem identity gene product and a second exogenous gene promoter that regulates a second ectopically expressible nucleic acid molecule encoding a second floral meristem identity gene product.

The present invention further provides a transgenic seed plant containing a first exogenous ectopically expressible nucleic acid molecule encoding a first floral meristem identity gene product and a second exogenous gene promoter that regulates a second ectopically expressible nucleic acid molecule encoding a second floral meristem identity gene product, provided that the first nucleic acid molecule is not ectopically expressed due to a mutation in an endogenous TERMINAL FLOWER gene.

The invention also provides, therefore, a plant characterized by modulated (delayed or early) reproductive development, the plant containing a sense or antisense nucleic acid molecule encoding AP1, or a fragment thereof; a sense or antisense nucleic acid molecule encoding CAL, or a fragment thereof; and a sense or antisense nucleic acid molecule encoding LFY, or a fragment thereof, such that expression of AP1 and LFY gene products, including expression of endogenous AP1 and LFY gene products, is suppressed in the transgenic seed plant. Similarly, a sense or antisense nucleic acid molecule encoding SEP1, or a fragment thereof, a sense or antisense nucleic acid molecule encoding SEP2, or a fragment thereof, a sense or antisense nucleic acid molecule encoding SEP3, or a fragment thereof, a sense or antisense nucleic acid molecule encoding AGL20, or a fragment thereof, a sense or antisense nucleic acid molecule encoding AGL22, or a fragment thereof, a sense or antisense nucleic acid molecule encoding AGL24, or a fragment thereof, a sense or antisense nucleic acid molecule encoding AGL27, or a fragment thereof can also be used singly, in combination with each other or in combination with any of the AP1, CAL or LFY constructs discussed above.

In addition, the invention provides a transgenic seed plant containing a first exogenous ectopically expressible nucleic acid molecule encoding a first floral meristem identity gene product, provided that the first second nucleic acid molecule is not ectopically expressed due to a mutation in an endogenous TERMINAL FLOWER gene, and further containing a second exogenous ectopically expressible nucleic acid molecule encoding a second floral meristem identity gene product, where the first floral meristem identity gene product is different from the second floral meristem identity gene product.

As disclosed herein, ectopic expression of two different floral meristem identity gene products can be particularly useful. For example, a fraction of the progeny of a cross between a transgenic *Arabidopsis* line constitutively expressing AP1 under control of the cauliflower mosaic virus 35S promoter and a transgenic *Arabidopsis* line constitutively expressing LFY under control of the cauliflower mosaic virus 35S promoter are characterized by enhanced early reproductive development as compared to the early reproductive development of 35S-AP1 transgenic lines or 35S-LFY transgenic lines. These results indicate that ectopic expression of the combination of AP1 and LFY in a seed plant can result in enhanced early reproductive development as compared to the early reproductive development obtained by ectopic expression of AP1 or LFY alone. Similarly, the ectopic expression of the combination of at least one of AP1 and CALIFLOWER with at least one of SEP1, SEP2, SEP3, AGL20, AGL22, AGL24 or AGL27 results in early reproductive development. Thus, by using a combination of two different floral meristem identity gene products, plant breeding, for example, can be accelerated further as compared to the use of a single floral meristem identity gene product.

A useful combination of first and second floral meristem identity gene products can be, for example, AP1 and SEP3, CAL and SEP3, AP1 and AGL24 or CAL and AGL24. Where a transgenic seed plant of the invention contains first and second exogenous nucleic acid molecules encoding different floral meristem identity gene products, it will be recognized that the order of introducing the first and second nucleic acid molecules into the seed plant is not important for purposes of the present invention. Thus, a transgenic seed plant of the invention having, for example, AP1 as a first floral meristem identity gene product and SEP3 as a second floral meristem identity gene product is equivalent to a transgenic seed plant having SEP3 as a first floral meristem identity gene product and AP1 as a second floral meristem identity gene product.

IV. Plant Transformation

As used herein, the term "introducing," when used in reference to a nucleic acid molecule and a seed plant such as an angiosperm or a gymnosperm, means transferring an exogenous nucleic acid molecule into the seed plant. For example, an exogenous nucleic acid molecule encoding a floral meristem identity gene product can be introduced into a seed plant by a variety of methods including *Agrobacterium*-mediated transformation or direct gene transfer methods such as electroporation or microprojectile-mediated transformation.

Transformation methods based upon the soil bacterium *Agrobacterium tumefaciens*, known as "agro-infection," are useful for introducing a nucleic acid molecule into a broad range of angiosperms and gymnosperms. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. *Agrobacterium*-based vector is a modified form of a Ti plasmid, in which the tumor inducing functions are replaced by nucleic acid sequence of interest to be introduced into the plant host.

Current protocols for *Agrobacterium*-mediated transformation employ cointegrate vectors or, preferably; binary vector systems in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available from, for example, Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art (Glick and Thompson (eds.), Methods in Plant Molecular Biology and Biotechnology, Boca Raton, Fla.: CRC Press (1993), which is incorporated herein by reference). Wounded cells within the plant tissue that have been infected by *Agrobacterium* can develop organs de novo when cultured under the appropriate conditions; the resulting transgenic shoots eventually give rise to transgenic plants containing the exogenous nucleic acid molecule of interest, as described in Example I.

*Agrobacterium*-mediated transformation has been used to produce a variety of transgenic seed plants (see, for example, Wang et al. (eds), Transformation of Plants and Soil Microorganisms, Cambridge, UK: University Press (1995), which is incorporated herein by reference). For example, *Agrobacterium*-mediated transformation can be used to produce transgenic crudiferous plants such as *Arabidopsis*, mustard, rapeseed and flax; transgenic leguminous plants such as alfalfa, pea, soybean, trefoil and white clover; and transgenic solanaceous plants such as eggplant, petunia, potato, tobacco and tomato. In addition, *Agrobacterium*-mediated transformation can be used to introduce exogenous nucleic acids into apple, aspen, belladonna, black currant, carrot, celery, cotton, cucumber, grape, horseradish, lettuce, morning glory, muskmelon, neem, poplar, strawberry, sugar beet, sunflower, walnut and asparagus plants (see, for example, Glick and Thompson, supra, 1993).

Microprojectile-mediated transformation also is a well known method of introducing an exogenous nucleic acid molecule into a variety of seed plant species. This method, first described by Klein et al., Nature 327:70-73 (1987), which is incorporated herein by reference, relies on microprojectiles such as gold or tungsten that are coated with the desired nucleic acid molecule by precipitation with calcium chloride, spermidine or PEG. The microprojectile particles are accelerated at high speed into seed plant tissue using a device such as the Biolistic™ PD-1000 (Biorad, Hercules, Calif.).

Microprojectile-mediated delivery or "particle bombardment" is especially useful to transform seed plants that are difficult to transform or regenerate using other methods. Microprojectile-mediated transformation has been used, for example, to generate a variety of transgenic seed plant species, including cotton, tobacco, corn, hybrid poplar and papaya (see, for example, Glick and Thompson, supra, 1993). The transformation of important cereal crops such as wheat, oat, barley, sorghum and rice also has been achieved using microprojectile-mediated delivery (Duan et al., *Nature Biotech.* 14:494-498 (1996); Shimamoto, *Curr. Opin. Biotech.* 5:158-162 (1994), each of which is incorporated herein by reference). A rapid transformation regeneration system for the production of transgenic plants, such as transgenic wheat, in two to three months also can be useful in producing a transgenic seed plant of the invention (European Patent No. EP 0 709 462 A2, Application number 95870117.9, filed 25 Oct. 1995, which is incorporated herein by reference).

Thus, a variety of methods for introducing a nucleic acid molecule into a seed plant are well known in the art. Important crop species such as rice, for example, have been transformed using microprojectile delivery, *Agrobacterium*-mediated transformation or protoplast transformation (Hiei et al., *The Plant J.* 6(2):271-282 (1994); Shimamoto, *Science* 270:1772-1773 (1995), each of which is incorporated herein by reference). Fertile transgenic maize has been obtained, for example, by microparticle bombardment (see Wang et al., supra, 1995). As discussed above, barley, wheat, oat and other small-grain cereal crops also have been transformed, for example, using microparticle bombardment (see Wang et al., supra, 1995).

Methods of transforming forest trees including both angiosperms and gymnosperms also are well known in the art. Transgenic angiosperms such as members of the genus *Populus*, which includes aspens and poplars, have been generated using *Agrobacterium*-mediated transformation, for example. In addition, transgenic *Populus* and sweetgum, which are of interest for biomass production for fuel, also have been produced. Transgenic gymnosperms, including conifers such as white spruce and larch, also have been obtained, for example, using microprojectile bombardment (Wang et al., supra, 1995). The skilled artisan will recognize that *Agrobacterium*-mediated or microprojectile-mediated transformation, as disclosed herein, or other methods known in the art can be used to introduce a nucleic acid molecule encoding a floral meristem identity gene product into a seed plant according to the methods of the invention.

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.*

V. Converting Shoot Meristem to Floral Meristem

The term "converting shoot meristem to floral meristem," as used herein, means promoting the formation of flower progenitor tissue where shoot progenitor tissue otherwise would be formed in the angiosperm. As a result of the conversion of shoot meristem to floral meristem, flowers form in an angiosperm where shoots normally would form. The conversion of shoot meristem to floral meristem can be identified using well known methods, such as scanning electron microscopy, light microscopy or visual inspection (see, for example, Mandel and Yanofsky, *Plant Cell* 7:1763-1771 (1995), which is incorporated herein by reference or Weigel and Nilsson, supra, 1995).

Provided herein are methods of converting shoot meristem to floral meristem in an angiosperm by introducing a first ectopically expressible nucleic acid molecule encoding a first floral meristem identity gene product and a second ectopically expressible nucleic acid molecule encoding a second floral meristem identity gene product into the angiosperm, where the first floral meristem identity gene product is different from the second floral meristem identity gene product. As discussed above, first and second floral meristem identity gene products useful in converting shoot meristem to floral meristem in an angiosperm can be, for example, AP1 and LFY, CAL and LFY, or AP1 and CAL. In other preferred embodiments, the ectopic expression of the combination of at least one of AP1 and CALIFLOWER with at least one of SEP1, SEP2, SEP3, AGL20, AGL22, AGL24 or AGL27 results in conversion of shoot meristem to floral meristem.

VI. Methods of Modulating Reproductive Development

As discussed above, the present invention provides methods of promoting modulated timing of reproductive development in a seed plant by ectopically expressing a first nucleic acid molecule encoding a first floral meristem identity gene product in the seed plant, provided that the first nucleic acid molecule is not ectopically expressed due to a mutation in an endogenous TERMINAL FLOWER gene. For example, the invention provides a method of promoting modulated timing of reproductive development in a seed plant by introducing an ectopically expressible nucleic acid molecule encoding a floral meristem identity gene product into the seed plant, thus producing a transgenic seed plant. A floral meristem identity gene product such as SEP1, SEP2, SEP3, AGL20, AGL22, AGL24, AGL27, AP1, CAL or LFY, or a chimeric protein containing, in part, a floral meristem identity gene product, as disclosed below, is useful in methods of promoting early reproductive development.

The term "promoting early reproductive development," as used herein in reference to a seed plant, means promoting the formation of a reproductive structure earlier than the time when a reproductive structure would form on a corresponding seed plant that is grown under the same conditions and that does not ectopically express a floral meristem identity gene product. As discussed above, the time when reproductive structures form on a particular seed plant that does not ectopically express a floral meristem identity gene product is relatively fixed and depends, in part, on genetic factors as well as environmental conditions, such as day length and temperature. Thus, given a defined set of environmental conditions, a naturally occurring angiosperm, for example, will flower at a relatively fixed time. Similarly, given a defined set of environmental conditions, a naturally occurring coniferous gymnosperm, for example, will produce cones at a relatively fixed time.

Methods for ectopically expressing polynucleotides in plants are well known in the art. For example, the expression of polynucleotides of the invention can be modulated by mutation, or introduction of at least one copy of the polynucleotides into a plant.

One of skill will recognize that a number of methods can be used to modulate gene product activity or gene expression. Gene product activity can be modulated in the plant cell at the gene, transcriptional, posttranscriptional, translational, or posttranslational, levels. Techniques for modulating gene product activity at each of these levels are generally well known to one of skill and are discussed briefly below. "Activity" encompasses both mechanistic activities (e.g., enzymatic, ability to induce transcription of genes under the gene products control, etc.) and phenotypic activities such as altering the time of reproductive development.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering the target gene in vivo (see, generally, Grewal and Klar, *Genetics* 146: 1221-1238 (1997) and Xu et al., *Genes Dev.* 10:2411-2422 (1996)). Homologous recombination has been demonstrated in plants (Puchta et al., *Experientia* 50:277-284 (1994), Swoboda et al., *EMBO J.* 13:484-489 (1994); Offringa et al., *Proc. Natl. Acad. Sci. USA* 90: 7346-7350 (1993); and Kempin et al. *Nature* 389:802-803 (1997)).

In applying homologous recombination technology to the genes of the invention, mutations in selected portions of a gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91:4303-4307 (1994); and Vaulont et al. *Transgenic Res.* 4:247-255 (1995) are conveniently used to increase the efficiency of selecting for altered gene expression in transgenic plants. The mutated gene will interact with the target wild-type gene in such a way that homologous recombination and targeted replacement of the wild-type gene will occur in transgenic plant cells, resulting in suppression of gene product activity.

Alternatively, oligonucleotides composed of a contiguous stretch of RNA and DNA residues in a duplex conformation with double hairpin caps on the ends can be used. The RNA/DNA sequence is designed to align with the sequence of the target gene and to contain the desired nucleotide change. Introduction of the chimeric oligonucleotide on an extrachromosomal T-DNA plasmid results in efficient and specific gene conversion directed by chimeric molecules in a small number of transformed plant cells. This method is described in Cole-Strauss et al. *Science* 273:1386-1389 (1996) and Yoon et al. *Proc. Natl. Acad. Sci. USA* 93:2071-2076 (1996).

Gene expression can be inactivated using recombinant DNA techniques by transforming plant cells with constructs comprising transposons or T-DNA sequences. Mutants prepared by these methods are identified according to standard techniques. For instance, mutants can be detected by PCR or by detecting the presence or absence of mRNA, e.g., by Northern blots. Mutants can also be selected by assaying for altered timing of the development of reproductive structures.

The isolated nucleic acid sequences prepared as described herein, can also be used in a number of techniques to control endogenous gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (*Limerick*) 105:125-149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181-238; Heiser et al. *Plant Sci.* (*Shannon*) 127:61-69 (1997)) and by preventing the accumulation of mRNA which encodes the protein of interest, (see, Baulcombe *Plant Mol. Bio.* 32:79-88 (1996); Prins and Goldbach *Arch. Virol.* 141:2259-2276 (1996); Metzlaff et al. *Cell* 88:845-854 (1997), Sheehy et al., *Proc. Nat. Acad. Sci. USA,* 85:8805-8809 (1988), and Hiatt et al., U.S. Pat. No. 4,801,340).

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 7000 nucleotides is especially preferred.

A number of gene regions can be targeted to suppress gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed. In one embodiment, transgenic plants are selected for activity that is reduced but not eliminated.

Oligonucleotide-based triple-helix formation can be used to disrupt gene expression. Triplex DNA can inhibit DNA transcription and replication, generate site-specific mutations, cleave DNA, and induce homologous recombination (see, e.g., Havre and Glazer *J. Virology* 67:7324-7331 (1993); Scanlon et al. *FASEB J.* 9:1288-1296 (1995); Giovannangeli et al. *Biochemistry* 35:10539-10548 (1996); Chan and Glazer *J. Mol. Medicine* (*Berlin*) 75:267-282 (1997)). Triple helix DNAs can be used to target the same sequences identified for antisense regulation.

Catalytic RNA molecules or ribozymes can also be used to inhibit expression of genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of target RNA-specific ribozymes is described in Zhao and Pick *Nature* 365:448-451 (1993); Eastham and Ahlering *J. Urology* 156:1186-1188 (1996); Sokol and Murray *Transgenic Res.* 5:363-371 (1996); Sun et al. *Mol. Biotechnology* 7:241-251 (1997); and Haseloff et al. *Nature,* 334:585-591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22:1067-1085 (1993); Flavell *Proc. Natl. Acad. Sci. USA* 91:3490-3496 (1994); Stam et al. *Annals Bot.* 79:3-12 (1997); Napoli et al., *The Plant Cell* 2:279-289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

In a preferred embodiment, expression of a nucleic acid of interest can be suppressed by the simultaneous expression of both sense and antisense constructs (Waterhouse et al., *Proc. Natl. Acad. Sci. USA* 95:13959-13964 (1998). See also Tabara et al. *Science* 282:430-431 (1998).

Alternatively, gene product activity may be modulated by eliminating the proteins that are required for cell-specific gene expression. Thus, expression of regulatory proteins and/or the sequences that control gene expression can be modulated using the methods described here.

Another method is use of engineered tRNA suppression of mRNA translation. This method involves the use of suppressor tRNAs to transactivate target genes containing premature stop codons (see, Betzner et al. *Plant J.* 11:587-595 (1997); and Choisne et al. *Plant J.* 11:597-604 (1997). A plant line containing a constitutively expressed gene that contains an amber stop codon is first created. Multiple lines of plants, each containing tRNA suppressor gene constructs under the direction of cell-type specific promoters are also generated. The tRNA gene construct is then crossed into the desired gene product line to activate activity in a targeted manner. These tRNA suppressor lines could also be used to target the expression of any type of gene to the same cell or tissue types.

Proteins may form homogeneous or heterologous complexes in vivo. Thus, production of dominant-negative forms of polypeptides that are defective in their abilities to bind to other proteins in the complex is a convenient means to inhibit endogenous gene product activity. This approach involves transformation of plants with constructs encoding mutant polypeptides that form defective complexes and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831-845 (1996).

Another strategy to affect the ability of a protein to interact with itself or with other proteins involves the use of antibodies specific to the protein. In this method cell-specific expression of specific Abs is used inactivate functional domains through antibody:antigen recognition (see, Hupp et al. *Cell* 83:237-245 (1995)).

After plants with reduced activity are identified, a recombinant construct capable of expressing low levels of the gene product can be introduced using the methods discussed below. In this fashion, the level of activity can be regulated to produce preferred plant phenotypes. For example, a relatively weak promoter such as the ubiquitin promoter (see, e.g., Garbarino et al. *Plant Physiol.* 109(4):1371-8 (1995); Christensen et al *Transgenic Res.* 5(3):213-8 (1996); and Holtorf et al. *Plant. Mol. Biol.* 29(4):637-46 (1995)) is useful to produce plants with reduced levels of activity or expression. Such plants are useful for producing, for instance, plants with altered time of developing reproductive structures.

As disclosed herein, ectopic expression of a nucleic acid molecule encoding a floral meristem identity gene product in an angiosperm converts shoot meristem to floral meristem in the angiosperm. Furthermore, ectopic expression of a nucleic acid molecule encoding a floral meristem identity gene product such as AP1, CAL or LFY in an angiosperm prior to the time when endogenous floral meristem identity gene products are expressed in the angiosperm can convert shoot meristem to floral meristem precociously, resulting in early reproductive development in the angiosperm, as indicated by early flowering. In the same manner, ectopic expression of a nucleic acid molecule encoding AP1, CAL, or LFY, for example, in a gymnosperm prior to the time when endogenous floral meristem identity gene products are expressed in the gymnosperm results in early reproductive development in the gymnosperm.

For a given seed plant species and particular set of growth conditions, constitutive expression of a floral meristem identity gene product results in a relatively invariant time of early reproductive development, which is the earliest time when all factors necessary for reproductive development are active. For example, constitutive expression of AP1 in transgenic *Arabidopsis* plants grown under "long-day" light conditions results in early reproductive development at day 10 as compared to the normal time of reproductive development, which is day 18 in non-transgenic *Arabidopsis* plants grown under the same conditions. Thus, under these conditions, day 10 is the relatively invariant time of early reproductive development for *Arabidopsis* transgenics that constitutively express a floral meristem identity gene product. Similarly, transgenic plants constitutively expressing SEP3 result in plants that develop earlier reproductive structures than wild type plants.

However, in addition to methods of constitutively expressing a floral meristem identity gene product, the present invention provides methods of selecting the time of early reproductive development. As disclosed herein, floral meristem gene product expression or activity can be regulated in response to an inducing agent or cognate ligand, for example, such that the time of reproductive development can be selected. For example, in *Arabidopsis* transgenics grown under the conditions described above, the time of early reproductive development need not necessarily be the relatively invariant day 10 at which early reproductive development occurs as a consequence of constitutive floral meristem identity gene product expression. If floral meristem identity gene product expression is rendered dependent upon the presence of an inducing agent, early reproductive development can be selected to occur, for example, on day 14, by contacting the seed plant with an inducing agent on or slightly before day 14.

Thus, the present invention provides recombinant nucleic acid molecules, transgenic seed plant containing such recombinant nucleic acid molecules and methods for selecting the time of early reproductive development. These methods allow a farmer or horticulturist, for example, to determine the time of early reproductive development. The methods of the invention can be useful, for example, in allowing a grower to respond to an approaching storm or impending snap-freeze by selecting the time of early reproductive development such that the crop can be harvested before being harmed by the adverse weather conditions. The methods of the invention for selecting the time of early reproductive development also can be useful to spread out the time period over which transgenic seed plants are ready to be harvested. For example, the methods of the invention can be used to increase floral meristem identity gene product expression in different crop fields at different times, resulting in a staggered time of harvest for the different fields. Thus, the present invention provides a recombinant nucleic acid molecule containing an inducible regulatory element operably linked to a nucleic acid molecule encoding a floral meristem identity gene product. The floral meristem identity gene product encoded within a recombinant nucleic acid molecule of the invention can be, for example, SEP1, SEP2, SEP3, AGL20, AGL22, AGL24, AGL27, AP1 or CAL. In addition, the floral meristem identity gene product encoded within a recombinant nucleic acid molecule of the invention can be LFY. As disclosed herein, a recombinant nucleic acid molecule of the invention can contain an inducible regulatory element such as a copper inducible element, tetracycline inducible element, ecdysone inducible element or heat shock inducible element.

VII. Inducible Regulatory Elements

The invention also provides a transgenic seed plant containing a recombinant nucleic acid molecule comprising an inducible regulatory element operably linked to a nucleic acid molecule encoding a floral meristem identity gene product. Such a transgenic seed plant can be an angiosperm or gymnosperm and can contain, for example, a recombinant nucleic acid molecule comprising an inducible regulatory element operably linked to a nucleic acid molecule encoding AP1 or CAL. Similarly, the ectopic expression of the combination of at least one of AP1 and CALIFLOWER with at least one of SEP1, SEP2, SEP3, AGL20, AGL22, AGL24 or AGL27 can be used to produce seed with various desirable phenotypes. A transgenic seed plant of the invention can contain, for example, a recombinant nucleic acid molecule comprising a copper inducible element, tetracycline inducible element, ecdysone inducible element or heat shock inducible element operably linked to a nucleic acid molecule encoding AP1, SEP1, SEP2, SEP3, AGL20, AGL22, AGL24 or AGL27. In addition, a transgenic seed plant of the invention can contain a recombinant nucleic acid molecule comprising a copper inducible element tetracycline inducible element, ecdysone inducible element or heat shock inducible element operably linked to a nucleic acid molecule encoding CAL. A transgenic seed plant of the invention also can contain a recombinant nucleic acid molecule comprising a copper inducible element, tetracycline inducible element, ecdysone inducible element or heat shock inducible element operably linked to a nucleic acid molecule encoding LFY.

A particularly useful inducible regulatory element can be, for example, a copper-inducible promoter (Mett et al., *Proc. Natl. Acad. Sci. USA* 90:4567-4571 (1993), which is incorporated herein by reference); tetracycline-inducible regulatory element (Gatz et al., *Plant J.* 2:397-404 (1992); Roder et al., *Mol. Gen. Genet.* 243:32-38 (1994), each of which is incorporated herein by reference); ecdysone inducible element (Christopherson et al., *Proc. Natl. Acad. Sci. USA* 89:6314-6318 (1992), which is incorporated herein by reference); or heat shock inducible element (Takahashi et al., *Plant Physiol.* 99:383-390 (1992), which is incorporated herein by reference). Another useful inducible regulatory element can be a lac operon element, which is used in combination with a constitutively expressed lac repressor to confer, for example, IPTG-inducible expression, as described by Wilde et al., (*EMBO J.* 11:1251-1259 (1992), which is incorporated herein by reference).

An inducible regulatory element useful in a method of the invention also can be, for example, a nitrate-inducible promoter derived from the spinach nitrite reductase gene (Back et al., *Plant Mol. Biol.* 17:9 (1991), which is incorporated herein by reference) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990), each of which is incorporated herein by reference). An inducible regulatory element useful in constructing a transgenic seed plant also can be a salicylic acid inducible element (Uknes et al., *Plant Cell* 5:159-169 (1993); Bi et al., *Plant J.* 8:235-245 (1995), each of which is incorporated herein by reference) or a plant hormone-inducible element (Yamaguchi-Shinozaki et al., *Plant Mol. Biol.* 15:905 (1990); Kares et al., *Plant Mol. Biol.* 15:225 (1990), each of which is incorporated herein by reference). A human glucocorticoid response element also is an inducible regulatory element that can confer hormone-dependent gene expression in seed plants (Schena et al., *Proc. Natl. Acad. Sci. USA* 88:10421 (1991), which is incorporated herein by reference).

An inducible regulatory element that is particularly useful for increasing expression of a floral meristem identity gene product in a transgenic seed plant of the invention is a copper inducible regulatory element (see, for example, Mett et al., supra, 1993). Thus, the invention provides a recombinant nucleic acid molecule comprising a copper inducible regulatory element operably linked to a nucleic acid molecule encoding a floral meristem identity gene product and a transgenic seed plant containing such a recombinant nucleic acid molecule. Copper, which is a natural part of the nutrient environment of a seed plant, can be used to increase expression of a nucleic acid molecule encoding a floral meristem identity gene product operably linked to a copper inducible regulatory element. For example, an ACE1 binding site in conjunction with constitutively expressed yeast ACE1 protein confers copper inducible expression upon an operably linked nucleic acid molecule. The ACE1 protein, a metalloresponsive transcription factor, is activated by copper or silver ions, resulting in increased expression of a nucleic acid molecule operably linked to an ACE1 element.

Such a copper inducible regulatory element can be an ACE1 binding site from the metallothionein gene promoter (SEQ ID NO: 21; Furst et al., *Cell* 55:705-717 (1988), which is incorporated herein by reference). For example, the ACE1 binding site can be combined with the 90 base-pair domain A of the cauliflower mosaic virus 35S promoter and operably linked to a nucleic acid molecule encoding AP1, CAL or LFY to produce a recombinant nucleic acid molecule of the invention. In a transgenic seed plant constitutively expressing ACE1 under control of such a modified CaMV 35S promoter, for example, copper inducible expression is conferred upon an operably linked nucleic acid molecule encoding a floral meristem identity gene product.

The expression of a nucleic acid encoding a floral meristem identity gene product operably linked to a copper inducible regulatory element, such as 5'-AGCTTAGCGATGCGTCTTTTCCGCTGAACCGTTCCAG-CAAAAAAGACTAG-3' (SEQ ID NO: 21), can be increased in a transgenic seed plant grown under copper ion-depleted conditions, for example, and contacted with 50 μM copper sulfate in a nutrient solution or with 0.5 μM copper sulfate applied by foliar spraying of the transgenic seed plant (see, for example, Mett et al., supra, 1993). A single application of 0.5 μM copper sulfate can be sufficient to sustain increased floral meristem identity gene product expression over a period of several days. If desired, a transgenic seed plant of the invention also can be contacted with multiple applications of an inducing agent such as copper sulfate.

An inducible regulatory element also can confer tetracycline-dependent floral meristem identity gene expression in a transgenic seed plant of the invention. Thus, the present invention provides a recombinant nucleic acid molecule comprising a tetracycline inducible regulatory element operably linked to a nucleic acid molecule encoding a floral meristem identity gene product as well as a transgenic seed plant into which such a recombinant nucleic acid molecule has been introduced. A tetracycline inducible regulatory element is particularly useful for conferring tightly regulated gene expression as indicated by the observation that a phenotype that results from even low amounts of a gene product expression is suppressed from such an inducible system in the absence of inducing agent (see, for example, Röder et al., supra, 1994).

A transgenic seed plant constitutively expressing Tn10-encoded Tet repressor (TetR), for example, can be contacted with tetracycline to increase expression of a nucleic acid molecule encoding a floral meristem identity gene product operably linked to the cauliflower mosaic virus promoter containing several tet operator sequences (5'-ACTCTAT-CAGTGATAGAGT-3'; SEQ ID NO: 22) positioned close to the TATA box (see, for example, Gatz, *Meth. Cell Biol.* 50:411-424 (1995), which is incorporated herein by reference; Gatz et al., supra, 1992). Such a tetracycline-inducible system can increase expression of an operably linked nucleic acid molecule as much as 200 to 500-fold in a transgenic angiosperm or gymnosperm of the invention.

A high level of Tet repressor expression (about $1\times10^6$ molecules per cell) is critical for tight regulation. Thus, a seed plant preferably is transformed first with a plasmid encoding the Tet repressor, and screened for high level expression. For example, plasmid pBinTet (Gatz, supra, 1995) contains the Tet repressor coding region, which is expressed under control of the CaMV 35S promoter, and the neomycin phosphotransferase gene for selection of transformants. To screen transformants for a high level of Tet repressor expression, a plasmid containing a reporter gene under control of a promoter with tet operators, such as pTX-Gus-int (Gatz, supra, 1995), can be transiently introduced into a seed plant cell and assayed for activity in the presence and absence of tetracycline. High β-glucouronidase (GUS) expression that is dependent on the presence of tetracycline is indicative of high Tet repressor expression.

A particularly useful tetracycline inducible regulatory element is present in plasmid pBIN-HygTX, which has a CaMV 35S promoter, into which three tet operator sites have been inserted, and an octopine synthase polyadenylation site (Gatz, supra, 1995). A multiple cloning site between the promoter and polyadenylation signal in pBIN-HygTX allows for convenient insertion of a nucleic acid molecule encoding the desired floral meristem identity gene product, and the hygromycin phosphotransferase gene allows for selection of transformants containing the construct. In a preferred embodiment of the invention, previously selected Tet repressor positive cells are transformed with a plasmid such as pBIN-HygTX, into which a nucleic acid molecule encoding a floral meristem identity gene product has been inserted.

To increase floral meristem identity gene product expression using a tetracycline-inducible regulatory element, a transgenic seed plant of the invention can be contacted with tetracycline or, preferably, with chlor-tetracycline (SIGMA), which is a more efficient inducer than tetracycline. In addition, a useful inducing agent can be a tetracycline analog that binds the Tet repressor to function as an inducer but that does not act as an antibiotic (Gatz, supra, 1995). A transgenic seed plant of the invention can be contacted, for example, by watering with about 1 mg/liter chlor-tetracycline or tetracycline. Similarly, a plant grown in hydroponic culture can be contacted with a solution containing about 1 mg/liter chlor-tetracycline or tetracycline (Gatz, supra, 1995). If desired, a transgenic angiosperm or gymnosperm can be contacted repeatedly with chlor-tetracycline or tetracycline every other day for about 10 days (Roder et al., supra, 1994). Floral meristem identity gene product expression is increased efficiently at a tetracycline concentration that does not inhibit the growth of bacteria, indicating that the use of tetracycline as an inducing agent will not present environmental concerns.

An ecdysone inducible regulatory element also can be useful in practicing the methods of the invention. For example, an ecdysone inducible regulatory element can contain four copies of an ecdysone response element having the sequence 5'-GATCCGACAAGGGTTCAATGCACT-TGTCA-3' (EcRE; SEQ ID NO: 23) as described in Christopherson et al., supra, 1992. In a transgenic seed plant into which a nucleic acid encoding an ecdysone receptor has been introduced, an ecdysone inducible regulatory element can confer ecdysone-dependent expression on a nucleic acid molecule encoding a floral meristem identity gene product. An appropriate inducing agent for increasing expression of a nucleic acid molecule operably linked to an ecdysone inducible regulatory element can be, for example, ∀-ecdysone, 20-hydroxyecdysone, polypodine B, ponasterone A, muristerone A or RH-5992, which is an ecdysone agonist that mimics 20-hydroxyecdysone (see, for example, Kreutzweiser et al., *Ecotoxicol. Environ. Safety* 28:14-24 (1994), which is incorporated herein by reference and Christopherson et al., supra, 1992). Methods for determining an appropriate inducing agent for use with an ecdysone inducible regulatory element are well known in the art. As disclosed herein, compound RH-5992 can be a particularly useful inducing agent for increasing floral meristem gene product expression in a transgenic seed plant containing an ecdysone inducible regulatory element.

An inducible regulatory element also can be derived from the promoter of a heat shock gene, such as HSP81-1 (SEQ ID NO: 24; Takahashi, supra, 1992). Thus, the invention also provides a recombinant nucleic acid molecule comprising a heat shock inducible regulatory element operably linked to a nucleic acid molecule encoding a floral meristem identity gene product and a transgenic seed plant containing such a recombinant nucleic acid molecule. The HSP81-1 promoter (SEQ ID NO: 24) confers low level expression upon an operably linked nucleic acid molecule in parts of roots under unstressed conditions and confers high level expression in most *Arabidopsis* tissues following heat shock (see, for example, Yabe et al., *Plant Cell Physiol.* 35:1207-1219 (1994), which is incorporated herein by reference). After growth of *Arabidopsis* at 23EC, a single heat shock treatment at 37EC for two hours is sufficient to induce expression of a nucleic acid molecule operably linked to the HSP81-1 gene regulatory element (see Ueda et al., *Mol. Gen. Genet.* 250:533-539 (1996), which is incorporated herein by reference).

The use of a heat shock inducible regulatory element is particularly useful for a transgenic seed plant of the invention grown in an enclosed environment such as a greenhouse, where temperature can be readily manipulated. The use of a heat shock inducible regulatory element especially is applicable to a transplantable or potted transgenic seed plant of the invention, which can be moved conveniently from an environment having a low temperature to an environment having a high temperature. A transgenic angiosperm or gymnosperm of the invention containing a recombinant nucleic acid molecule comprising a HSP81-1 heat shock regulatory element operably linked to a nucleic acid molecule encoding a floral meristem identity gene product also can be induced, for example, by altering the ambient temperature, watering with heated water or submersing the transgenic seed plant in a sealed plastic bag into a heated water bath (see, for example, Ueda et al., supra, 1996).

A recombinant nucleic acid molecule of the invention comprising an inducible gene regulatory element can be expressed variably in different lines of transgenic seed plants. In some transgenic lines, for example, leaky expression of the introduced recombinant nucleic acid molecule can occur in the absence of the appropriate inducing agent due to phenomena such as position effects (see, for example, Ueda et al., supra, 1996). Thus, a transgenic seed plant containing a recombinant nucleic acid molecule comprising an inducible gene regulatory element operably linked to a nucleic acid encoding a floral meristem identity gene product can be screened, if desired, to obtain a particular transgenic seed plant in which expression of the operably linked nucleic acid molecule is desirably low in the absence of the appropriate inducing agent.

The present invention also provides a method of converting shoot meristem to floral meristem in an angiosperm by introducing into the angiosperm a recombinant nucleic acid molecule comprising an inducible regulatory element operably linked to a nucleic acid molecule encoding a floral meristem identity gene product to produce a transgenic angiosperm, and contacting the transgenic angiosperm with an inducing agent, thereby increasing expression of the floral meristem identity gene product and converting shoot meristem to floral meristem in the transgenic angiosperm. In such a method of the invention, the inducible regulatory element can be, for example, a copper inducible element, tetracycline inducible element, ecdysone inducible element or heat shock inducible element, and the floral meristem identity gene product can be, for example, AP1, CAL, LFY, SEP1, SEP2, SEP3, AGL20, AGL22, AGL24 or AGL27.

In addition, the invention provides a method of promoting early reproductive development in a seed plant such as an angiosperm or gymnosperm by introducing into the seed plant a recombinant nucleic acid molecule comprising an inducible regulatory element operably linked to a nucleic acid molecule encoding a floral meristem identity gene product to produce a transgenic seed plant, and contacting the transgenic seed plant with an inducing agent, thereby increasing expression of the floral meristem identity gene product and promoting early reproductive development in the transgenic seed plant. In a method of the invention for promoting early reproductive development in a seed plant, the inducible regulatory element can be, for example, a copper inducible element, tetracycline inducible element, ecdysone inducible element or heat shock inducible element, and the floral meristem identity gene product can be, for example, AP1, CAL, LFY, SEP1, SEP2, SEP3, AGL20, AGL22, AGL24 or AGL27.

The term "inducing agent," as used herein, means a substance or condition that effects increased expression of a nucleic acid molecule operably linked to a particular inducible regulatory element as compared to the level of expression of the nucleic acid molecule in the absence of the inducing agent. An inducing agent can be, for example, a naturally occurring or synthetic chemical or biological molecule such as a simple or complex organic molecule, a peptide, a protein or an oligonucleotide that increases expression of a nucleic acid molecule operably linked to a particular inducible regulatory element. An example of such an inducing agent is a compound such as copper sulfate, tetracycline or an ecdysone. An inducing agent also can be a condition such as heat of a certain temperature or light of a certain wavelength. When used in reference to a particular inducible regulatory element, an "appropriate" inducing agent means an inducing agent that results in increased expression of a nucleic acid molecule operably linked to the particular inducible regulatory element.

An inducing agent of the invention can be used alone or in solution or can be used in conjunction with an acceptable carrier that can serve to stabilize the inducing agent or to promote absorption of the inducing agent by a seed plant. If desired, a transgenic seed plant of the invention can be contacted with an inducing agent in combination with an unrelated substance such as a plant nutrient, pesticide or insecticide.

One skilled in the art can readily determine the optimum concentration of an inducing agent needed to produce increased expression of a nucleic acid molecule operably linked to an inducible regulatory element in a transgenic seed plant of the invention. For conveniently determining the optimum concentration of inducing agent from a range of useful concentrations, one skilled in the art can operably link the particular inducible regulatory element to a nucleic acid molecule encoding a reporter gene product such as β-glucuronidase (GUS) and assay for reporter gene product activity in the presence of various concentrations of inducing agent (see, for example, Jefferson et al., *EMBO J.* 6:3901-3907 (1987), which is incorporated herein by reference).

As used herein, the term "contacting," in reference to a transgenic seed plant of the invention, means exposing the transgenic seed plant to an inducing agent, or to a cognate ligand as disclosed below, such that the agent can induce expression of a nucleic acid molecule operably linked to the particular inducible regulatory element. A transgenic seed plant such as an angiosperm or gymnosperm, which contains a recombinant nucleic acid molecule of the invention, can be contacted with an inducing agent in a variety of manners. Expression of a floral meristem identity gene product can be increased conveniently, for example, by spraying a transgenic seed plant with an aqueous solution containing an appropriate inducing agent or by adding an appropriate inducing agent to the water supply of a transgenic seed plant grown using irrigation or to the water supply of a transgenic seed plant grown hydroponically. A transgenic seed plant containing a recombinant nucleic acid molecule of the invention also can be contacted by spraying the seed plant with an inducing agent in aerosol form. In addition, a transgenic seed plant can be contacted with an appropriate inducing agent by adding the agent to the soil or other solid nutrient media in which the seed plant is grown, whereby the inducing agent is absorbed into the seed plant. Other modes of contacting a transgenic seed plant with an inducing agent, such as injecting or immersing the seed plant in a solution containing an inducing agent, are well known in the art. For an inducing agent that is temperature or light, for example, contacting can be effected by altering the temperature or light to which the transgenic seed plant is exposed, or, if desired, by moving the transgenic seed plant from an environment of one temperature or light source to an environment having the appropriate inducing temperature or light source.

If desired, a transgenic seed plant of the invention can be contacted individually with an inducing agent. Furthermore, a group of transgenic seed plants that, for example, are located together in a garden plot, hot house or field, can be contacted en masse with an inducing agent, such that floral meristem identity gene product expression is increased coordinately in all transgenic seed plants of the group.

A transgenic seed plant of the invention can be contacted with an inducing agent using one of several means. For example, a transgenic seed plant can be contacted with an inducing agent by non-automated means such as with a hand held spraying apparatus. Such manual means can be useful when the methods of the invention are applied to particularly delicate or valuable seed plant varieties or when it is desirable, for example, to promote early reproductive development in a particular transgenic seed plant without promoting early reproductive development in a neighboring transgenic seed plant. Furthermore, a transgenic seed plant of the invention can be contacted with an inducing agent by mechanical means such as with a conventional yard "sprinkler" for a transgenic seed plant grown, for example, in a garden; a mechanical spraying system in a green house; traditional farm machinery for spraying field crops; or "crop dusting" for conveniently contacting an entire field of transgenic seed plants with a particulate or gaseous inducing agent. The skilled practitioner, whether home gardener or commercial farmer, recognizes that these and other manual or mechanical means can be used to contact a transgenic seed plant with an inducing agent according to the methods of the invention.

Furthermore, it is recognized that a transgenic seed plant of the invention can be contacted with a single treatment of an inducing agent or, if desired, can be contacted with multiple applications of the inducing agent. In a preferred embodiment of the invention, a transgenic seed plant of the invention is contacted once with an inducing agent to effectively increase floral meristem identity gene product expression, thereby promoting early reproductive development in the transgenic seed plant. Similarly, a transgenic angiosperm of the invention preferably is contacted once with an inducing agent to effectively increase floral meristem identity gene product expression and convert shoot meristem to floral meristem in the transgenic angiosperm.

A single application of an inducing agent is preferable when a transient increase in floral meristem identity gene product expression from a recombinant nucleic acid molecule of the invention promotes irreversible early reproductive development in a seed plant. In many seed plant species, early reproductive development is irreversible. Transient expression of a floral meristem identity gene product from an introduced recombinant nucleic acid molecule, for example, results in sustained ectopic expression of endogenous floral meristem identity gene products, resulting in irreversible early reproductive development. For example, ectopic expression of AP1 in a transgenic plant induces endogenous LFY gene expression, and ectopic expression of LFY induces endogenous AP1 gene expression (Mandel and Yanofsky, *Nature* 377:522-524 (1995), which is incorporated herein by reference; Weigel and Nilsson, supra, 1995). Genetic studies also indicate that CAL can act directly or indirectly to increase expression of AP1 and LFY. Thus, ectopic expression of CAL from an exogenous nucleic acid molecule, for example, can induce endogenous AP1 and LFY expression (see Bowman et al., supra, 1993). Enhanced expression of endogenous AP1, LFY or CAL following a transient increase in expression of an introduced floral meristem identity gene product induced by a single application of an inducing agent can make repeated applications of an inducing agent unnecessary.

In some seed plants, however, such as angiosperms characterized by the phenomenon of floral reversion, repeated applications of the inducing agent can be desirable. In species such as impatiens, an initiated flower can revert into a shoot such that the center of the developing flower behaves as an indeterminate shoot (see, for example, Battey and Lyndon, *Ann. Bot.* 61:9-16 (1988), which is incorporated by reference herein). Thus, to prevent floral reversion in species such as impatiens, repeated applications of an inducing agent can be useful. Repeated applications of an inducing agent, as well as single applications, are encompassed within the scope of the present invention.

VIII. Chimeric Polypepides of the Invention

The invention further provides a nucleic acid molecule encoding a chimeric protein, which comprises a nucleic acid molecule encoding a floral meristem identity gene product such as SEP1, SEP2, SEP3, AGL20, AGL22, AGL24, AGL27, AP1, CAL or LFY linked in frame to a nucleic acid molecule encoding a ligand binding domain. Expression of a chimeric protein of the invention in a seed plant is useful because the ligand binding domain renders the activity of a linked gene product dependent on the presence of cognate ligand. Specifically, in a chimeric protein of the invention, floral meristem gene product activity is increased in the presence of cognate ligand, as compared to activity in the absence of cognate ligand.

A nucleic acid molecule encoding a chimeric protein of the invention comprises a nucleic acid molecule encoding a floral meristem identity gene product, such as a nucleic acid molecule having the nucleic acid sequence SEQ ID NO: 1, SEQ ID NO: 9, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, which encode AP1, CAL, LFY, SEP1, SEP2, SEP3, AGL20, AGL22, AGL24 and AGL27, respectively, any of which is linked in frame to a nucleic acid molecule encoding a ligand binding domain. The expression of such a nucleic acid molecule results in the production of a chimeric protein containing a floral meristem identity gene product fused to a ligand binding domain. Thus, the invention also provides a chimeric protein containing a floral meristem identity gene product fused to a ligand binding domain and an antibody that specifically binds such a chimeric protein.

The invention further provides a transgenic seed plant, such as angiosperm or gymnosperm, that contains a nucleic acid molecule encoding a chimeric protein of the invention. The invention provides, for example, a transgenic seed plant containing a nucleic acid molecule encoding a chimeric protein, which comprises a nucleic acid molecule encoding AP1, CAL or LFY linked in frame to a nucleic acid molecule encoding a ligand binding domain. A particularly useful transgenic seed plant contains a nucleic acid molecule encoding AP1 linked in frame to a nucleic acid molecule encoding an ecdysone receptor ligand binding domain or a glucocorticoid receptor ligand binding domain. The invention also provides a transgenic seed plant containing a nucleic acid molecule encoding a chimeric protein, which comprises a nucleic acid molecule encoding CAL linked in frame to a nucleic acid molecule encoding an ecdysone receptor ligand binding domain or a glucocorticoid receptor ligand binding domain. In addition, there is provided a transgenic seed plant containing a nucleic acid molecule encoding a chimeric protein, which comprises a nucleic acid molecule encoding LFY linked in frame to a nucleic acid molecule encoding an ecdysone receptor ligand binding domain or a glucocorticoid receptor ligand binding domain.

Any floral meristem identity gene product, as defined herein, is useful in a chimeric protein of the invention. Thus, a nucleic acid molecule encoding *Arabidopsis thaliana*AP1, *Brassica oleracea* AP1 SEQ JD NO:4), *Brassica oleracea* var. *Botrytis* AP1 SEQ ID NO:6) or *Zea mays* AP1 SEQ ID NO:8), each of which have activity in converting shoot meristem to floral meristem, can be used to construct a nucleic acid molecule encoding a chimeric protein of the invention. Similarly, a nucleic acid molecule encoding, for example, *Arabidopsis thaliana* CAL SEQ ID NO:10), *Brassica oleracea* CAL SEQ ID NO:12), or a nucleic acid molecule encoding *Arabidopsis thaliana* LFY SEQ ID NO: 16) is useful when linked in frame to a nucleic acid molecule encoding a ligand binding domain to produce a nucleic acid molecule encoding a ligand-dependent chimeric protein of the invention. Similarly, nucleic acids encoding SEP1, SEP2, SEP3, AGL2O, AGL22, AGL24 or AGL27 can be operably linked to a nucleic acid encoding a ligand binding domain.

A ligand binding domain useful in a chimeric protein of the invention is a domain that, when fused in frame to a heterologous gene product, renders the activity of the fused gene product dependent on cognate ligand such that the activity of the fused gene product is increased in the presence of cognate ligand as compared to its activity in the absence of ligand. Such a ligand binding domain can be a steroid binding domain such as the ligand binding domain of an ecdysone receptor, glucocorticoid receptor, estrogen receptor, progesterone receptor, androgen receptor, thyroid receptor, vitamin D receptor or retinoic acid receptor. A particularly useful ligand binding domain is the ecdysone receptor ligand binding domain contained within amino acids 329 to 878 of the *Drosophila ecdysone* receptor (SEQ ID NO: 18); Koelle et al., *Cell* 67:59-77 (1991); Thummel, *Cell* 83:871-877 (1995), each of which is incorporated herein by reference) or a glucocorticoid receptor ligand binding domain, encompassed, for example, within amino acids 512 to 795 of the rat glucocorticoid receptor (SEQ ID NO: 20; Miesfeld et al., *Cell* 46:389-399 (1986), which is incorporated herein by reference).

A chimeric protein of the invention containing an ecdysone receptor ligand binding domain has floral meristem identity gene product activity that can be increased in the presence of ecdysone ligand. Similarly, a chimeric protein of the invention containing a glucocorticoid receptor ligand binding domain has floral meristem identity gene product activity that is increased in the presence of glucocorticoid ligand. It is well known that in a chimeric protein containing a heterologous gene product such as adenovirus E1A, c-myc, c-fos, the HIV-1 Rev transactivator, MyoD or maize regulatory factor R fused to the rat glucocorticoid receptor ligand binding domain, activity of the fused heterologous gene product can be increased by glucocorticoid ligand (Eilers et al., *Nature* 340:66 (1989); Superti-Furga et al., *Proc. Natl. Acad. Sci., U.S.A.* 88:5114 (1991); Hope et al., *Proc. Natl. Acad. Sci., U.S.A.* 87:7787 (1990); Hollenberg et al., *Proc. Natl. Acad. Sci., U.S.A.* 90:8028 (1993), each of which is incorporated herein by reference).

A nucleic acid molecule encoding a chimeric protein of the invention can be introduced into a seed plant where, under appropriate conditions, the chimeric protein is expressed. In such a transgenic seed plant, floral meristem identity gene product activity can be increased by contacting the transgenic seed plant with cognate ligand. For example, activity of a heterologous protein fused to a rat glucocorticoid receptor ligand binding domain (amino acids 512 to 795) expressed under the control of the constitutive cauliflower mosaic virus 35S promoter in *Arabidopsis* was low in the absence of glucocorticoid ligand; whereas, upon contacting the transformed plants with a synthetic glucocorticoid, dexamethasone, activity of the protein was increased greatly (Lloyd et al., *Science* 266:436-439 (1994), which is incorporated herein by reference). As disclosed herein, a ligand binding domain fused to a floral meristem identity gene product renders the activity of a fused floral meristem identity gene product ligand-dependent such that, upon contacting the transgenic seed plant with cognate ligand, floral meristem identity gene product activity is increased.

Methods for constructing a nucleic acid molecule encoding a chimeric protein of the invention are routine and well known in the art (Sambrook et al., supra, 1989). Methods of constructing, for example, a nucleic acid encoding an AP1-glucocorticoid receptor ligand binding domain chimeric protein are described in Example IV of WO 97/46078. For example, the skilled artisan recognizes that a stop codon encoded by the nucleic acid molecule must be removed and that the two nucleic acid molecules must be linked in frame such that the reading frame of the 3' nucleic acid molecule coding sequence is preserved. Methods of transforming a seed plant such as an angiosperm or gymnosperm with a nucleic acid molecule are disclosed above and well known in the art (see Examples I, II and III of WO 97/46078; see, also, Mohoney et al., U.S. Pat. No. 5,463,174, and Barry et al., U.S. Pat. No. 5,463,175, each of which is incorporated herein by reference).

As used herein, the term "linked in frame," when used in reference to two nucleic acid molecules that make up a nucleic acid molecule encoding a chimeric protein, means that the two nucleic acid molecules are linked in the correct reading frame such that, under appropriate conditions, a full-length chimeric protein is expressed. In particular, a 5' nucleic acid molecule, which encodes the amino-terminal portion of the chimeric protein, must be linked to a 3' nucleic acid molecule, which encodes the carboxyl-terminal portion of the chimeric protein, such that the carboxyl-terminal portion of the chimeric protein is translated in the correct reading frame. One skilled in the art would recognize that a nucleic acid molecule encoding a chimeric protein of the invention can comprise, for example, a 5' nucleic acid molecule encoding a floral meristem identity gene product linked in frame to a 3' nucleic acid molecule encoding a ligand binding domain or can comprise a 5' nucleic acid molecule encoding a ligand binding domain linked in frame to a 3' nucleic acid molecule encoding a floral meristem identity gene product. Preferably, a nucleic acid molecule encoding a chimeric protein of the invention comprises a 5' nucleic acid molecule encoding a floral meristem identity gene product linked in frame to a 3' nucleic acid molecule encoding a ligand binding domain.

In a transgenic angiosperm containing a chimeric protein of the invention, conversion of shoot meristem to floral meristem can be induced by contacting the transgenic angiosperm with a cognate ligand that is absorbed by the angiosperm and binds the chimeric protein within its ligand binding domain. Thus, the present invention provides a method of converting shoot meristem to floral meristem in an angiosperm by introducing into the angiosperm a nucleic acid molecule encoding a chimeric protein to produce a transgenic angiosperm, where, under appropriate conditions, the chimeric protein containing a floral meristem identity gene product fused to a ligand binding domain is expressed; and contacting the transgenic angiosperm with cognate ligand, where, upon binding of the cognate ligand to the ligand binding domain, floral meristem identity gene product activity is increased, thereby converting shoot meristem to floral meristem in the transgenic angiosperm.

The present invention provides, for example, a method of converting shoot meristem to floral meristem in an angiosperm by introducing into the angiosperm a nucleic acid molecule encoding a chimeric protein, which comprises a nucleic acid molecule encoding SEP1, SEP2, SEP3, AGL20, AGL22, AGL24, AGL27, AP1, CAL or LFY linked in frame to a nucleic acid molecule encoding an ecdysone receptor ligand binding domain, to produce a transgenic angiosperm, where, under appropriate conditions, the chimeric protein is expressed; and contacting the transgenic angiosperm with ecdysone ligand, where, upon binding of the ecdysone ligand to the ecdysone receptor ligand binding domain, floral meristem identity gene product activity is increased, thereby converting shoot meristem to floral meristem in the transgenic angiosperm. Similarly, the invention provides, for example, a method of converting shoot meristem to floral meristem in an angiosperm by introducing into the angiosperm a nucleic acid molecule encoding a chimeric protein, which comprises a nucleic acid molecule encoding SEP1, SEP2, SEP3, AGL20, AGL22, AGL24, AGL27, AP1, CAL or LFY linked in frame to a nucleic acid molecule encoding a glucocorticoid receptor ligand binding domain, to produce a transgenic angiosperm, where, under appropriate conditions, the chimeric protein is expressed; and contacting the transgenic angiosperm with glucocorticoid ligand, where, upon binding of the glucocorticoid ligand to the glucocorticoid receptor ligand binding domain, floral meristem identity gene product activity is increased, thereby converting shoot meristem to floral meristem in the transgenic angiosperm.

In addition, the invention provides a method of promoting early reproductive development in a seed plant by introducing into the seed plant a nucleic acid molecule encoding a chimeric protein of the invention to produce a transgenic seed plant, where, under appropriate conditions, the chimeric protein containing a floral meristem identity gene product fused to a ligand binding domain is expressed; and contacting the transgenic seed plant with cognate ligand, where, upon binding of the cognate ligand to the ligand binding domain, floral meristem identity gene product activity is increased, thereby promoting early reproductive development in the transgenic seed plant. The methods of the invention can be practiced with numerous seed plant varieties. The seed plant can be, for example, an angiosperm such as a cereal plant, leguminous plant, hardwood tree or coffee plant, or can be a gymnosperm such as a pine, fir, spruce or redwood tree.

There is provided, for example, a method of promoting early reproductive development in a seed plant by introducing into the seed plant a nucleic acid molecule encoding a chimeric protein, which comprises a nucleic acid molecule encoding a floral meristem identity gene product linked in frame to a nucleic acid molecule encoding an ecdysone receptor ligand binding domain, to produce a transgenic seed plant, where, under appropriate conditions, the chimeric protein is expressed; and contacting the transgenic seed plant with ecdysone ligand, where, upon binding of the ecdysone ligand to the ecdysone receptor ligand binding domain, floral meristem identity gene product activity is increased, thereby promoting early reproductive development in the transgenic seed plant. Similarly, the invention provides, for example, a method of promoting early reproductive development in a seed plant by introducing into the seed plant a nucleic acid molecule encoding a chimeric protein, which comprises a nucleic acid molecule encoding AP1, CAL, LFY, SEP1, SEP2, SEP3, AGL20, AGL22, AGL24 or AGL27 linked in frame to a nucleic acid molecule encoding a glucocorticoid receptor ligand binding domain, to produce a transgenic seed plant, where, under appropriate conditions, the chimeric protein is expressed; and contacting the transgenic seed plant with glucocorticoid ligand, where, upon binding of the glucocorticoid ligand to the glucocorticoid receptor ligand binding domain, floral meristem identity gene product activity is increased, thereby promoting early reproductive development in the transgenic seed plant.

As used herein, the term "ligand" means a naturally occurring or synthetic chemical or biological molecule such as a simple or complex organic molecule, a peptide, a protein or an oligonucleotide that specifically binds a ligand binding domain. In the methods of the present invention, a ligand can be used alone or in solution or can be used in conjunction with an acceptable carrier that can serve to stabilize the ligand or promote absorption of the ligand by a seed plant. If desired, a transgenic seed plant of the invention can be contacted with a ligand for increasing floral meristem identity gene product activity in combination with an unrelated molecule such as a plant nutrient, pesticide or insecticide. When used in reference to a particular ligand binding domain, the term "cognate ligand" means a ligand that, under suitable conditions, specifically binds the particular ligand binding domain.

One skilled in the art readily can determine the optimum concentration of cognate ligand needed to bind a ligand binding domain and increase floral meristem identity gene product activity in a transgenic seed plant of the invention. Generally, a concentration of about 1 nM to 10 µM cognate ligand is useful for increasing floral meristem identity gene product activity in a transgenic seed plant expressing a chimeric protein of the invention. Preferably, a concentration of about 100 nM to 1 µM cognate ligand is useful for increasing floral meristem identity gene product activity in a transgenic seed plant containing a chimeric protein of the invention (see, for example, Christopherson et al., *Proc. Natl. Acad. Sci. USA* 89:6314-6318 (1992), which is incorporated herein by reference; also, see Lloyd et al., supra, 1994). For example, a concentration of about 100 nM to 1 µM dexamethasone can be useful for increasing floral meristem identity gene product activity in a transgenic seed plant of the invention containing a nucleic acid molecule encoding a chimeric protein, which comprises a nucleic acid molecule encoding a floral meristem identity gene product, such as AP1, CAL, LFY, SEP1, SEP2, SEP3, AGL20, AGL22, AGL24 or AGL27 linked in frame to a nucleic acid molecule encoding a glucocorticoid receptor ligand binding domain.

As discussed above, a transgenic seed plant of the invention, such as a transgenic seed plant expressing a chimeric protein of the invention, can be contacted in a variety of manners. A transgenic seed plant can be contacted with cognate ligand, for example, by spraying the seed plant with a gaseous ligand or with solution such as an aqueous solution containing the appropriate ligand; or by adding the cognate ligand to the water supply of a seed plant grown using irrigation or grown hydroponically; or by adding the cognate ligand to the soil or other solid nutrient medium in which a seed plant is grown, whereby the cognate ligand is absorbed into the seed plant to increase floral meristem identity gene product activity. A transgenic seed plant expressing a chimeric protein of the invention also can be contacted with a cognate ligand in aerosol form. In addition, a transgenic seed plant can be contacted with cognate ligand by injecting the seed plant or by immersing the seed plant in a solution containing the cognate ligand.

A transgenic seed plant expressing a chimeric protein of the invention can be contacted individually with cognate ligand, or a group of transgenic seed plants can be contacted en masse to increase floral meristem gene product activity synchronously in all seed plants of the group. Furthermore, a variety of means can be used to contact a transgenic seed plant of the invention with cognate ligand to increase floral meristem identity gene product activity. A transgenic seed plant can be contacted with cognate ligand using, for example, a hand held spraying apparatus; conventional yard "sprinkler"; mechanical spraying system, such as an overhead spraying system in a green house; traditional farm machinery, or "crop dusting." As discussed above in regard to the application of inducing agents, the methods of the invention can be practiced using these and other manual or mechanical means to contact a transgenic seed plant with single or multiple applications of cognate ligand.

IX. Nucleic Acid Molecules of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as a floral organ, and a cDNA library which contains the gene transcript of interest is prepared from the mRNA. Alternatively, cDNA may be prepared from mRNA extracted from other tissues in which genes of the invention or homologs are expressed.

The cDNA or genomic library can then be screened using a probe based upon the sequence of a cloned nucleic acid disclosed here. Probes may be used to hybridize with genomic DNA or cDNA sequences to isolate homologous genes in the same or different plant species. Alternatively, antibodies raised against an polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the nucleic acid of the invention directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990). Appropriate primers and probes for identifying sequences from plant tissues are generated from comparisons of the sequences provided here with other related genes.

The present invention also provides novel substantially purified nucleic acid molecules encoding gene products including AP1, CAL, LFY, SEP1, SEP2, SEP3, AGL20, AGL22, AGL24, and AGL27. For example, the invention provides a substantially purified nucleic acid molecule encoding *Brassica oleracea* AP1 having the amino acid sequence SEQ ID NO:4; a substantially purified nucleic acid molecule encoding *Brassica oleracea* var. *botrytis* AP1 having the amino acid sequence SEQ ID NO:6; or a substantially purified nucleic acid molecule encoding *Zea mays* AP1 having the amino acid sequence SEQ ID NO: 8. In addition, the invention provides a substantially purified nucleic acid molecule that encodes a *Brassica oleracea* AP1, *Brassica oleracea* var. *botrytis* AP1 or *Zea mays* AP1 and that contains additional 5' or 3' noncoding sequence. For example, a substantially purified nucleic acid molecule having a nucleotide sequence such as SEQ ID NO:3, SEQ ID NO:5 or SEQ ID NO:7 is provided.

The invention also provides a substantially purified nucleic acid molecule encoding a CAULIFLOWER gene product such as *Arabidopsis thaliana* CAL SEQ ID NO:10) or *Brassica oleracea* CAL SEQ ID NO:12). The invention also provides nucleic acid molecules encoding SEP1 (SEQ ID NO:28), SEP2 (SEQ ID NO:30), SEP3 (SEQ ID NO:32), AGL20(SEQ ID NO:34), AGL22 (SEQ ID NO:36), AGL24 (SEQ ID NO:38) or AGL27 SEQ ID NO:40 or 41).

As used herein in reference to a particular nucleic acid molecule or gene product, the term "substantially purified" means that the particular nucleic acid molecule or gene product is in a form that is relatively free from contaminating lipids, unrelated gene products, unrelated nucleic acids or other cellular material normally associated with the particular nucleic acid molecule or gene product in a cell.

The present invention also provides a nucleotide sequence having at least ten contiguous nucleotides of a nucleic acid molecule encoding any of the above-referenced gene products, including *Brassica oleracea* AP1, *Brassica oleracea* var. *botrytis* AP1 or *Zea mays* AP1, provided that said nucleotide sequence is not present in a nucleic acid molecule encoding a MADS domain containing protein. For example, such a nucleotide sequence can have at least ten contiguous nucleotides of a nucleic acid molecule encoding an AP1 gene product having the amino acid sequence of SEQ ID NO: 4, SEQ ID NO: 6 or SEQ ID NO: 8. A nucleotide sequence of the invention can have, for example, at least ten contiguous nucleotides of the nucleic acid sequence of SEQ ID NO: 3, SEQ ID NO: 5 or SEQ ID NO: 7.

As used herein, the term "contiguous," as used in reference to the nucleotides of a nucleic acid molecule means that the nucleotides of the nucleic acid molecule follow continuously in sequence. Thus, a nucleotide sequence of the invention has at least ten contiguous nucleotides of one of the recited nucleic acid molecules without any extraneous intervening nucleotides.

Explicitly excluded from a nucleotide sequence of the present invention is a nucleotide sequence having at least ten contiguous nucleotides that is present in a nucleic acid molecule encoding a MADS domain containing protein. MADS domain containing proteins are well known in the art as described in Purugganan et al., supra, 1995.

In general, a nucleotide sequence of the invention can range in size from about 10 nucleotides to the full-length of a cDNA. Such a nucleotide sequence can be chemically synthesized, using routine methods or can be purchased from a commercial source. In addition, such a nucleotide sequence can be obtained by enzymatic methods such as random priming methods, polymerase chain reaction (PCR) methods or by standard restriction endonuclease digestion, followed by denaturation (Sambrook et al., supra, 1989).

A nucleotide sequence of the invention can be useful, for example, as a primer for PCR (Innis et al. (ed.) *PCR Protocols: A Guide to Methods and Applications*, San Diego, Calif.: Academic Press, Inc. (1990)). Such a nucleotide sequence generally contains from about 10 to about 50 nucleotides.

A nucleotide sequence of the invention also can be useful in screening a cDNA or genomic library to obtain a related nucleotide sequence. For example, a cDNA library that is prepared from rice or wheat can be screened with a nucleotide sequence having at least ten contiguous nucleotides of the nucleic acid molecule encoding *Zea mays* AP1 (SEQ ID NO: 7) in order to isolate a rice or wheat ortholog of AP1. Generally, a nucleotide sequence useful for screening a cDNA or genomic library contains at least about 14 to 16 contiguous nucleotides depending, for example, on the hybridization conditions to be used. A nucleotide sequence containing at least 18 to 20 nucleotides, or containing at least 21 to 25 nucleotides, also can be useful.

A nucleotide sequence having at least ten contiguous nucleotides of a nucleic acid molecule encoding *Zea mays* AP1 (SEQ ID NO: 7) also can be used to screen a *Zea mays* cDNA library to isolate a sequence that is related to but distinct from AP1. Similarly, a nucleotide sequence having at least ten contiguous nucleotides of a nucleic acid molecule encoding *Brassica oleracea* AP1 (SEQ ID NO: 3) or a nucleotide sequence having at least ten contiguous nucleotides of a nucleic acid molecule encoding *Brassica oleracea* var. *botrytis* AP1 (SEQ ID NO: 5) can be used to screen a *Brassica oleracea* or *Brassica oleracea* var. *botrytis* cDNA library to isolate a novel sequence that is related to but distinct from AP1. Other gene orthologs, such as of SEP1, SEP2, SEP3, AGL20, AGL22, AGL24 or AGL27 can be isolated by similar methods. In addition, a nucleotide sequence of the invention can be useful in analyzing RNA levels or patterns of expression, as by northern blotting or by in situ hybridization to a tissue section. Such a nucleotide sequence also can be used in Southern blot analysis to evaluate gene structure and identify the presence of related gene sequences.

The invention also provides a vector containing a nucleic acid molecule as described above, e.g., encoding a *Brassica oleracea* AP1 gene product, *Brassica oleracea* var. *botrytis* AP1 gene product or *Zea mays* AP1 gene product. A vector can be a cloning vector or an expression vector and provides a means to transfer an exogenous nucleic acid molecule into a host cell, which can be a prokaryotic or eukaryotic cell. Such vectors are well known and include plasmids, phage vectors and viral vectors. Various vectors and methods for introducing such vectors into a cell are described, for example, by Sambrook et al., supra, 1989, and by Glick and Thompson, supra, 1993).

The invention further provides a method of producing one of the above-described gene products by expressing a nucleic acid molecule encoding the gene product (e.g., AP1, CAL, SEP1, SEP2, SEP3, AGL20, AGL22, AGL24, or AGL27). Thus, for example, a *Brassica oleracea* AP1 gene product can be produced according to a method of the invention by expressing a nucleic acid molecule having the amino acid sequence of SEQ ID NO: 4 or by expressing a nucleic acid molecule having the nucleic acid sequence of SEQ ID NO: 3. Similarly, a *Brassica oleracea* var. *botrytis* AP1 gene product can be produced according to a method of the invention by expressing a nucleic acid molecule having the amino acid sequence of SEQ ID NO: 6 or by expressing a nucleic acid molecule having the nucleic acid sequence of SEQ ID NO: 5. A *Zea mays* AP1 gene product can be produced by expressing a nucleic acid molecule having the amino acid sequence of SEQ ID NO: 8 or by expressing a nucleic acid molecule having the nucleic acid sequence of SEQ ID NO: 7.

The invention also provides a substantially purified AP1 gene product, such as a substantially purified gene product of th invention such as a *Brassica oleracea* AP1 gene product having amino acid sequence SEQ ID NO: 4; a substantially purified *Brassica oleracea* var. *botrytis* AP1 gene product having amino acid sequence SEQ ID NO: 6; or a substantially purified *Zea mays* AP1 gene product having amino acid sequence SEQ ID NO: 8. As used herein, the term "gene product" is used in its broadest sense and includes proteins, polypeptides and peptides, which are related in that each consists of a sequence of amino acids joined by peptide bonds. For convenience, the terms "gene product," "protein" and "polypeptide" are used interchangeably. While no specific attempt is made to distinguish the size limitations of a protein and a peptide, one skilled in the art would understand that proteins generally consist of at least about 50 to 100 amino acids and that peptides generally consist of at least two amino acids up to a few dozen amino acids. The term gene product as used herein includes any such amino acid sequence.

An active fragment of a floral meristem identity gene product also can be useful in the methods of the invention. As used herein, the term "active fragment," means a polypeptide portion of a floral meristem identity gene product that can convert shoot meristem to floral meristem in an angiosperm. An active fragment of an AP1 gene product can consist, for example, of an amino acid sequence that is derived from SEQ ID NO: 2, SEQ ID NO: 4, SEQ ID NO: 6 or SEQ ID NO: 8 and has activity in converting shoot meristem to floral meristem in an angiosperm. An active fragment can be, for example, an amino terminal, carboxyl terminal or internal fragment of *Zea mays* AP1 (SEQ ID NO: 8) that has activity in converting shoot meristem to floral meristem in an angiosperm. The skilled artisan will recognize that an active fragment of a floral meristem identity gene product, as defined herein, can be useful in the methods of the invention for converting shoot meristem to floral meristem in an angiosperm, for producing early reproductive development in a seed plant, or for producing reproductive sterility in a seed plant.

Such an active fragment can be produced using well known recombinant DNA methods (Sambrook et al., supra, 1989). Similarly, an active fragment can be, for example, an amino terminal, carboxyl terminal or internal fragment of *Arabidopsis thaliana* CAL SEQ ID NO: 10) or *Brassica oleracea* CAL SEQ ID NO: 12) that has activity, for example, in converting shoot meristem to floral meristem in an angiosperm. The product of the BobCAL gene SEQ ID NO:14), which is truncated at amino acid 150, lacks activity in converting shoot meristem to floral meristem and, therefore, is an example of a polypeptide portion of a CAL floral meristem identity gene product that is not an "active fragment" of a floral meristem identity gene product.

An active fragment of a floral meristem identity gene product, which can convert shoot meristem to floral meristem in an angiosperm, can be identified using the methods described in WO 97/46078. Briefly, an angiosperm such as *Arabidopsis* can be transformed with a nucleic acid molecule encoding a portion of a floral meristem identity gene product in order to determine whether the portion can convert shoot meristem to floral meristem and, therefore, is an active fragment of a floral meristem identity gene product.

The invention also provides an expression vector containing a nucleic acid molecule encoding a floral meristem identity gene product such as SEP3, AGL20, AGL22, AGL24, AGL27, AP1, CAL or LFY operably linked to a heterologous regulatory element. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence.

As used herein, the term "heterologous regulatory element" means a regulatory element derived from a different gene than the gene encoding the floral meristem identity gene product to which it is operably linked. A vector containing a floral meristem identity gene, however, contains a nucleic acid molecule encoding a floral meristem identity gene product operably linked to a homolgous regulatory element. Such a vector does not contain a nucleic acid molecule encoding a floral meristem identity gene product operably linked to a heterologous regulatory element and, thus, is not an expression vector of the invention.

The invention further provides a plant expression vector containing a floral meristem identity gene product operably linked to a heterologous regulatory element. For example, a plant expression vector containing a nucleic acid molecule encoding an AP1 gene product having at least about 70 percent amino acid identity with an amino acid sequence of *Arabidopsis thaliana* AP1 (SEQ ID NO: 2) in the region from amino acid 1 to amino acid 163 or with the amino acid sequence of *Zea mays* AP1 (SEQ ID NO: 8) in the region from amino acid 1 to amino acid 163 is provided. A plant expression vector containing a floral meristem identity gene product operably linked to a constitutive regulatory element, such as the cauliflower mosaic virus 35S promoter, is provided. In addition, a plant expression vector containing a floral meristem identity gene product operably linked to an inducible regulatory element is provided.

A useful plant expression vector can contain a constitutive regulatory element for expression of an exogenous nucleic acid molecule in all or most tissues of a seed plant. The use of a constitutive regulatory element can be particularly advantageous because expression from the element is relatively independent of developmentally regulated or tissue-specific factors. For example, the cauliflower mosaic virus 35S promoter (CaMV 35S) is a well-characterized constitutive regulatory element that produces a high level of expression in all plant tissues (Odell et al., *Nature* 313:810-812 (1985), which is incorporated herein by reference). Furthermore, the CaMV 35S promoter can be particularly useful due to its activity in numerous different seed plant species (Benfey and Chua, *Science* 250:959-966 (1990), which is incorporated herein by reference; Odell et al., supra, 1985). Other constitutive regulatory elements useful for expression in a seed plant include, for example, the cauliflower mosaic virus 19S promoter; the Figwort mosaic virus promoter (Singer et al., *Plant Mol. Biol.* 14:433 (1990), which is incorporated herein by reference); and the nopaline synthase (nos) gene promoter (An, *Plant Physiol.* 81:86 (1986), which is incorporated herein by reference).

In addition, an expression vector of the invention can contain a regulated gene regulatory element such as a promoter or enhancer element. A particularly useful regulated promoter is a tissue-specific promoter such as the shoot meristem-specific CDC2 promoter (Hemerly et al., *Plant Cell* 5:1711-1723 (1993), which is incorporated herein by reference), or the AGL8 promoter, which is active in the apical shoot meristem immediately after the transition to flowering (Mandel and Yanofsky, supra, 1995). The promoter of the SHOOTMERISTEMLESS gene, which is expressed exclusively in the shoot meristem beginning within an embryo and throughout the angiosperm life cycle, also can be a particularly useful tissue-specific gene regulatory element (see Long et al., *Nature* 379:66-69 (1996), which is incorporated herein by reference).

An appropriate regulatory element such as a promoter is selected depending on the desired pattern or level of expression of a nucleic acid molecule linked thereto. For example, a constitutive promoter, which is active in all tissues, would be appropriate if expression of a gene product in all plant tissues is desired. In addition, a developmentally regulated or tissue-specific regulatory element can be useful to direct floral meristem identity gene expression to specific tissues, for example. As discussed above, inducible expression also can be particularly useful to manipulate the timing of gene expression such that, for example, a population of transgenic seed plants of the invention that contain an expression vector comprising a floral meristem identity gene linked to an inducible regulatory element can undergo early reproductive development at essentially the same time. Selecting the time of reproductive development can be useful, for example, in manipulating the time of crop harvest.

Using nucleic acid molecules encoding gene products provided herein, the skilled artisan can isolate, if desired, novel orthologs. For example, one would choose a region of AP1 that is highly conserved among known AP1 sequences such as a region that is highly conserved between *Arabidopsis* AP1 (SEQ ID NO: 1) and *Zea mays* AP1 (GenBank accession number L46400; SEQ ID NO: 7) to screen a cDNA or genomic library of interest for a novel AP1 ortholog. One can use a full-length *Arabidopsis* AP1 (SEQ ID NO: 1), for example, to isolate a novel ortholog of AP1 (see, e.g., Example V of WO 97/46078). If desired, the region encoding the MADS domain, which is common to a number of genes, can be excluded, from the sequence used as a probe. Similarly, the skilled artisan knows that a nucleic acid molecule encoding a full-length CAL cDNA such as *Arabidopsis* CAL (SEQ ID NO: 9) or *Brassica oleracea* CAL (SEQ ID NO: 11) can be useful in isolating a novel CAL ortholog.

For example, the *Arabidopsis* AP1 cDNA (SEQ ID NO: 1) can be used as a probe to identify and isolate a novel AP1 ortholog. Using a nucleotide sequence derived from a conserved region of SEQ ID NO: 1, SEQ ID NO: 3, SEQ ID NO: 5 or SEQ ID NO: 7, for example, a nucleic acid molecule encoding a novel AP1 ortholog can be isolated from other plant species. Using methods such as those described by Purugganan et al., supra, 1995, one can readily confirm that the newly isolated molecule is an AP1 ortholog. Thus, a nucleic acid molecule encoding an AP1 gene product, which has at least about 70 percent amino acid identity with the amino acid sequence of SEQ ID NO: 2 (*Arabidopsis* AP1) in the region from amino acid 1 to amino acid 163 or with the amino acid sequence of SEQ ID NO: 8 (*Zea mays* AP1) in the region from amino acid 1 to amino acid 163 can be isolated and identified using well known methods.

Similarly, in order to isolate an ortholog of CAL, one can choose a region of CAL that is highly conserved among known CAL cDNAs, such as a region conserved between *Arabidopsis* CAL (SEQ ID NO: 9) and *Brassica oleracea* CAL (SEQ ID NO: 11). The *Arabidopsis* CAL cDNA (SEQ ID NO: 9) or *Brassica oleracea* CAL cDNA (SEQ ID NO: 11), or a nucleotide fragment thereof, can be used to identify and isolate a novel CAL ortholog using methods such as those described in Example V of WO 97/46078. In order to identify related MADS domain genes, a nucleotide sequence derived from the MADS domain of AP1 or CAL, for example, can be useful to isolate a related gene sequence encoding this DNA-binding motif.

Hybridization conditions for isolating a gene ortholog, for example, are relatively stringent such that non-specific hybridization is minimized. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook, supra, 1989).

The invention also provides a kit for converting shoot meristem to floral meristem in an angiosperm, which contains a plant expression vector having a nucleic acid molecule encoding a floral meristem identity gene product. A kit for promoting early reproductive development in a seed plant, which contains a plant expression vector having a nucleic acid molecule encoding a floral meristem identity gene product, also is provided. If desired, such kits can contain appropriate reagents to facilitate high efficiency transformation of a seed plant with a plant expression vector of the invention. Furthermore, if desired, a control vector lacking a floral meristem identity gene can be included in the kits to determine, for example, the efficiency of transformation.

The following example is offered by way of example, not limitation.

EXAMPLES

Example 1

This example shows the identification of proteins that interact with CAL.

Proteins that Interact with CAL

Yeast two-hybrid screens were performed to identify candidate genes whose products interact with AP1 and CAL. The two-hybrid library screens were performed in the YPB2 strain [MATa ara3 his3 ade2 lys2 trp1 leu2, 112 can$^r$ gal4 gal80 LYS2::GAL1-HIS3, URA3::(GAL1$_{UAS}$17mers)-lacZ]. Yeast were transformed using a modified version of the lithium acetate method of Schiestl and Gietz, *Curr. Genet.* 16, 339-346 (1989).

The two-hybrid cDNA expression library was constructed in the pBI771 (prey) vector using tissue of whole plants at different stages. The bait constructs were prepared by inserting the intact CAL coding region and a truncated form of AP1 into the pBI-880 vector (a variant of pPC62 described in Chevray and Nathans *Proc. Natl. Acad. Sci USA* 5789-5793 (1992); Kohalmi et al., *Plant. Mol. Biol. Man. M*1, 1-30 (1998)) by inserting the corresponding coding region in-frame at the 3' end of the GAL4 (1-147) sequence contained in the centromere LEU2 plasmid. These baits tested negative for the ability to activate transcription of both reporters, alone as well as in combination with each the prey vector and an inert control prey, the *Arabidopsis* cruciferin seed storage protein.

SEP3K, SOC1K, SVPK, AGL24K and SOC1KC/2 were generated by polymerase chain reaction (PCR) from the relevant cDNAs using oligos with the appropriate restriction site for posterior cloning into pBI771. The following primers were used (SEQ ID NOS:51-59):

SEP3-5'K:   5'-CCGTCGACCCATGAGCCAGCAGGAGTATCTC-3'

SEP3-3'Kbox: 5'-CCGCGGCCGCCTTACTCTGAAGATCGTT-3'

-continued

```
SOC1-5'K:     5'-CCGTCGACCCATGAAATATGAAGCAGCAAAC-3'
SOC1-3'Kbox:  5'-CCGCGGCCGCCTCCTTTTGCTTGAGCTG-3'
SOC1-C/2:     5'-CCGCGGCCGCACTTTCTTGATTCTTATT-3'
SVP-5'K:      5'-CCGTCGACCCATGAGTGATCACGCCCGAATG-3'
SVP-3'Kbox:   5'-CCGCGGCCGCTCCCTTTTTCTGAAGTTC-3'
AGL24-5'K:    5'-CCGTCGACCCATGCTTGAGAATTGTAACCTC-3'
AGL24-3'Kbox: 5'-CCGCGGCCGCCTCAAGTGAGAAAATTTG-3'
```

The PCR products were subcloned directly into pCRII (invitrogen) and then digested with SalI-NotI for next subcloning into pBI-771. All constructs were confirmed by sequencing.

CAL screen: The frequency of clones which activated both the HIS3 and lacZ reporters from the 30° C. plates was $1/(1.8\times10^6)=5.6\times10^{-7}$. The frequency on the 23° C. plates was $22/(1.8\times10^6)=1.2\times10^{-5}$.

AP1 screen: $9.2\times10^4$ total transformants were screened at 23° C. and the frequency of clones activating both reporter genes was $1.5\times10^{-4}$.

The transformants were selected on supplemented synthetic dextrose medium lacking leucine, tryptophan and histidine but containing 5 mM 3-amino-1,2,4-triazole. The colonies growing on this selective medium were assayed for β-galactosidase activity on nitrocellulose filters (Kohalmi et al., supra). Plasmid DNA from positive clones was isolated and transform into E. coli.

Using a full-length CAL cDNA as bait, 23 interacting clones were identified, rescued from yeast and transformed into E. coli. Sequence analyses showed that they fell into four classes, all previously identified as AGAMOUS-like (AGL) genes.

The first class, SEP3, included four clones, all of which began within the I-region. Because the cDNA library was poly (T) primed, the clones all comprised varying lengths of the 3' end of the gene. SEP3 is first expressed in the central dome of stage-two floral primordia and is maintained in the inner three whorls of the flower (Mandel and Yanofsky, Sex. Plant Reprod. 11, 22-28 (1998)). SEP3 acts redundantly with SEP1 and SEP2 and is necessary for the development of petals, stamens and carpels (Pelaz et al., Current Biology 11, 182-184 (2000)).

The second class identified was the SUPPRESSOR OF CO OVEREXPRESSION 1 (SOC1) gene and included seven clones. The starting point of these clones varied. One clone began with the ATG start codon, another started near the end of the MADS-box, and the remaining clones started at 5' ends of the I-region. SOC1 is expressed in the inflorescence meristem, as well as in the two inner whorls of the flower beginning in late stage-two and it is involved in promoting flowering (Samach et al., Science 288, 1613-1616 (2000)).

The third class was the SHORT VEGETATIVE PHASE (SVP) gene, and included four clones. Of the clones from this screen, one started in the MADS-box, and three began in the I-region. SVP was identified as an Arabidopsis expressed sequence tag with homology to the MADS-box family (Alvarez-Buylla et al., Plant J. 24, 457-466 (2000)), and it was also cloned by (Hartman et al., 2000) through transposon tagging. SVP is a repressor of flowering and is expressed in young leaves and throughout the shoot apical meristem during vegetative development. After the transition to flowering, it is expressed in young flower primordia until stage 3 (Hartman et al., Plant J. 21, 351-360 (2000)).

The last eight clones were identified as AGL24. One of these clones began within the MADS-box and three within the I-region. In addition, the 5' ends of four clones lie in the first third of the K-box, representing the shortest clones isolated in the screen. AGL24 was first identified in a previous yeast two-hybrid screen as a clone which interacts with AG (Alvarez-Buylla et al., Proc. Natl. Acad. Sci. USA 97, 5328-5333 (2000)). AGL24 is expressed in inflorescences and young floral primordia.

To confirm the specificity of the observed interactions, the longest and shortest clone of each class was transformed back into a yeast strain that contained either the CAL bait, the bait vector, or an inert control bait, cruciferin. The strains containing the CAL bait tested positive for both B-Gal activity and HIS prototrophy. The strains containing the bait vector or the cruciferin bait were negative in both assays, as they were not able to grow on plates lacking histidine and the yeast colonies were completely white in the B-Gal assay.

AP1 Forms Dimers in Yeast with CAL Interactors

The structural and functional similarities between CAL and AP1 suggested that they may interact with an overlapping set of proteins. In order to explore this possibility, we constructed an AP1 bait by inserting the intact AP1 coding region into the pBI-880 vector. As in the Finley and Brent system, the full-length AP1 bait activated transcription independently. To overcome this problem, a deletion construct was made encoding residues 1-196 of AP1 (AP1Δ1), thus eliminating the putative trans-activating C-terminus. In contrast to the full-length AP1 clone, the deletion derivative did not activate the reporter on its own. The longest clone of each class was transformed into yeast in combination with the AP1 deletion bait. In every case, both of the reporters were strongly activated, suggesting that all four CAL-interacting proteins also interact with AP1.

Domain for Protein-Protein Interactions

Previous studies have shown that the MADS-domain and I regions may be important for homodimer formation by AG and by AP1 (Krizek and Meyerowitz, 1996; Mizukami et al., 1996; Riechmann et al., 1996) and that the I region and K-domain are needed for the formation of AP3/PI heterodimers (Krizek and Meyerowitz, Proc. Natl. Acad. Sci. USA 93, 4063-4070 (1996); Riechmann et al., Proc. Natl. Acad. Sci. USA 93, 4793-4798 (1996)). In addition, the K-domain of AG is sufficient to promote interactions with SEP1, SEP2, SEP3 and AGL6 in yeast (Fan et al., Plant J. 11, 999-1010 (1997)). Since many of the CAL- and AP1-interacting clones isolated as part of our study lacked the MADS-domain and I regions, we tested if the K-domain itself was sufficient to promote the observed interactions. First, we subcloned the K-box regions of SEP3, SOC1, SVP and AGL24 into the prey vector, and tested their ability to activate the reporter using either the empty bait or the cruciferin gene cloned into the bait plasmid. As expected, these K-box regions did not activate the reporter. In contrast, when these K-box prey constructs were introduced into yeast strains that contained each of the CAL or AP1 bait plasmids, reporter activity significantly above background levels was consistently observed. Furthermore, the addition of approximately half of the C-terminal domain of the SOC1 protein was sufficient to greatly strengthen the interaction, similar to what has previously been shown to occur for AG and its interactors (Fan et al., supra). Taken together, these studies suggest that the ability of CAL and AP1 to interact with SEP3, SOC1, SVP, and AGL24 is largely mediated by the K-domain. However, other protein domains appear to enhance these interactions since the level of reporter gene activation is higher when larger constructs are used.

Example 2

This example shows the indetifications of proteins that interact with AP1.

Proteins that Interact with AP1

In order to find additional proteins that could interact with AP1, the library was screened with the truncated AP1 bait (1-196), and 13 clones that tested positive for β-Gal activity were characterized. As expected, we found three clones of AGL20 (also known as SOC1), five clones of AGL22 (also known as SVP), and one clone of AGL24.

In addition we found one clone of a new MADS box gene designated AGL27 (Alvarez-Buylla et al., supra), two different clones encoding a putative RNA binding protein (GI 10178188), and one clone encoding a novel protein (GI 3157943). We determined that these three newly isolated genes have overlapping expression patterns with that of AP1, consistent with the idea that they may interact with AP1 in planta.

To confirm the specificity of these interactions, the longest clone of each class was transformed back into yeast with the AP1 bait, the bait vector, and an inert control bait, cruciferin. The strains containing the AP1 bait tested positive for both β-Gal activity and HIS prototrophy. The strains containing the bait vector or the cruciferin bait were negative in both assays. We then tested if the three new AP1-interacting clones could also interact with CAL, since they had not been isolated in the CAL library screen. However, AGL27, the RNA binding protein, and the novel protein were unable to interact with CAL in yeast.

Example 3

This example demonstrates the characteriztion of sep3 mutants.

sep3 Mutants Resemble Intermediate Alleles of AP1

As a start toward determining if the observed interactions in yeast reflect functional interactions in vivo, we characterized loss- and gain-of-function alleles of SEP3. If some of the activities of AP1 require an interaction with SEP3, then mutations in SEP3 might be expected to resemble mutant alleles of AP1. We recently identified two independently derived En-1 transposon insertion alleles of SEP3 and have described the phenotype of sep1 sep2 sep3 triple mutants in which the three inner whorls of organs become sepaloid (Pelaz et al., supra).

The flowers of sep3-1 and sep3-2 single mutant plants have petals that are partially transformed into sepals, and infrequently, axillary flowers develop at the base of the first-whorl sepals. When examined by scanning electronic microscopy (SEM), the abaxial cells of these transformed petals resemble cells that are a mixture of abaxial wild type sepal and abaxial wild type petal cells. The abaxial side of the wild type sepals have rectangular cells of varying size, some of which are very long, reaching 300 μm in length. These long cells can be more than ten times the length of the smallest sepal cells. Numerous stomata are visible throughout wild type sepals but are never found on wild-type petals. Cells on the abaxial side of wild type petals all have a uniformly small rounded appearance, and are typically about half of the size of the smallest sepal cells. Unlike wild type petals that have rounded cells, the abaxial side of the sep3 petals consists of rectangular cells, resembling those found on sepals. Although these mutant petal cells are larger than their wild type counterparts, they are still smaller than the wild type sepal cells. Interestingly, several stomata are interspersed on the surface of these petals, further suggesting a partial transformation of these petals into sepals.

Because the sep3 petal phenotype resembles that observed for intermediate alleles of ap1, (Bowman et al., *Development* 119, 721-743 (1993)), we compared second whorl organs of sep3 mutants to those of intermediate alleles of ap1, including ap1-2, ap1-4 and ap1-6. The abaxial cells of these ap1 mutant petals are very similar to those of the sep3 mutants, and consist of a blend between petal and sepal cells. These ap1 mutant cells are larger and more elongated than the wild type petal cells but they do not reach the length of the longer wild type sepal cells. As was observed for sep3 mutants, petals of these intermediate alleles of ap1 develop several stomata, further indicating the sepal-like identity. The similarities of sep and ap1 mutants are consistent with the idea that some of the activities of AP1 are compromised in sep mutants, consistent with the possible loss of AP1/SEP interactions.

If the interaction between SEP and AP1 is necessary for AP1 activity, then a reduction in SEP expression would be predicted to produce some or all of the ap1-mutant phenotypes. To test this idea, we generated transgenic antisense lines in which the 5' end of the SEP3 gene was expressed in the antisense orientation from the double 35S promoter. Two independent transgenic lines (SP70.1 and SP70.2) were tested for reduction in the amount of SEP3 mRNA accumulation. As expected, the amount of SEP3 mRNA in these antisense lines was reduced in comparison to the wild type. The resulting lines underexpressing SEP3 showed green petals whose cells appeared partially transformed into sepal cells. These plants also occasionally had axillary flowers arising from the base of the first-whorl sepals. These phenotypes are consistent with a reduction in AP1 activity, as intermediate alleles of ap1 produce similar phenotypes. This activity reduction does not mean less AP1 transcription, the levels of mRNA in these antisense lines are comparable to those of wild type flowers. Interestingly, the green-petal phenotype of these SEP3 antisense lines is more extreme than that observed for sep3 single mutants, based on the color change, suggesting that the SEP3 transgene may also have down regulated other closely related genes such as SEP1 and SEP2.

Example 4

This example demonstrates the characterization of plants overexpressing SEP3.

Constitutive Expression of SEP3

Previous studies have demonstrated that constitutive expression of AP1 (35S::AP1) results in plants that flower considerably earlier than wild type plants (Mandel and Yanofsky, supra). If some of the activities of AP1 require an interaction with SEP3, as the loss of function studies above would indicate, then it might be expected that constitutive SEP3 expression would further enhance the 35S::AP1 early-flowering phenotype. To test this hypothesis and to provide further evidence that SEP3 interacts with AP1 in planta, we generated 35S::SEP3 sense lines that express constitutively SEP3 throughout the plant.

Construction of the 35S::SEP3 construct was as follows: cDNA was isolated by RT-PCR using the oligos OAM37:

5'-TAGAAACATCATCTTAAAAAT-3'(SEQ ID NO:60) and SEP3-5': 5'-CCGGATCCAAAATGGGAAGAGG-GAGA-3'(SEQ ID NO:61). This cDNA was first cloned into pCRII (invitrogen) and then digested with BamHI for insertion into the BamHI site of pCGN18 (which contains 35S promoter) to produce sense lines, and confirmed by sequencing. The cDNA cloned into pCRII was digested with BamHI and BglII, the 363bp band corresponding to the 5' end of the cDNA was cloned in antisense orientation into the BamHI site of pBIIN-JIT (plasmid carrying two 35S promoters in tandem). The 355::SEP3 sense and antisense constructs were introduced into Arabidopsis, ecotype Columbia, by vacuum infiltration (Bechtold et al., *C. R. Acad. Sci.* 316, 1194-1199 (1993)) and transgenic plants were selected on Kanamycin plates.

35S::SEP3 transgenic plants are early flowering, and bolt after producing only four or five rosette leaves, in contrast to wild-type plants which bolt after producing approximately ten leaves under these growth conditions. In addition to the early-flowering phenotype, 35S::SEP3 plants have curled rosette leaves as well as two or three very curled cauline leaves, each of which typically subtends a solitary flower. The primary inflorescence usually produces only a few flowers before terminating. Some of the phenotypes caused by ectopic SEP3 expression are similar to those conferred by ectopic expression of several other MADS-box genes. However ectopic expression of these other genes often produces additional phenotypes, including alterations in flower organ identity and fruit development that are not seen in the 35S::SEP3 plants.

Example 5

This example demonstrates genetic interactions between 35S::SEP3 and 35S::AP1 transgenes.

To provide genetic evidence that SEP3 and AP1 interact, we crossed the 35S::SEP3 transgene into 35S::AP1 plants. Whereas 35S::AP1 plants flower early after producing four to five rosette leaves, 35S::AP135S::SEP3 doubly transgenic plants flower after producing only two rosette leaves, often developing a terminal flower directly from the rosette. Occasionally, these plants produce a very short inflorescence with two cauline leaves that subtend solitary flowers, a terminal flower at the apex, and very little internode elongation. The strong enhancement of the early-flowering phenotypes conferred by each single transgene is consistent with the suggestion that AP1 and SEP3 interact in planta.

We also used another genetic approach to investigate the interaction between SEP3 and AP1, avoiding the use of two different transgenic lines. We took advantage of the tfl1 mutant, in which AP1 is ectopically activated (Bowman et al., supra; Gustafson-Brown et al., *Cell* 76, 131-143 (1994)), producing a phenotype that closely resembles the 35S::AP1 phenotype. As expected, the tfl mutation in combination with the 35S::SEP3 transgene produces the same phenotypes as observed for plants carrying both 35S::AP1 and 35S::SEP3 transgenes. These plants flower after forming two rosette leaves and produce abbreviated shoots with very short internodes and a terminal flower.

Example 6

This example demonstrates the flowering time of an agl24 mutant.

The effect of AGL22 (also known as SVP) and AGL24 loss-of-function mutations was assessed. An agl24 T-DNA insertional mutant (designated W24.2) and an agl22 mutant (designated svp-E) were obtained and the time to flowering of the mutant plants was measured and compared to wild-type Columbia *Arabidopsis* plants. On average, the agl24 mutant produced almost twice as many leaves before flowering than wildtype plants. In addition, the agl22 mutant produced only half the number of leaves as wildtype before flowering. Results of the experiment, shown in number of leaves prior to flowering, is provided below.

|  | Rosette | Cauline | Total | N |
| --- | --- | --- | --- | --- |
| Columbia | 11 +/− 0.9 | 2.9 +/− 0.5 | 14 +/− 1.1 | 26 |
| svp-E | 6 +/− 0.6 | 2.8 +/− 0.4 | 9 +/− 0.6 | 25 |
| W24.2 | 19 +/− 1.5 | 3.1 +/− 0.5 | 22 +/− 1.7 | 26 |

Thus, the time to flowering and the amount of vegetative growth of the agl24 mutant was increased compared to wild type plants and the time to flowering and the amount of vegetative growth of the agl22 mutant was decreased compared to wild type plants.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A non-naturally occurring seed plant, the plant comprising: a first ectopically expressed polynucleotide encoding an APETALA1 gene product exhibiting at least 90% sequence identity to SEQ ID NO:2 and having transcriptional activation activity; and a second ectopically expressed nucleic acid molecule encoding SEPALLATA1 (SEP1) gene product exhibiting at least 90% sequence identity to SEQ ID NO:28 and having transcriptional activation activity, wherein the plant is characterized by early reproductive development compared to a plant lacking the first and second ectopically expressed polynucleotides.

2. The non-naturally occurring seed plant of claim 1, wherein expression of the first ectopically expressed polynucleotide is increased in a tissue of a plant compared to a wild type plant.

3. The non-naturally occurring seed plant of claim 1, wherein expression of the second ectopically expressed polynucleotide is increased in a tissue of a plant compared to a wild type plant.

4. The non-naturally occurring seed plant of claim 1, wherein the non-naturally occurring seed plant is a transgenic plant comprising a first exogenous gene regulatory element operably linked to the first ectopically expressible polynucleotide and a second exogenous gene regulatory element operably linked to the second ectopically expressible polynucleotide.

5. The non-naturally occurring seed plant of claim 1, wherein the first ectopically expressed polynucleotide encodes SEQ ID NO:2.

6. The non-naturally occurring seed plant of claim 1, wherein the second ectopically expressed polynucleotide encodes a SEP1 gene product comprising SEQ ID NO:28.

7. A method of decreasing the time period to the initiation of reproductive development in a plant, the method comprising, ectopically expressing a first polynucleotide encoding an APETALA1 gene product exhibiting at least 90% sequence identity to SEQ ID NO:2 and having transcriptional activation activity and ectopically expressing a second nucleic acid molecule encoding a SEPALLATA1 gene product exhibiting at least 90% sequence identity to SEQ lID NO:28 and having transcriptional activation activity, thereby producing a plant with a decreased time period to the initiation of reproductive development compared to a plant lacking the first and second ectopically expressed polynucleotides.

8. The method of claim 7 comprising, introducing a first ectopically expressed nucleic acid molecule comprising a first polynucleotide encoding SEQ ID NO:2; and introducing a second ectopically expressed nucleic acid molecule comprising a second polynucleotide encoding SEQ ID NO:28.

9. The method of claim 8, wherein the first and second ectopically expressed nucleic acid molecules each comprise a gene regulatory element operably linked to the first and second polynucleotides.

10. The method of claim 8, wherein expression of the first ectopically expressed polynucleotide is increased in a tissue of the plant compared to a wildtype plant.

11. The method of claim 8, wherein expression of the second ectopically expressed polynucleotide is increased in a tissue of the plant compared to a wildtype plant.

12. The method of claim 9, wherein the gene regulatory element is constitutive.

13. The method of claim 9, wherein the gene regulatory element is inducible.

14. The method of claim 9, wherein the gene regulatory element is tissue-specific.

15. The method of claim 7, wherein the first ectopically expressed polynucleotide encodes SEQ ID NO:2.

16. The method of claim 7, wherein the second ectopically expressed polynucleotide is a SEPALLATA1 gene product comprising SEQ ID NO:28.

* * * * *

SEQUENCE LISTING

```
<160> NUMBER OF SEQ ID NOS: 61

<210> SEQ ID NO 1
<211> LENGTH: 1057
<212> TYPE: DNA
<213> ORGANISM: Arabidopsis thaliana
<220> FEATURE:
<221> NAME/KEY: CDS
<222> LOCATION: (124)..(894)
<223> OTHER INFORMATION: APETALA1 (AP1)

<400> SEQUENCE: 1
ctttccaatt ggttcatacc aaagtctgag ctcttcttta tatctctctt gtagtttctt      60
attgggggtc tttgtttttgt ttggttcttt tagagtaaga agtttcttaa aaaaggatca    120
```

```
aaa atg gga agg ggt agg gtt caa ttg aag agg ata gag aac aag atc      168
    Met Gly Arg Gly Arg Val Gln Leu Lys Arg Ile Glu Asn Lys Ile
     1               5                  10                  15 aat aga caa gtg aca ttc tcg aaa aga aga gct ggt ctt ttg aag aaa      216
Asn Arg Gln Val Thr Phe Ser Lys Arg Arg Ala Gly Leu Leu Lys Lys
                 20                  25                  30 gct cat gag atc tct gtt ctc tgt gat gct gaa gtt gct ctt gtt gtc      264
Ala His Glu Ile Ser Val Leu Cys Asp Ala Glu Val Ala Leu Val Val
             35                  40                  45 ttc tcc cat aag ggg aaa ctc ttc gaa tac tcc act gat tct tgt atg      312
Phe Ser His Lys Gly Lys Leu Phe Glu Tyr Ser Thr Asp Ser Cys Met
         50                  55                  60 gag aag ata ctt gaa cgc tat gag agg tac tct tac gcc gaa aga cag      360
Glu Lys Ile Leu Glu Arg Tyr Glu Arg Tyr Ser Tyr Ala Glu Arg Gln
     65                  70                  75 ctt att gca cct gag tcc gac gtc aat aca aac tgg tcg atg gag tat      408
Leu Ile Ala Pro Glu Ser Asp Val Asn Thr Asn Trp Ser Met Glu Tyr
 80                  85                  90                  95 aac agg ctt aag gct aag att gag ctt ttg gag aga aac cag agg cat      456
Asn Arg Leu Lys Ala Lys Ile Glu Leu Leu Glu Arg Asn Gln Arg His
                100                 105                 110 tat ctt ggg gaa gac ttg caa gca atg agc cct aaa gag ctt cag aat      504
Tyr Leu Gly Glu Asp Leu Gln Ala Met Ser Pro Lys Glu Leu Gln Asn
            115                 120                 125 ctg gag cag cag ctt gac act gct ctt aag cac atc cgc act aga aaa      552
Leu Glu Gln Gln Leu Asp Thr Ala Leu Lys His Ile Arg Thr Arg Lys
        130                 135                 140 aac caa ctt atg tac gag tcc atc aat gag ctc caa aaa aag gag aag      600
Asn Gln Leu Met Tyr Glu Ser Ile Asn Glu Leu Gln Lys Lys Glu Lys
145                 150                 155 gcc ata cag gag caa aac agc atg ctt tct aaa cag atc aag gag agg      648
Ala Ile Gln Glu Gln Asn Ser Met Leu Ser Lys Gln Ile Lys Glu Arg
160                 165                 170                 175 gaa aaa att ctt agg gct caa cag gag cag tgg gat cag cag aac caa      696
Glu Lys Ile Leu Arg Ala Gln Gln Glu Gln Trp Asp Gln Gln Asn Gln
                180                 185                 190 ggc cac aat atg cct ccc cct ctg cca ccg cag cag cac caa atc cag      744
Gly His Asn Met Pro Pro Pro Leu Pro Pro Gln Gln His Gln Ile Gln
            195                 200                 205 cat cct tac atg ctc tct cat cag cca tct cct ttt ctc aac atg ggt      792
His Pro Tyr Met Leu Ser His Gln Pro Ser Pro Phe Leu Asn Met Gly
        210                 215                 220 ggt ctg tat caa gaa gat gat cca atg gca atg agg agg aat gat ctc      840
Gly Leu Tyr Gln Glu Asp Asp Pro Met Ala Met Arg Arg Asn Asp Leu
225                 230                 235 gaa ctg act ctt gaa ccc gtt tac aac tgc aac ctt ggc tgc ttc gcc      888
Glu Leu Thr Leu Glu Pro Val Tyr Asn Cys Asn Leu Gly Cys Phe Ala
240                 245                 250                 255 gca tga agcatttcca tatatatatt tgtaatcgtc aacaataaaa acagtttgcc       944
Ala acatacatat aaatagtggc taggctcttt tcatccaatt aatatatttt ggcaaatgtt   1004
cgatgttctt atatcatcat ataaaatta gcaggctcct ttcttttttt gta           1057
```

<210> SEQ ID NO 2
<211> LENGTH: 256
<212> TYPE: PRT
<213> ORGANISM: Arabidopsis thaliana
<220> FEATURE:
<223> OTHER INFORMATION: APETALA1 (AP1)

<400> SEQUENCE: 2

| | | | | | | | | | | | | | | |
|---|---|---|---|---|---|---|---|---|---|---|---|---|---|---|
|Met|Gly|Arg|Gly|Arg|Val|Gln|Leu|Lys|Arg|Ile|Glu|Asn|Lys|Ile|Asn|
|1| | | |5| | | | |10| | | | |15| |

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Asn Gln Gly
            180                 185                 190

His Asn Met Pro Pro Leu Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255

<210> SEQ ID NO 3
<211> LENGTH: 794
<212> TYPE: DNA
<213> ORGANISM: Brassica oleracea
<220> FEATURE:
<221> NAME/KEY: CDS
<222> LOCATION: (36)..(794)
<223> OTHER INFORMATION: APETALA1 (AP1)

<400> SEQUENCE: 3

```
tcttagagga aatagttcct ttaaaaggga taaaa atg gga agg ggt agg gtt     53
                                     Met Gly Arg Gly Arg Val
                                       1               5 cag ttg aag agg ata gaa aac aag atc aat aga caa gtg aca ttc tcg    101
Gln Leu Lys Arg Ile Glu Asn Lys Ile Asn Arg Gln Val Thr Phe Ser
         10                  15                  20 aaa aga aga gct ggt ctt atg aag aaa gct cat gag atc tct gtt ctg    149
Lys Arg Arg Ala Gly Leu Met Lys Lys Ala His Glu Ile Ser Val Leu
     25                  30                  35 tgt gat gct gaa gtt gcg ctt gtt gtc ttc tcc cat aag ggg aaa ctc    197
Cys Asp Ala Glu Val Ala Leu Val Val Phe Ser His Lys Gly Lys Leu
 40                  45                  50
```

-continued

```
ttt gaa tac tcc act gat tct tgt atg gag aag ata ctt gaa cgc tat      245
Phe Glu Tyr Ser Thr Asp Ser Cys Met Glu Lys Ile Leu Glu Arg Tyr
 55                  60                  65                  70 gag aga tac tct tac gcc gag aga cag ctt ata gca cct gag tcc gac      293
Glu Arg Tyr Ser Tyr Ala Glu Arg Gln Leu Ile Ala Pro Glu Ser Asp
                 75                  80                  85 tcc aat acg aac tgg tcg atg gag tat aat agg ctt aag gct aag att      341
Ser Asn Thr Asn Trp Ser Met Glu Tyr Asn Arg Leu Lys Ala Lys Ile
             90                  95                 100 gag ctt ttg gag aga aac cag agg cac tat ctt ggg gaa gac ttg caa      389
Glu Leu Leu Glu Arg Asn Gln Arg His Tyr Leu Gly Glu Asp Leu Gln
         105                 110                 115 gca atg agc cct aag gaa ctc cag aat cta gag caa cag ctt gat act      437
Ala Met Ser Pro Lys Glu Leu Gln Asn Leu Glu Gln Gln Leu Asp Thr
     120                 125                 130 gct ctt aag cac atc cgc tct aga aaa aac caa ctt atg tac gac tcc      485
Ala Leu Lys His Ile Arg Ser Arg Lys Asn Gln Leu Met Tyr Asp Ser
135                 140                 145                 150 atc aat gag ctc caa aga aag gag aaa gcc ata cag gaa caa aac agc      533
Ile Asn Glu Leu Gln Arg Lys Glu Lys Ala Ile Gln Glu Gln Asn Ser
                155                 160                 165 atg ctt tcc aag cag att aag gag agg gaa aac gtt ctt agg gcg caa      581
Met Leu Ser Lys Gln Ile Lys Glu Arg Glu Asn Val Leu Arg Ala Gln
            170                 175                 180 caa gag caa tgg gac gag cag aac cat ggc cat aat atg cct ccg cct      629
Gln Glu Gln Trp Asp Glu Gln Asn His Gly His Asn Met Pro Pro Pro
        185                 190                 195 cca ccc ccg cag cag cat caa atc cag cat cct tac atg ctc tct cat      677
Pro Pro Pro Gln Gln His Gln Ile Gln His Pro Tyr Met Leu Ser His
    200                 205                 210 cag cca tct cct ttt ctc aac atg ggg ggc tg tat caa gaa gaa gat      725
Gln Pro Ser Pro Phe Leu Asn Met Gly Gly Leu Tyr Gln Glu Glu Asp
215                 220                 225                 230 caa atg gca atg agg agg aac gat ctc gat ctg tct ctt gaa ccc ggt      773
Gln Met Ala Met Arg Arg Asn Asp Leu Asp Leu Ser Leu Glu Pro Gly
                235                 240                 245 tat aac tgc aat ctc ggc tgc                                          794
Tyr Asn Cys Asn Leu Gly Cys
            250
```

<210> SEQ ID NO 4
<211> LENGTH: 253
<212> TYPE: PRT
<213> ORGANISM: Brassica oleracea
<220> FEATURE:
<223> OTHER INFORMATION: APETALA1 (AP1)

<400> SEQUENCE: 4

```
Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Met Lys Lys Ala
                 20                  25                  30

His Glu Ile Ser Val Leu Cys Asp Ala Glu Val Ala Leu Val Val Phe
             35                  40                  45

Ser His Lys Gly Lys Leu Phe Glu Tyr Ser Thr Asp Ser Cys Met Glu
         50                  55                  60

Lys Ile Leu Glu Arg Tyr Glu Arg Tyr Ser Tyr Ala Glu Arg Gln Leu
 65                  70                  75                  80

Ile Ala Pro Glu Ser Asp Ser Asn Thr Asn Trp Ser Met Glu Tyr Asn
                 85                  90                  95
```

-continued

```
Arg Leu Lys Ala Lys Ile Glu Leu Leu Glu Arg Asn Gln Arg His Tyr
                100                 105                 110
Leu Gly Glu Asp Leu Gln Ala Met Ser Pro Lys Glu Leu Gln Asn Leu
            115                 120                 125
Glu Gln Gln Leu Asp Thr Ala Leu Lys His Ile Arg Ser Arg Lys Asn
        130                 135                 140
Gln Leu Met Tyr Asp Ser Ile Asn Glu Leu Gln Arg Lys Glu Lys Ala
145                 150                 155                 160
Ile Gln Glu Gln Asn Ser Met Leu Ser Lys Gln Ile Lys Glu Arg Glu
                165                 170                 175
Asn Val Leu Arg Ala Gln Gln Glu Gln Trp Asp Gln Asn His Gly
            180                 185                 190
His Asn Met Pro Pro Pro Pro Gln Gln His Gln Ile Gln His
        195                 200                 205
Pro Tyr Met Leu Ser His Gln Pro Ser Pro Phe Leu Asn Met Gly Gly
    210                 215                 220
Leu Tyr Gln Glu Glu Asp Gln Met Ala Met Arg Arg Asn Asp Leu Asp
225                 230                 235                 240
Leu Ser Leu Glu Pro Gly Tyr Asn Cys Asn Leu Gly Cys
                245                 250
```

<210> SEQ ID NO 5
<211> LENGTH: 768
<212> TYPE: DNA
<213> ORGANISM: Brassica oleracea var. botrytis
<220> FEATURE:
<221> NAME/KEY: CDS
<222> LOCATION: (1)..(768)
<223> OTHER INFORMATION: APETALA1 (AP1)

<400> SEQUENCE: 5

```
atg gga agg ggt agg gtt cag ttg aag agg ata gaa aac aag atc aat        48
Met Gly Arg Gly Arg Val Gln Leu Lys Arg Ile Glu Asn Lys Ile Asn
  1               5                  10                  15 aga caa gtg aca ttc tcg aaa aga aga gct ggt ctt atg aag aaa gct        96
Arg Gln Val Thr Phe Ser Lys Arg Arg Ala Gly Leu Met Lys Lys Ala
                 20                  25                  30 cat gag atc tct gtt ctg tgt gat gct gaa gtt gcg ctt gtt gtc ttc       144
His Glu Ile Ser Val Leu Cys Asp Ala Glu Val Ala Leu Val Val Phe
             35                  40                  45 tcc cat aag ggg aaa ctc ttt gaa tac ccc act gat tct tgt atg gag       192
Ser His Lys Gly Lys Leu Phe Glu Tyr Pro Thr Asp Ser Cys Met Glu
         50                  55                  60 gag ata ctt gaa cgc tat gag aga tac tct tac gcc gag aga cag ctt       240
Glu Ile Leu Glu Arg Tyr Glu Arg Tyr Ser Tyr Ala Glu Arg Gln Leu
     65                  70                  75                  80 ata gca cct gag tcc gac tcc aat acg aac tgg tcg atg gag tat aat       288
Ile Ala Pro Glu Ser Asp Ser Asn Thr Asn Trp Ser Met Glu Tyr Asn
                 85                  90                  95 agg ctt aag gct aag att gag ctt ttg gag aga aac cag agg cac tat       336
Arg Leu Lys Ala Lys Ile Glu Leu Leu Glu Arg Asn Gln Arg His Tyr
                100                 105                 110 ctt ggg gaa gac ttg caa gca atg agc cct aag gaa ctc cag aat cta       384
Leu Gly Glu Asp Leu Gln Ala Met Ser Pro Lys Glu Leu Gln Asn Leu
            115                 120                 125 gag caa cag ctt gat act gct ctt aag cac atc cgc tct aga aaa aac       432
Glu Gln Gln Leu Asp Thr Ala Leu Lys His Ile Arg Ser Arg Lys Asn
        130                 135                 140
```

```
caa ctt atg tac gac tcc atc aat gag ctc caa aga aag gag aaa gcc   480
Gln Leu Met Tyr Asp Ser Ile Asn Glu Leu Gln Arg Lys Glu Lys Ala
145                 150                 155                 160 ata cag gaa caa aac agc atg ctt tcc aag cag att aag gag agg gaa   528
Ile Gln Glu Gln Asn Ser Met Leu Ser Lys Gln Ile Lys Glu Arg Glu
                165                 170                 175 aac gtt ctt agg gcg caa caa gag caa tgg gac gag cag aac cat ggc   576
Asn Val Leu Arg Ala Gln Gln Glu Gln Trp Asp Glu Gln Asn His Gly
            180                 185                 190 cat aat atg cct ccg cct cca ccc ccg cag cag cat caa atc cag cat   624
His Asn Met Pro Pro Pro Pro Pro Pro Gln Gln His Gln Ile Gln His
        195                 200                 205 cct tac atg ctc tct cat cag cca tct cct ttt ctc aac atg gga ggg   672
Pro Tyr Met Leu Ser His Gln Pro Ser Pro Phe Leu Asn Met Gly Gly
    210                 215                 220 ctg tat caa gaa gaa gat caa atg gca atg agg agg aac gat ctc gat   720
Leu Tyr Gln Glu Glu Asp Gln Met Ala Met Arg Arg Asn Asp Leu Asp
225                 230                 235                 240 ctg tct ctt gaa ccc gtt tac aac tgc aac ctt ggc cgt cgc tgc tga   768
Leu Ser Leu Glu Pro Val Tyr Asn Cys Asn Leu Gly Arg Arg Cys
                245                 250                 255
```

<210> SEQ ID NO 6
<211> LENGTH: 255
<212> TYPE: PRT
<213> ORGANISM: Brassica oleracea var. botrytis
<220> FEATURE:
<223> OTHER INFORMATION: APETALA1 (AP1)

<400> SEQUENCE: 6

```
Met Gly Arg Gly Arg Val Gln Leu Lys Arg Ile Glu Asn Lys Ile Asn
1               5                   10                  15

Arg Gln Val Thr Phe Ser Lys Arg Arg Ala Gly Leu Met Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Pro Thr Asp Ser Cys Met Glu
    50                  55                  60

Glu Ile Leu Glu Arg Tyr Glu Arg Tyr Ser Tyr Ala Glu Arg Gln Leu
65                  70                  75                  80

Ile Ala Pro Glu Ser Asp Ser Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Ser Arg Lys Asn
    130                 135                 140

Gln Leu Met Tyr Asp Ser Ile Asn Glu Leu Gln Arg Lys Glu Lys Ala
145                 150                 155                 160

Ile Gln Glu Gln Asn Ser Met Leu Ser Lys Gln Ile Lys Glu Arg Glu
                165                 170                 175

Asn Val Leu Arg Ala Gln Gln Glu Gln Trp Asp Glu Gln Asn His Gly
            180                 185                 190

His Asn Met Pro Pro Pro Pro Pro Pro Gln Gln His Gln Ile Gln His
        195                 200                 205

Pro Tyr Met Leu Ser His Gln Pro Ser Pro Phe Leu Asn Met Gly Gly
    210                 215                 220
```

```
Leu Tyr Gln Glu Glu Asp Gln Met Ala Met Arg Arg Asn Asp Leu Asp
225                 230                 235                 240

Leu Ser Leu Glu Pro Val Tyr Asn Cys Asn Leu Gly Arg Arg Cys
            245                 250                 255

<210> SEQ ID NO 7
<211> LENGTH: 1345
<212> TYPE: DNA
<213> ORGANISM: Zea mays
<220> FEATURE:
<221> NAME/KEY: CDS
<222> LOCATION: (149)..(970)
<223> OTHER INFORMATION: APETALA1 (AP1)

<400> SEQUENCE: 7
gcacgagtcc tcctcctcct cgcatcccac cccaccccac cttctcctta aagctacctg      60 cctaccggc ggttgcgcgc cgcaatcgat cgaccggaag agaaagagca gctagctagc      120
tagcagatcg gagcacggca acaaggcg atg ggg cgc ggc aag gta cag ctg        172
                               Met Gly Arg Gly Lys Val Gln Leu
                                 1               5 aag cgg ata gag aac aag ata aac cgg cag gtg acc ttc tcc aag cgc       220
Lys Arg Ile Glu Asn Lys Ile Asn Arg Gln Val Thr Phe Ser Lys Arg
         10                  15                  20 cgg aac ggc ctg ctc aag aag gcg cac gag atc tcc gtc ctc tgc gat       268
Arg Asn Gly Leu Leu Lys Lys Ala His Glu Ile Ser Val Leu Cys Asp
 25                  30                  35                  40 gcc gag gtc gcc gtc atc gtc ttc tcc ccc aag ggc aag ctc tac gag       316
Ala Glu Val Ala Val Ile Val Phe Ser Pro Lys Gly Lys Leu Tyr Glu
                 45                  50                  55 tac gcc acc gac tcc cgc atg gac aaa att ctt gaa cgc tat gag cga       364
Tyr Ala Thr Asp Ser Arg Met Asp Lys Ile Leu Glu Arg Tyr Glu Arg
             60                  65                  70 tat tcc tat gct gaa aag gct ctt att tca gct gaa tct gaa agt gag       412
Tyr Ser Tyr Ala Glu Lys Ala Leu Ile Ser Ala Glu Ser Glu Ser Glu
         75                  80                  85 gga aat tgg tgc cac gaa tac agg aaa ctg aag gcc aaa att gag acc       460
Gly Asn Trp Cys His Glu Tyr Arg Lys Leu Lys Ala Lys Ile Glu Thr
 90                  95                 100 ata caa aaa tgc cac aag cac ctg atg gga gag gat cta gag tct ttg       508
Ile Gln Lys Cys His Lys His Leu Met Gly Glu Asp Leu Glu Ser Leu
105                 110                 115                 120 aat ccc aaa gag ctc cag caa cta gag cag cag ctg gat agc tca ctg       556
Asn Pro Lys Glu Leu Gln Gln Leu Glu Gln Gln Leu Asp Ser Ser Leu
                125                 130                 135 aag cac atc aga tca agg aag agc cac ctt atg gcc gag tct att tct       604
Lys His Ile Arg Ser Arg Lys Ser His Leu Met Ala Glu Ser Ile Ser
            140                 145                 150 gag cta cag aag aag gag agg tca ctg cag gag gag aac aag gct ctg       652
Glu Leu Gln Lys Lys Glu Arg Ser Leu Gln Glu Glu Asn Lys Ala Leu
        155                 160                 165 cag aag gaa ctt gcg gag agg cag aag gcc gtc gcg agc cgg cag cag       700
Gln Lys Glu Leu Ala Glu Arg Gln Lys Ala Val Ala Ser Arg Gln Gln
    170                 175                 180 cag caa cag cag cag gtg cag tgg gac cag cag aca cat gcc cag gcc       748
Gln Gln Gln Gln Gln Val Gln Trp Asp Gln Gln Thr His Ala Gln Ala
185                 190                 195                 200 cag aca agc tca tca tcg tcc tcc ttc atg atg agg cag gat cag cag       796
Gln Thr Ser Ser Ser Ser Ser Phe Met Met Arg Gln Asp Gln Gln
                205                 210                 215
```

-continued

```
gga ctg ccg cct cca cac aac atc tgc ttc ccg ccg ttg aca atg gga    844
Gly Leu Pro Pro Pro His Asn Ile Cys Phe Pro Pro Leu Thr Met Gly
        220                 225                 230 gat aga ggt gaa gag ctg gct gcg gcg gcg gcg cag cag cag cag        892
Asp Arg Gly Glu Glu Leu Ala Ala Ala Ala Ala Gln Gln Gln Gln
    235                 240                 245 cca ctg ccg ggg cag gcg caa ccg cag ctc cgc atc gca ggt ctg cca    940
Pro Leu Pro Gly Gln Ala Gln Pro Gln Leu Arg Ile Ala Gly Leu Pro
250                 255                 260 cca tgg atg ctg agc cac ctc aat gca taa ggagagggtc gatgaacaca      990
Pro Trp Met Leu Ser His Leu Asn Ala
265                 270 tcgacctcct ctctctctct ctctcgtcat ggatcatgac gtacgcgtac catatggttg  1050
ctgtgcctgc ccccatcgat cgcgagcaat ggcacgctca tgcaagtgat cattgctccc  1110
cgttggttaa accctagcct atgttcatgg cgtcagcaac taagctaaac tattgttatg  1170
tttgcaagaa agggtaaacc cgctagcgtg taatcttgt ccagctatca gtatgcttgt   1230
tactgcccag ttaccttga atctagcggc gcttttggtg agagggtgca gtttactta    1290 aacatggttc gtgacttgct gtaaatagta gtattaatcg atttgggcat ctaaa       1345
```

<210> SEQ ID NO 8
<211> LENGTH: 273
<212> TYPE: PRT
<213> ORGANISM: Zea mays
<220> FEATURE:
<223> OTHER INFORMATION: APETALA1 (AP1)

<400> SEQUENCE: 8

```
Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Asp Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ala Leu Gln Lys Glu Leu Ala Glu Arg Gln
                165                 170                 175

Lys Ala Val Ala Ser Arg Gln Gln Gln Gln Gln Gln Val Gln Trp
            180                 185                 190

Asp Gln Gln Thr His Ala Gln Ala Gln Thr Ser Ser Ser Ser Ser
        195                 200                 205

Phe Met Met Arg Gln Asp Gln Gln Gly Leu Pro Pro Pro His Asn Ile
    210                 215                 220
```

```
Cys Phe Pro Pro Leu Thr Met Gly Asp Arg Gly Glu Leu Ala Ala
225                 230                 235                 240

Ala Ala Ala Ala Gln Gln Gln Pro Leu Pro Gly Gln Ala Gln Pro
                245                 250                 255

Gln Leu Arg Ile Ala Gly Leu Pro Pro Trp Met Leu Ser His Leu Asn
            260                 265                 270

Ala

<210> SEQ ID NO 9
<211> LENGTH: 779
<212> TYPE: DNA
<213> ORGANISM: Arabidopsis thaliana
<220> FEATURE:
<221> NAME/KEY: CDS
<222> LOCATION: (10)..(777)
<223> OTHER INFORMATION: CAULIFLOWER (CAL)
<220> FEATURE:
<221> NAME/KEY: modified_base
<222> LOCATION: (778)..(779)
<223> OTHER INFORMATION: n = g, a, c or t

<400> SEQUENCE: 9 ttaagagaa atg gga agg ggt agg gtt gaa ttg aag agg ata gag aac aag      51
          Met Gly Arg Gly Arg Val Glu Leu Lys Arg Ile Glu Asn Lys
          1               5                   10 atc aat aga caa gtg aca ttc tcg aaa aga aga act ggt ctt ttg aag       99
Ile Asn Arg Gln Val Thr Phe Ser Lys Arg Arg Thr Gly Leu Leu Lys
 15                  20                  25                  30 aaa gct cag gag atc tct gtt ctt tgt gat gcc gag gtt tcc ctt att     147
Lys Ala Gln Glu Ile Ser Val Leu Cys Asp Ala Glu Val Ser Leu Ile
                 35                  40                  45 gtc ttc tcc cat aag ggc aaa ttg ttc gag tac tcc tct gaa tct tgc     195
Val Phe Ser His Lys Gly Lys Leu Phe Glu Tyr Ser Ser Glu Ser Cys
         50                  55                  60 atg gag aag gta cta gaa cgc tac gag agg tat tct tac gcc gag aga     243
Met Glu Lys Val Leu Glu Arg Tyr Glu Arg Tyr Ser Tyr Ala Glu Arg
     65                  70                  75 cag ctg att gca cct gac tct cac gtt aat gca cag acg aac tgg tca     291
Gln Leu Ile Ala Pro Asp Ser His Val Asn Ala Gln Thr Asn Trp Ser
 80                  85                  90 atg gag tat agc agg ctt aag gcc aag att gag ctt ttg gag aga aac     339
Met Glu Tyr Ser Arg Leu Lys Ala Lys Ile Glu Leu Leu Glu Arg Asn
 95                 100                 105                 110 caa agg cat tat ctg gga gaa gag ttg gaa cca atg agc ctc aag gat     387
Gln Arg His Tyr Leu Gly Glu Glu Leu Glu Pro Met Ser Leu Lys Asp
                115                 120                 125 ctc caa aat ctg gag cag cag ctt gag act gct ctt aag cac att cgc     435
Leu Gln Asn Leu Glu Gln Gln Leu Glu Thr Ala Leu Lys His Ile Arg
            130                 135                 140 tcc aga aaa aat caa ctc atg aat gag tcc ctc aac cac ctc caa aga     483
Ser Arg Lys Asn Gln Leu Met Asn Glu Ser Leu Asn His Leu Gln Arg
        145                 150                 155 aag gag aag gag ata cag gag gaa aac agc atg ctt acc aaa cag ata     531
Lys Glu Lys Glu Ile Gln Glu Glu Asn Ser Met Leu Thr Lys Gln Ile
    160                 165                 170 aag gag agg gaa aac atc cta aag aca aaa caa acc caa tgt gag cag     579
Lys Glu Arg Glu Asn Ile Leu Lys Thr Lys Gln Thr Gln Cys Glu Gln
175                 180                 185                 190 ctg aac cgc agc gtc gac gat gta cca cag cca caa cca ttt caa cac     627
Leu Asn Arg Ser Val Asp Asp Val Pro Gln Pro Gln Pro Phe Gln His
                195                 200                 205
```

-continued

```
ccc cat ctt tac atg atc gct cat cag act tct cct ttc cta aat atg      675
Pro His Leu Tyr Met Ile Ala His Gln Thr Ser Pro Phe Leu Asn Met
        210                 215                 220 ggt ggt ttg tac caa gga gaa gac caa acg gcg atg agg agg aac aat      723
Gly Gly Leu Tyr Gln Gly Glu Asp Gln Thr Ala Met Arg Arg Asn Asn
225                 230                 235 ctg gat ctg act ctt gaa ccc att tac aat tac ctt ggc tgt tac gcc      771
Leu Asp Leu Thr Leu Glu Pro Ile Tyr Asn Tyr Leu Gly Cys Tyr Ala
240                 245                 250 gct tga nn                                                           779
Ala
255
```

<210> SEQ ID NO 10
<211> LENGTH: 255
<212> TYPE: PRT
<213> ORGANISM: Arabidopsis thaliana
<220> FEATURE:
<223> OTHER INFORMATION: CAULIFLOWER (CAL)

<400> SEQUENCE: 10

```
Met Gly Arg Gly Arg Val Glu Leu Lys Arg Ile Glu Asn Lys Ile Asn
 1               5                  10                  15

Arg Gln Val Thr Phe Ser Lys Arg Arg Thr Gly Leu Leu Lys Lys Ala
                20                  25                  30

Gln Glu Ile Ser Val Leu Cys Asp Ala Glu Val Ser Leu Ile Val Phe
            35                  40                  45

Ser His Lys Gly Lys Leu Phe Glu Tyr Ser Ser Glu Ser Cys Met Glu
        50                  55                  60

Lys Val Leu Glu Arg Tyr Glu Arg Tyr Ser Tyr Ala Glu Arg Gln Leu
65                  70                  75                  80

Ile Ala Pro Asp Ser His Val Asn Ala Gln Thr Asn Trp Ser Met Glu
                85                  90                  95

Tyr Ser Arg Leu Lys Ala Lys Ile Glu Leu Leu Glu Arg Asn Gln Arg
                100                 105                 110

His Tyr Leu Gly Glu Glu Leu Glu Pro Met Ser Leu Lys Asp Leu Gln
            115                 120                 125

Asn Leu Glu Gln Gln Leu Glu Thr Ala Leu Lys His Ile Arg Ser Arg
        130                 135                 140

Lys Asn Gln Leu Met Asn Glu Ser Leu Asn His Leu Gln Arg Lys Glu
145                 150                 155                 160

Lys Glu Ile Gln Glu Asn Ser Met Leu Thr Lys Gln Ile Lys Glu
                165                 170                 175

Arg Glu Asn Ile Leu Lys Thr Lys Gln Thr Gln Cys Glu Gln Leu Asn
                180                 185                 190

Arg Ser Val Asp Asp Val Pro Gln Pro Gln Pro Phe Gln His Pro His
            195                 200                 205

Leu Tyr Met Ile Ala His Gln Thr Ser Pro Phe Leu Asn Met Gly Gly
        210                 215                 220

Leu Tyr Gln Gly Glu Asp Gln Thr Ala Met Arg Arg Asn Asn Leu Asp
225                 230                 235                 240

Leu Thr Leu Glu Pro Ile Tyr Asn Tyr Leu Gly Cys Tyr Ala Ala
                245                 250                 255
```

<210> SEQ ID NO 11
<211> LENGTH: 756
<212> TYPE: DNA
<213> ORGANISM: Brassica oleracea

```
<220> FEATURE:
<221> NAME/KEY: CDS
<222> LOCATION: (1)..(756)
<223> OTHER INFORMATION: CAULIFLOWER

<400> SEQUENCE: 11 atg gga agg ggt agg gtt gaa atg aag agg ata gag aac aag atc aac      48
Met Gly Arg Gly Arg Val Glu Met Lys Arg Ile Glu Asn Lys Ile Asn
 1               5                  10                  15 cga caa gtg acg ttt tcg aaa aga aga gct ggt ctt ttg aag aaa gcc      96
Arg Gln Val Thr Phe Ser Lys Arg Arg Ala Gly Leu Leu Lys Lys Ala
             20                  25                  30 cat gag atc tcg atc ctt tgt gat gct gag gtt tcc ctt att gtc ttc     144
His Glu Ile Ser Ile Leu Cys Asp Ala Glu Val Ser Leu Ile Val Phe
         35                  40                  45 tcc cat aag ggg aaa ctg ttc gag tac tcg tct gaa tct tgc atg gag     192
Ser His Lys Gly Lys Leu Phe Glu Tyr Ser Ser Glu Ser Cys Met Glu
     50                  55                  60 aag gta cta gaa cac tac gag agg tac tct tac gcc gag aaa cag cta     240
Lys Val Leu Glu His Tyr Glu Arg Tyr Ser Tyr Ala Glu Lys Gln Leu
 65                  70                  75                  80 aaa gtt cca gac tct cac gtc aat gca caa acg aac tgg tca gtg gaa     288
Lys Val Pro Asp Ser His Val Asn Ala Gln Thr Asn Trp Ser Val Glu
                 85                  90                  95 tat agc agg ctt aag gct aag att gag ctt ttg gag aga aac caa agg     336
Tyr Ser Arg Leu Lys Ala Lys Ile Glu Leu Leu Glu Arg Asn Gln Arg
            100                 105                 110 cat tat ctg ggc gaa gat tta gaa tca atc agc ata aag gag cta cag     384
His Tyr Leu Gly Glu Asp Leu Glu Ser Ile Ser Ile Lys Glu Leu Gln
        115                 120                 125 aat ctg gag cag cag ctt gac act tct ctt aaa cat att cgc tcg aga     432
Asn Leu Glu Gln Gln Leu Asp Thr Ser Leu Lys His Ile Arg Ser Arg
    130                 135                 140 aaa aat caa cta atg cac gag tcc ctc aac cac ctc caa aga aag gag     480
Lys Asn Gln Leu Met His Glu Ser Leu Asn His Leu Gln Arg Lys Glu
145                 150                 155                 160 aaa gaa ata ctg gag gaa aac agc atg ctt gcc aaa cag ata agg gag     528
Lys Glu Ile Leu Glu Glu Asn Ser Met Leu Ala Lys Gln Ile Arg Glu
                165                 170                 175 agg gag agt atc cta agg aca cat caa aac caa tca gag cag caa aac     576
Arg Glu Ser Ile Leu Arg Thr His Gln Asn Gln Ser Glu Gln Gln Asn
            180                 185                 190 cgc agc cac cat gta gct cct cag ccg caa ccg cag tta aat cct tac     624
Arg Ser His His Val Ala Pro Gln Pro Gln Pro Gln Leu Asn Pro Tyr
        195                 200                 205 atg gca tca tct cct ttc cta aat atg ggt ggc atg tac caa gga gaa     672
Met Ala Ser Ser Pro Phe Leu Asn Met Gly Gly Met Tyr Gln Gly Glu
    210                 215                 220 tat cca acg gcg gtg agg agg aac cgt ctc gat ctg act ctt gaa ccc     720
Tyr Pro Thr Ala Val Arg Arg Asn Arg Leu Asp Leu Thr Leu Glu Pro
225                 230                 235                 240 att tac aac tgc aac ctt ggt tac ttt gcc gca tga                     756
Ile Tyr Asn Cys Asn Leu Gly Tyr Phe Ala Ala
                245                 250

<210> SEQ ID NO 12
<211> LENGTH: 251
<212> TYPE: PRT
<213> ORGANISM: Brassica oleracea
<220> FEATURE:
<223> OTHER INFORMATION: CAULIFLOWER (CAL)
```

-continued

```
<400> SEQUENCE: 12

Met Gly Arg Gly Arg Val Glu Met Lys Arg Ile Glu Asn Lys Ile Asn
 1               5                   10                  15

Arg Gln Val Thr Phe Ser Lys Arg Arg Ala Gly Leu Leu Lys Lys Ala
                20                  25                  30

His Glu Ile Ser Ile Leu Cys Asp Ala Glu Val Ser Leu Ile Val Phe
            35                  40                  45

Ser His Lys Gly Lys Leu Phe Glu Tyr Ser Ser Glu Ser Cys Met Glu
        50                  55                  60

Lys Val Leu Glu His Tyr Glu Arg Tyr Ser Tyr Ala Glu Lys Gln Leu
65                  70                  75                  80

Lys Val Pro Asp Ser His Val Asn Ala Gln Thr Asn Trp Ser Val Glu
                85                  90                  95

Tyr Ser Arg Leu Lys Ala Lys Ile Glu Leu Leu Glu Arg Asn Gln Arg
            100                 105                 110

His Tyr Leu Gly Glu Asp Leu Glu Ser Ile Ser Ile Lys Glu Leu Gln
        115                 120                 125

Asn Leu Glu Gln Gln Leu Asp Thr Ser Leu Lys His Ile Arg Ser Arg
130                 135                 140

Lys Asn Gln Leu Met His Glu Ser Leu Asn His Leu Gln Arg Lys Glu
145                 150                 155                 160

Lys Glu Ile Leu Glu Glu Asn Ser Met Leu Ala Lys Gln Ile Arg Glu
                165                 170                 175

Arg Glu Ser Ile Leu Arg Thr His Gln Asn Gln Ser Glu Gln Gln Asn
            180                 185                 190

Arg Ser His His Val Ala Pro Gln Pro Gln Pro Gln Leu Asn Pro Tyr
        195                 200                 205

Met Ala Ser Ser Pro Phe Leu Asn Met Gly Gly Met Tyr Gln Gly Glu
    210                 215                 220

Tyr Pro Thr Ala Val Arg Arg Asn Arg Leu Asp Leu Thr Leu Glu Pro
225                 230                 235                 240

Ile Tyr Asn Cys Asn Leu Gly Tyr Phe Ala Ala
                245                 250

<210> SEQ ID NO 13
<211> LENGTH: 756
<212> TYPE: DNA
<213> ORGANISM: Brassica oleracea var. botrytis
<220> FEATURE:
<221> NAME/KEY: CDS
<222> LOCATION: (1)..(453)
<223> OTHER INFORMATION: CAULIFLOWER

<400> SEQUENCE: 13 atg gga agg ggt agg gtt gaa atg aag agg ata gag aac aag atc aac      48
Met Gly Arg Gly Arg Val Glu Met Lys Arg Ile Glu Asn Lys Ile Asn
 1               5                   10                  15 aga caa gtg acg ttt tcg aaa aga aga gct ggt ctt ttg aag aaa gcc      96
Arg Gln Val Thr Phe Ser Lys Arg Arg Ala Gly Leu Leu Lys Lys Ala
                20                  25                  30 cat gag atc tcg att ctt tgt gat gct gag gtt tcc ctt att gtc ttc     144
His Glu Ile Ser Ile Leu Cys Asp Ala Glu Val Ser Leu Ile Val Phe
            35                  40                  45 tcc cat aag ggg aaa ctg ttc gag tac tcg tct gaa tct tgc atg gag     192
Ser His Lys Gly Lys Leu Phe Glu Tyr Ser Ser Glu Ser Cys Met Glu
        50                  55                  60 aag gta cta gaa cgc tac gag agg tac tct tac gcc gag aaa cag cta     240
```

```
Lys Val Leu Glu Arg Tyr Glu Arg Tyr Ser Tyr Ala Glu Lys Gln Leu
 65                  70                  75                  80 aaa gct cca gac tct cac gtc aat gca caa acg aac tgg tca atg gaa      288
Lys Ala Pro Asp Ser His Val Asn Ala Gln Thr Asn Trp Ser Met Glu
                 85                  90                  95 tat agc agg ctt aag gct aag att gag ctt tgg gag agg aac caa agg      336
Tyr Ser Arg Leu Lys Ala Lys Ile Glu Leu Trp Glu Arg Asn Gln Arg
            100                 105                 110 cat tat ctg gga gaa gat tta gaa tca atc agc ata aag gag cta cag      384
His Tyr Leu Gly Glu Asp Leu Glu Ser Ile Ser Ile Lys Glu Leu Gln
        115                 120                 125 aat ctg gag cag cag ctt gac act tct ctt aaa cat att cgc tcc aga      432
Asn Leu Glu Gln Gln Leu Asp Thr Ser Leu Lys His Ile Arg Ser Arg
130                 135                 140 aaa aat caa cta atg cac tag tccctcaacc acctccaaag aaaggagaaa         483
Lys Asn Gln Leu Met His
145                 150 gaaatactgg aggaaaacag catgcttgcc aaacagataa aggagaggga gagtatccta    543
aggacacatc aaaccaatc agagcagcaa accgcagcc accatgtagc tcctcagccg      603
caaccgcagt taaatcctta catggcatca tctcctttcc taaatatggg tggcatgtac    663
caaggagaat atccaacggc ggtgaggagg aaccgtctcg atctgactct tgaacccatt    723
tacaactgca accttggtta ctttgccgca tga                                 756

<210> SEQ ID NO 14
<211> LENGTH: 150
<212> TYPE: PRT
<213> ORGANISM: Brassica oleracea var. botrytis
<220> FEATURE:
<223> OTHER INFORMATION: CAULIFLOWER (CAL)

<400> SEQUENCE: 14

Met Gly Arg Gly Arg Val Glu Met Lys Arg Ile Glu Asn Lys Ile Asn
 1               5                  10                  15

Arg Gln Val Thr Phe Ser Lys Arg Arg Ala Gly Leu Leu Lys Lys Ala
                20                  25                  30

His Glu Ile Ser Ile Leu Cys Asp Ala Glu Val Ser Leu Ile Val Phe
            35                  40                  45

Ser His Lys Gly Lys Leu Phe Glu Tyr Ser Ser Glu Ser Cys Met Glu
        50                  55                  60

Lys Val Leu Glu Arg Tyr Glu Arg Tyr Ser Tyr Ala Glu Lys Gln Leu
 65                  70                  75                  80

Lys Ala Pro Asp Ser His Val Asn Ala Gln Thr Asn Trp Ser Met Glu
                 85                  90                  95

Tyr Ser Arg Leu Lys Ala Lys Ile Glu Leu Trp Glu Arg Asn Gln Arg
            100                 105                 110

His Tyr Leu Gly Glu Asp Leu Glu Ser Ile Ser Ile Lys Glu Leu Gln
        115                 120                 125

Asn Leu Glu Gln Gln Leu Asp Thr Ser Leu Lys His Ile Arg Ser Arg
130                 135                 140

Lys Asn Gln Leu Met His
145                 150

<210> SEQ ID NO 15
<211> LENGTH: 1500
<212> TYPE: DNA
<213> ORGANISM: Arabidopsis thaliana
<220> FEATURE:
```

-continued

```
<221> NAME/KEY: CDS
<222> LOCATION: (72)..(1346)
<223> OTHER INFORMATION: LEAFY (LFY)

<400> SEQUENCE: 15
aaagcaatct gctcaaaaga gtaaagaaag agagaaaaag agagtgatag agagagagag      60
aaaaatagat t atg gat cct gaa ggt ttc acg agt ggc tta ttc cgg tgg     110
            Met Asp Pro Glu Gly Phe Thr Ser Gly Leu Phe Arg Trp
              1               5                  10 aac cca acg aga gca ttg gtt caa gca cca cct ccg gtt cca cct ccg     158
Asn Pro Thr Arg Ala Leu Val Gln Ala Pro Pro Pro Val Pro Pro Pro
         15                  20                  25 ctg cag caa cag ccg gtg aca ccg cag acg gct gct ttt ggg atg cga     206
Leu Gln Gln Gln Pro Val Thr Pro Gln Thr Ala Ala Phe Gly Met Arg
 30                  35                  40                  45 ctt ggt ggt tta gag gga cta ttc ggt cca tac ggt ata cgt ttc tac     254
Leu Gly Gly Leu Glu Gly Leu Phe Gly Pro Tyr Gly Ile Arg Phe Tyr
                 50                  55                  60 acg gcg gcg aag ata gcg gag tta ggt ttt acg gcg agc acg ctt gtg     302
Thr Ala Ala Lys Ile Ala Glu Leu Gly Phe Thr Ala Ser Thr Leu Val
             65                  70                  75 ggt atg aag gac gag gag ctt gaa gag atg atg aat agt ctc tct cat     350
Gly Met Lys Asp Glu Glu Leu Glu Glu Met Met Asn Ser Leu Ser His
         80                  85                  90 atc ttt cgt tgg gag ctt ctt gtt ggt gaa cgg tac ggt atc aaa gct     398
Ile Phe Arg Trp Glu Leu Leu Val Gly Glu Arg Tyr Gly Ile Lys Ala
     95                 100                 105 gcc gtt aga gct gaa cgg aga cga ttg caa gaa gag gag gaa gag gaa     446
Ala Val Arg Ala Glu Arg Arg Arg Leu Gln Glu Glu Glu Glu Glu Glu
110                 115                 120                 125 tct tct aga cgc cgt cat ttg cta ctc tcc gcc gct ggt gat tcc ggt     494
Ser Ser Arg Arg Arg His Leu Leu Leu Ser Ala Ala Gly Asp Ser Gly
                130                 135                 140 act cat cac gct ctt gat gct ctc tcc caa gaa gat gat tgg aca ggg     542
Thr His His Ala Leu Asp Ala Leu Ser Gln Glu Asp Asp Trp Thr Gly
            145                 150                 155 tta tct gag gaa ccg gtg cag caa caa gac cag act gat gcg gcg ggg     590
Leu Ser Glu Glu Pro Val Gln Gln Gln Asp Gln Thr Asp Ala Ala Gly
        160                 165                 170 aat aac ggc gga gga gga agt ggt tac tgg gac gca ggt caa gga aag     638
Asn Asn Gly Gly Gly Gly Ser Gly Tyr Trp Asp Ala Gly Gln Gly Lys
    175                 180                 185 atg aag aag caa cag cag cag aga cgg aga aag aaa cca atg ctg acg     686
Met Lys Lys Gln Gln Gln Gln Arg Arg Arg Lys Lys Pro Met Leu Thr
190                 195                 200                 205 tca gtg gaa acc gac gaa gac gtc aac gaa ggt gag gat gac gac ggg     734
Ser Val Glu Thr Asp Glu Asp Val Asn Glu Gly Glu Asp Asp Asp Gly
                210                 215                 220 atg gat aac ggc aac gga ggt agt ggt ttg ggg aca gag aga cag agg     782
Met Asp Asn Gly Asn Gly Gly Ser Gly Leu Gly Thr Glu Arg Gln Arg
            225                 230                 235 gag cat ccg ttt atc gta acg gag cct ggg gaa gtg gca cgt ggc aaa     830
Glu His Pro Phe Ile Val Thr Glu Pro Gly Glu Val Ala Arg Gly Lys
        240                 245                 250 aag aac ggc tta gat tat ctg ttc cac ttg tac gaa caa tgc cgt gag     878
Lys Asn Gly Leu Asp Tyr Leu Phe His Leu Tyr Glu Gln Cys Arg Glu
    255                 260                 265 ttc ctt ctt cag gtc cag aca att gct aaa gac cgt ggc gaa aaa tgc     926
Phe Leu Leu Gln Val Gln Thr Ile Ala Lys Asp Arg Gly Glu Lys Cys
270                 275                 280                 285
```

```
ccc acc aag gtg acg aac caa gta ttc agg tac gcg aag aaa tca gga      974
Pro Thr Lys Val Thr Asn Gln Val Phe Arg Tyr Ala Lys Lys Ser Gly
            290                 295                 300 gcg agt tac ata aac aag cct aaa atg cga cac tac gtt cac tgt tac     1022
Ala Ser Tyr Ile Asn Lys Pro Lys Met Arg His Tyr Val His Cys Tyr
            305                 310                 315 gct ctc cac tgc cta gac gaa gaa gct tca aat gct ctc aga aga gcg     1070
Ala Leu His Cys Leu Asp Glu Glu Ala Ser Asn Ala Leu Arg Arg Ala
            320                 325                 330 ttt aaa gaa cgc ggt gag aac gtt ggc tca tgg cgt cag gct tgt tac     1118
Phe Lys Glu Arg Gly Glu Asn Val Gly Ser Trp Arg Gln Ala Cys Tyr
    335                 340                 345 aag cca ctt gtg aac atc gct tgt cgt cat ggc tgg gat ata gac gcc     1166
Lys Pro Leu Val Asn Ile Ala Cys Arg His Gly Trp Asp Ile Asp Ala
350                 355                 360                 365 gtc ttt aac gct cat cct cgt ctc tct att tgg tat gtt cca aca aag     1214
Val Phe Asn Ala His Pro Arg Leu Ser Ile Trp Tyr Val Pro Thr Lys
            370                 375                 380 ctg cgt cag ctt tgc cat ttg gag cgg aac aat gcg gtt gct gcg gct     1262
Leu Arg Gln Leu Cys His Leu Glu Arg Asn Asn Ala Val Ala Ala
            385                 390                 395 gcg gct tta gtt ggc ggt att agc tgt acc gga tcg tcg acg tct gga     1310
Ala Ala Leu Val Gly Gly Ile Ser Cys Thr Gly Ser Ser Thr Ser Gly
    400                 405                 410 cgt gga gga tgc ggc ggc gac gac ttg cgt ttc tag tttggtttgg          1356
Arg Gly Gly Cys Gly Gly Asp Asp Leu Arg Phe
    415                 420             425 gtagttgtgg tttgtttagt cgttatccta attaactatt agtctttaat ttagtcttct   1416
tggctaattt attttctttt tttgtcaaa acctttaatt tgttatggct aatttgttat    1476
acacgcagtt ttcttaatgc gtta                                          1500

<210> SEQ ID NO 16
<211> LENGTH: 424
<212> TYPE: PRT
<213> ORGANISM: Arabidopsis thaliana
<220> FEATURE:
<223> OTHER INFORMATION: LEAFY (LFY)

<400> SEQUENCE: 16

Met Asp Pro Glu Gly Phe Thr Ser Gly Leu Phe Arg Trp Asn Pro Thr
1               5                   10                  15

Arg Ala Leu Val Gln Ala Pro Pro Val Pro Pro Pro Leu Gln Gln
            20                  25                  30

Gln Pro Val Thr Pro Gln Thr Ala Ala Phe Gly Met Arg Leu Gly Gly
        35                  40                  45

Leu Glu Gly Leu Phe Gly Pro Tyr Gly Ile Arg Phe Tyr Thr Ala Ala
    50                  55                  60

Lys Ile Ala Glu Leu Gly Phe Thr Ala Ser Thr Leu Val Gly Met Lys
65                  70                  75                  80

Asp Glu Glu Leu Glu Glu Met Met Asn Ser Leu Ser His Ile Phe Arg
                85                  90                  95

Trp Glu Leu Leu Val Gly Glu Arg Tyr Gly Ile Lys Ala Ala Val Arg
            100                 105                 110

Ala Glu Arg Arg Arg Leu Gln Glu Glu Glu Glu Ser Ser Arg
        115                 120                 125

Arg Arg His Leu Leu Leu Ser Ala Ala Gly Asp Ser Gly Thr His His
    130                 135                 140
```

-continued

```
Ala Leu Asp Ala Leu Ser Gln Glu Asp Asp Trp Thr Gly Leu Ser Glu
145                 150                 155                 160

Glu Pro Val Gln Gln Gln Asp Gln Thr Asp Ala Ala Gly Asn Asn Gly
                165                 170                 175

Gly Gly Gly Ser Gly Tyr Trp Asp Ala Gly Gln Gly Lys Met Lys Lys
            180                 185                 190

Gln Gln Gln Gln Arg Arg Arg Lys Lys Pro Met Leu Thr Ser Val Glu
        195                 200                 205

Thr Asp Glu Asp Val Asn Glu Gly Glu Asp Asp Gly Met Asp Asn
210                 215                 220

Gly Asn Gly Gly Ser Gly Leu Gly Thr Glu Arg Gln Arg Glu His Pro
225                 230                 235                 240

Phe Ile Val Thr Glu Pro Gly Glu Val Ala Arg Gly Lys Lys Asn Gly
                245                 250                 255

Leu Asp Tyr Leu Phe His Leu Tyr Glu Gln Cys Arg Glu Phe Leu Leu
            260                 265                 270

Gln Val Gln Thr Ile Ala Lys Asp Arg Gly Glu Lys Cys Pro Thr Lys
        275                 280                 285

Val Thr Asn Gln Val Phe Arg Tyr Ala Lys Lys Ser Gly Ala Ser Tyr
    290                 295                 300

Ile Asn Lys Pro Lys Met Arg His Tyr Val His Cys Tyr Ala Leu His
305                 310                 315                 320

Cys Leu Asp Glu Glu Ala Ser Asn Ala Leu Arg Arg Ala Phe Lys Glu
                325                 330                 335

Arg Gly Glu Asn Val Gly Ser Trp Arg Gln Ala Cys Tyr Lys Pro Leu
            340                 345                 350

Val Asn Ile Ala Cys Arg His Gly Trp Asp Ile Asp Ala Val Phe Asn
        355                 360                 365

Ala His Pro Arg Leu Ser Ile Trp Tyr Val Pro Thr Lys Leu Arg Gln
    370                 375                 380

Leu Cys His Leu Glu Arg Asn Asn Ala Val Ala Ala Ala Ala Leu
385                 390                 395                 400

Val Gly Gly Ile Ser Cys Thr Gly Ser Ser Thr Ser Arg Gly Gly
                405                 410                 415

Cys Gly Gly Asp Asp Leu Arg Phe
            420
```

<210> SEQ ID NO 17
<211> LENGTH: 1656
<212> TYPE: DNA
<213> ORGANISM: Drosophila melanogaster
<220> FEATURE:
<221> NAME/KEY: CDS
<222> LOCATION: (1)..(1653)
<223> OTHER INFORMATION: ecdysone receptor ligand binding domain

<400> SEQUENCE: 17

```
atg cgg ccg gaa tgc gtc gtc ccg gag aac caa tgt gcg atg aag cgg      48
Met Arg Pro Glu Cys Val Val Pro Glu Asn Gln Cys Ala Met Lys Arg
1               5                   10                  15 cgc gaa aag aag gcc cag aag gag aag gac aaa atg acc act tcg ccg      96
Arg Glu Lys Lys Ala Gln Lys Glu Lys Asp Lys Met Thr Thr Ser Pro
                20                  25                  30 agc tct cag cat ggc ggc aat ggc agc ttg gcc tct ggt ggc ggc caa    144
Ser Ser Gln His Gly Gly Asn Gly Ser Leu Ala Ser Gly Gly Gly Gln
            35                  40                  45
```

```
gac ttt gtt aag aag gag att ctt gac ctt atg aca tgc gag ccg ccc      192
Asp Phe Val Lys Lys Glu Ile Leu Asp Leu Met Thr Cys Glu Pro Pro
 50                  55                  60 cag cat gcc act att ccg cta cta cct gat gaa ata ttg gcc aag tgt      240
Gln His Ala Thr Ile Pro Leu Leu Pro Asp Glu Ile Leu Ala Lys Cys
 65                  70                  75                  80 caa gcg cgc aat ata cct tcc tta acg tac aat cag ttg gcc gtt ata      288
Gln Ala Arg Asn Ile Pro Ser Leu Thr Tyr Asn Gln Leu Ala Val Ile
                 85                  90                  95 tac aag tta att tgg tac cag gat ggc tat gag cag cca tct gaa gag      336
Tyr Lys Leu Ile Trp Tyr Gln Asp Gly Tyr Glu Gln Pro Ser Glu Glu
            100                 105                 110 gat ctc agg cgt ata atg agt caa ccc gat gag aac gag agc caa acg      384
Asp Leu Arg Arg Ile Met Ser Gln Pro Asp Glu Asn Glu Ser Gln Thr
        115                 120                 125 gac gtc agc ttt cgg cat ata acc gag ata acc ata ctc acg gtc cag      432
Asp Val Ser Phe Arg His Ile Thr Glu Ile Thr Ile Leu Thr Val Gln
    130                 135                 140 ttg att gtt gag ttt gct aaa ggt cta cca gcg ttt aca aag ata ccc      480
Leu Ile Val Glu Phe Ala Lys Gly Leu Pro Ala Phe Thr Lys Ile Pro
145                 150                 155                 160 cag gag gac cag atc acg tta cta aag gcc tgc tcg tcg gag gtg atg      528
Gln Glu Asp Gln Ile Thr Leu Leu Lys Ala Cys Ser Ser Glu Val Met
                165                 170                 175 atg ctg cgt atg gca cga cgc tat gac cac agc tcg gac tca ata ttc      576
Met Leu Arg Met Ala Arg Arg Tyr Asp His Ser Ser Asp Ser Ile Phe
            180                 185                 190 ttc gcg aat aat aga tca tat acg cgg gat tct tac aaa atg gcc gga      624
Phe Ala Asn Asn Arg Ser Tyr Thr Arg Asp Ser Tyr Lys Met Ala Gly
        195                 200                 205 atg gct gat aac att gaa gac ctg ctg cat ttc tgc cgc caa atg ttc      672
Met Ala Asp Asn Ile Glu Asp Leu Leu His Phe Cys Arg Gln Met Phe
    210                 215                 220 tcg atg aag gtg gac aac gtc gaa tac gcg ctt ctc act gcc att gtg      720
Ser Met Lys Val Asp Asn Val Glu Tyr Ala Leu Leu Thr Ala Ile Val
225                 230                 235                 240 atc ttc tcg gac cgg ccg ggc ctg gag aag gcc caa cta gtc gaa gcg      768
Ile Phe Ser Asp Arg Pro Gly Leu Glu Lys Ala Gln Leu Val Glu Ala
                245                 250                 255 atc cag agc tac tac atc gac acg cta cgc att tat ata ctc aac cgc      816
Ile Gln Ser Tyr Tyr Ile Asp Thr Leu Arg Ile Tyr Ile Leu Asn Arg
            260                 265                 270 cac tgc ggc gac tca atg agc ctc gtc ttc tac gca aag ctg ctc tcg      864
His Cys Gly Asp Ser Met Ser Leu Val Phe Tyr Ala Lys Leu Leu Ser
        275                 280                 285 atc ctc acc gag ctg cgt acg ctg ggc aac cag aac gcc gag atg tgt      912
Ile Leu Thr Glu Leu Arg Thr Leu Gly Asn Gln Asn Ala Glu Met Cys
    290                 295                 300 ttc tca cta aag ctc aaa aac cgc aaa ctg ccc aag ttc ctc gag gag      960
Phe Ser Leu Lys Leu Lys Asn Arg Lys Leu Pro Lys Phe Leu Glu Glu
305                 310                 315                 320 atc tgg gac gtt cat gcc atc ccg cca tcg gtc cag tcg cac ctt cag     1008
Ile Trp Asp Val His Ala Ile Pro Pro Ser Val Gln Ser His Leu Gln
                325                 330                 335 att acc cag gag gag aac gag cgt ctc gag cgg gct gag cgt atg cgg     1056
Ile Thr Gln Glu Glu Asn Glu Arg Leu Glu Arg Ala Glu Arg Met Arg
            340                 345                 350 gca tcg gtt ggg ggc gcc att acc gcc ggc att gat tgc gac tct gcc     1104
Ala Ser Val Gly Gly Ala Ile Thr Ala Gly Ile Asp Cys Asp Ser Ala
        355                 360                 365
```

```
tcc act tcg gcg gcg gca gcc gcg gcc cag cat cag cct cag cct cag    1152
Ser Thr Ser Ala Ala Ala Ala Ala Ala Gln His Gln Pro Gln Pro Gln
    370                 375                 380 ccc cag ccc caa ccc tcc tcc ctg acc cag aac gat tcc cag cac cag    1200
Pro Gln Pro Gln Pro Ser Ser Leu Thr Gln Asn Asp Ser Gln His Gln
385                 390                 395                 400 aca cag ccg cag cta caa cct cag cta cca cct cag ctg caa ggt caa    1248
Thr Gln Pro Gln Leu Gln Pro Gln Leu Pro Pro Gln Leu Gln Gly Gln
                405                 410                 415 ctg caa ccc cag ctc caa cca cag ctt cag acg caa ctc cag cca cag    1296
Leu Gln Pro Gln Leu Gln Pro Gln Leu Gln Thr Gln Leu Gln Pro Gln
            420                 425                 430 att caa cca cag cca cag ctc ctt ccc gtc tcc gct ccc gtg ccc gcc    1344
Ile Gln Pro Gln Pro Gln Leu Leu Pro Val Ser Ala Pro Val Pro Ala
        435                 440                 445 tcc gta acc gca cct ggt tcc ttg tcc gcg gtc agt acg agc agc gaa    1392
Ser Val Thr Ala Pro Gly Ser Leu Ser Ala Val Ser Thr Ser Ser Glu
    450                 455                 460 tac atg ggc gga agt gcg gcc ata gga ccc atc acg ccg gca acc acc    1440
Tyr Met Gly Gly Ser Ala Ala Ile Gly Pro Ile Thr Pro Ala Thr Thr
465                 470                 475                 480 agc agt atc acg gct gcc gtt acc gct agc tcc acc aca tca gcg gta    1488
Ser Ser Ile Thr Ala Ala Val Thr Ala Ser Ser Thr Thr Ser Ala Val
                485                 490                 495 ccg atg ggc aac gga gtt gga gtc ggt gtt ggg gtg ggc ggc aac gtc    1536
Pro Met Gly Asn Gly Val Gly Val Gly Val Gly Val Gly Gly Asn Val
            500                 505                 510 agc atg tat gcg aac gcc cag acg gcg atg gcc ttg atg ggt gta gcc    1584
Ser Met Tyr Ala Asn Ala Gln Thr Ala Met Ala Leu Met Gly Val Ala
        515                 520                 525 ctg cat tcg cac caa gag cag ctt atc ggg gga gtg gcg gtt aag tcg    1632
Leu His Ser His Gln Glu Gln Leu Ile Gly Gly Val Ala Val Lys Ser
    530                 535                 540 gag cac tcg acg act gca tag cag                                    1656
Glu His Ser Thr Thr Ala
545             550

<210> SEQ ID NO 18
<211> LENGTH: 550
<212> TYPE: PRT
<213> ORGANISM: Drosophila melanogaster
<220> FEATURE:
<223> OTHER INFORMATION: ecdysone receptor ligand binding domain

<400> SEQUENCE: 18

Met Arg Pro Glu Cys Val Val Pro Glu Asn Gln Cys Ala Met Lys Arg
1               5                   10                  15

Arg Glu Lys Lys Ala Gln Lys Glu Lys Asp Lys Met Thr Thr Ser Pro
                20                  25                  30

Ser Ser Gln His Gly Gly Asn Gly Ser Leu Ala Ser Gly Gly Gly Gln
            35                  40                  45

Asp Phe Val Lys Lys Glu Ile Leu Asp Leu Met Thr Cys Glu Pro Pro
        50                  55                  60

Gln His Ala Thr Ile Pro Leu Leu Pro Asp Glu Ile Leu Ala Lys Cys
65                  70                  75                  80

Gln Ala Arg Asn Ile Pro Ser Leu Thr Tyr Asn Gln Leu Ala Val Ile
                85                  90                  95

Tyr Lys Leu Ile Trp Tyr Gln Asp Gly Tyr Glu Gln Pro Ser Glu Glu
            100                 105                 110
```

-continued

```
Asp Leu Arg Arg Ile Met Ser Gln Pro Asp Glu Asn Glu Ser Gln Thr
        115                 120                 125

Asp Val Ser Phe Arg His Ile Thr Glu Ile Thr Ile Leu Thr Val Gln
    130                 135                 140

Leu Ile Val Glu Phe Ala Lys Gly Leu Pro Ala Phe Thr Lys Ile Pro
145                 150                 155                 160

Gln Glu Asp Gln Ile Thr Leu Leu Lys Ala Cys Ser Ser Glu Val Met
                165                 170                 175

Met Leu Arg Met Ala Arg Arg Tyr Asp His Ser Ser Asp Ser Ile Phe
            180                 185                 190

Phe Ala Asn Asn Arg Ser Tyr Thr Arg Asp Ser Tyr Lys Met Ala Gly
        195                 200                 205

Met Ala Asp Asn Ile Glu Asp Leu Leu His Phe Cys Arg Gln Met Phe
    210                 215                 220

Ser Met Lys Val Asp Asn Val Glu Tyr Ala Leu Leu Thr Ala Ile Val
225                 230                 235                 240

Ile Phe Ser Asp Arg Pro Gly Leu Glu Lys Ala Gln Leu Val Glu Ala
                245                 250                 255

Ile Gln Ser Tyr Tyr Ile Asp Thr Leu Arg Ile Tyr Ile Leu Asn Arg
            260                 265                 270

His Cys Gly Asp Ser Met Ser Leu Val Phe Tyr Ala Lys Leu Leu Ser
        275                 280                 285

Ile Leu Thr Glu Leu Arg Thr Leu Gly Asn Gln Asn Ala Glu Met Cys
    290                 295                 300

Phe Ser Leu Lys Leu Lys Asn Arg Lys Leu Pro Lys Phe Leu Glu Glu
305                 310                 315                 320

Ile Trp Asp Val His Ala Ile Pro Pro Ser Val Gln Ser His Leu Gln
                325                 330                 335

Ile Thr Gln Glu Glu Asn Glu Arg Leu Glu Arg Ala Glu Arg Met Arg
            340                 345                 350

Ala Ser Val Gly Gly Ala Ile Thr Ala Gly Ile Asp Cys Asp Ser Ala
        355                 360                 365

Ser Thr Ser Ala Ala Ala Ala Ala Gln His Gln Pro Gln Pro Gln
    370                 375                 380

Pro Gln Pro Gln Pro Ser Ser Leu Thr Gln Asn Asp Ser Gln His Gln
385                 390                 395                 400

Thr Gln Pro Gln Leu Gln Pro Gln Leu Pro Pro Gln Leu Gln Gly Gln
                405                 410                 415

Leu Gln Pro Gln Leu Gln Pro Gln Leu Gln Thr Gln Leu Gln Pro Gln
            420                 425                 430

Ile Gln Pro Gln Pro Gln Leu Leu Pro Val Ser Ala Pro Val Pro Ala
        435                 440                 445

Ser Val Thr Ala Pro Gly Ser Leu Ser Ala Val Ser Thr Ser Ser Glu
    450                 455                 460

Tyr Met Gly Gly Ser Ala Ala Ile Gly Pro Ile Thr Pro Ala Thr Thr
465                 470                 475                 480

Ser Ser Ile Thr Ala Ala Val Thr Ala Ser Ser Thr Ser Ala Val
                485                 490                 495

Pro Met Gly Asn Gly Val Gly Val Gly Val Gly Gly Asn Val
            500                 505                 510

Ser Met Tyr Ala Asn Ala Gln Thr Ala Met Ala Leu Met Gly Val Ala
        515                 520                 525
```

```
Leu His Ser His Gln Glu Gln Leu Ile Gly Gly Val Ala Val Lys Ser
    530                 535                 540

Glu His Ser Thr Thr Ala
545                 550

<210> SEQ ID NO 19
<211> LENGTH: 855
<212> TYPE: DNA
<213> ORGANISM: Rattus norvegicus
<220> FEATURE:
<221> NAME/KEY: CDS
<222> LOCATION: (1)..(855)
<223> OTHER INFORMATION: rat glucocorticoid receptor ligand binding
      domain

<400> SEQUENCE: 19 aca aag aaa aaa atc aaa ggg att cag caa gcc act gca gga gtc tca        48
Thr Lys Lys Lys Ile Lys Gly Ile Gln Gln Ala Thr Ala Gly Val Ser
  1               5                  10                  15 caa gac act tcg gaa aat cct aac aaa aca ata gtt cct gca gca tta        96
Gln Asp Thr Ser Glu Asn Pro Asn Lys Thr Ile Val Pro Ala Ala Leu
             20                  25                  30 cca cag ctc acc cct acc ttg gtg tca ctg ctg gag gtg att gaa ccc       144
Pro Gln Leu Thr Pro Thr Leu Val Ser Leu Leu Glu Val Ile Glu Pro
         35                  40                  45 gag gtg ttg tat gca gga tat gat agc tct gtt cca gat tca gca tgg       192
Glu Val Leu Tyr Ala Gly Tyr Asp Ser Ser Val Pro Asp Ser Ala Trp
 50                  55                  60 aga att atg acc aca ctc aac atg tta ggt ggg cgt caa gtg att gca       240
Arg Ile Met Thr Thr Leu Asn Met Leu Gly Gly Arg Gln Val Ile Ala
 65                  70                  75                  80 gca gtg aaa tgg gca aag gcg ata cta ggc ttg aga aac tta cac ctc       288
Ala Val Lys Trp Ala Lys Ala Ile Leu Gly Leu Arg Asn Leu His Leu
                 85                  90                  95 gat gac caa atg acc ctg cta cag tac tca tgg atg ttt ctc atg gca       336
Asp Asp Gln Met Thr Leu Leu Gln Tyr Ser Trp Met Phe Leu Met Ala
            100                 105                 110 ttt gcc ttg ggt tgg aga tca tac aga caa tca agc gga aac ctg ctc       384
Phe Ala Leu Gly Trp Arg Ser Tyr Arg Gln Ser Ser Gly Asn Leu Leu
        115                 120                 125 tgc ttt gct cct gat ctg att att aat gag cag aga atg tct cta ccc       432
Cys Phe Ala Pro Asp Leu Ile Ile Asn Glu Gln Arg Met Ser Leu Pro
    130                 135                 140 tgc atg tat gac caa tgt aaa cac atg ctg ttt gtc tcc tct gaa tta       480
Cys Met Tyr Asp Gln Cys Lys His Met Leu Phe Val Ser Ser Glu Leu
145                 150                 155                 160 caa aga ttg cag gta tcc tat gaa gag tat ctc tgt atg aaa acc tta       528
Gln Arg Leu Gln Val Ser Tyr Glu Glu Tyr Leu Cys Met Lys Thr Leu
                165                 170                 175 ctg ctt ctc tcc tca gtt gct aag gaa ggt ctg aag agc caa gag tta       576
Leu Leu Leu Ser Ser Val Ala Lys Glu Gly Leu Lys Ser Gln Glu Leu
            180                 185                 190 ttt gat gag att cga atg act tat atc aaa gag cta gga aaa gcc atc       624
Phe Asp Glu Ile Arg Met Thr Tyr Ile Lys Glu Leu Gly Lys Ala Ile
        195                 200                 205 gtc aaa agg gaa ggg aac tcc agt cag aac tgg caa cgg ttt tac caa       672
Val Lys Arg Glu Gly Asn Ser Ser Gln Asn Trp Gln Arg Phe Tyr Gln
    210                 215                 220 ctg aca aag ctt ctg gac tcc atg cat gag gtg gtt gag aat ctc ctt       720
Leu Thr Lys Leu Leu Asp Ser Met His Glu Val Val Glu Asn Leu Leu
225                 230                 235                 240
```

```
acc tac tgc ttc cag aca ttt ttg gat aag acc atg agt att gaa ttc      768
Thr Tyr Cys Phe Gln Thr Phe Leu Asp Lys Thr Met Ser Ile Glu Phe
            245                 250                 255 cca gag atg tta gct gaa atc atc act aat cag ata cca aaa tat tca      816
Pro Glu Met Leu Ala Glu Ile Ile Thr Asn Gln Ile Pro Lys Tyr Ser
        260                 265                 270 aat gga aat atc aaa aag ctt ctg ttt cat caa aaa tga                  855
Asn Gly Asn Ile Lys Lys Leu Leu Phe His Gln Lys
            275                 280                 285
```

<210> SEQ ID NO 20
<211> LENGTH: 284
<212> TYPE: PRT
<213> ORGANISM: Rattus norvegicus
<220> FEATURE:
<223> OTHER INFORMATION: rat glucocorticoid receptor ligand binding domain

<400> SEQUENCE: 20

```
Thr Lys Lys Ile Lys Gly Ile Gln Gln Ala Thr Ala Gly Val Ser
 1               5                  10                  15

Gln Asp Thr Ser Glu Asn Pro Asn Lys Thr Ile Val Pro Ala Ala Leu
                20                  25                  30

Pro Gln Leu Thr Pro Thr Leu Val Ser Leu Leu Glu Val Ile Glu Pro
            35                  40                  45

Glu Val Leu Tyr Ala Gly Tyr Asp Ser Ser Val Pro Asp Ser Ala Trp
 50                  55                  60

Arg Ile Met Thr Thr Leu Asn Met Leu Gly Gly Arg Gln Val Ile Ala
 65                  70                  75                  80

Ala Val Lys Trp Ala Lys Ala Ile Leu Gly Leu Arg Asn Leu His Leu
                 85                  90                  95

Asp Asp Gln Met Thr Leu Leu Gln Tyr Ser Trp Met Phe Leu Met Ala
            100                 105                 110

Phe Ala Leu Gly Trp Arg Ser Tyr Arg Gln Ser Ser Gly Asn Leu Leu
        115                 120                 125

Cys Phe Ala Pro Asp Leu Ile Ile Asn Glu Gln Arg Met Ser Leu Pro
130                 135                 140

Cys Met Tyr Asp Gln Cys Lys His Met Leu Phe Val Ser Ser Glu Leu
145                 150                 155                 160

Gln Arg Leu Gln Val Ser Tyr Glu Glu Tyr Leu Cys Met Lys Thr Leu
                165                 170                 175

Leu Leu Leu Ser Ser Val Ala Lys Glu Gly Leu Lys Ser Gln Glu Leu
            180                 185                 190

Phe Asp Glu Ile Arg Met Thr Tyr Ile Lys Glu Leu Gly Lys Ala Ile
        195                 200                 205

Val Lys Arg Glu Gly Asn Ser Ser Gln Asn Trp Gln Arg Phe Tyr Gln
210                 215                 220

Leu Thr Lys Leu Leu Asp Ser Met His Glu Val Val Glu Asn Leu Leu
225                 230                 235                 240

Thr Tyr Cys Phe Gln Thr Phe Leu Asp Lys Thr Met Ser Ile Glu Phe
                245                 250                 255

Pro Glu Met Leu Ala Glu Ile Ile Thr Asn Gln Ile Pro Lys Tyr Ser
            260                 265                 270

Asn Gly Asn Ile Lys Lys Leu Leu Phe His Gln Lys
        275                 280
```

<210> SEQ ID NO 21

```
<211> LENGTH: 50
<212> TYPE: DNA
<213> ORGANISM: Artificial Sequence
<220> FEATURE:
<223> OTHER INFORMATION: Description of Artificial Sequence:copper
      inducible regulatory element, ACE1 binding site
      from metallothionein gene promoter

<400> SEQUENCE: 21
agcttagcga tgcgtctttt ccgctgaacc gttccagcaa aaaagactag              50

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:tet operator
      sequence

<400> SEQUENCE: 22
actctatcag tgatagagt                                               19

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:ecdysone
      response element (EcRE)

<400> SEQUENCE: 23
gatccgacaa gggttcaatg cacttgtca                                    29

<210> SEQ ID NO 24
<211> LENGTH: 371
<212> TYPE: DNA
<213> ORGANISM: Arabidopsis thaliana
<220> FEATURE:
<223> OTHER INFORMATION: inducible regulatory element from HSP81-1 heat
      shock gene promoter

<400> SEQUENCE: 24
gtggagtctc gaaacgaaaa gaactttctg gaattcgttt gctcacaaag ctaaaaacgg   60
ttgatttcat cgaaatacgg cgtcgttttc aaagaacaat ccagaaatca ctggtttttcc  120 tttatttcaa aagaagagac tagaacttta tttctcctct ataaaatcac tttgttttc    180 cctctcttct tcataaatca acaaaacaat cacaaatctc tcgaaacgct tcgaagttc    240 caaatttct cttagcattc tctttcgttt ctcgtttgcg ttgaatcaaa gttcgttgcg    300
atggcggatg ttcagatggc tgatgcagag acttttgctt tccaagctga gattaaccag   360
cttcttagct t                                                      371

<210> SEQ ID NO 25
<211> LENGTH:
<212> TYPE:
<213> ORGANISM:

<400> SEQUENCE: 25

000

<210> SEQ ID NO 26
<211> LENGTH:
<212> TYPE:
<213> ORGANISM:
```

<400> SEQUENCE: 26

000

<210> SEQ ID NO 27
<211> LENGTH: 747
<212> TYPE: DNA
<213> ORGANISM: Arabidopsis thaliana
<220> FEATURE:
<221> NAME/KEY: CDS
<222> LOCATION: (1)..(747)
<223> OTHER INFORMATION: SEPALLATA1 (SEP1)

<400> SEQUENCE: 27

| | | | | | | | | | | | | | | | | |
|---|---|---|---|---|---|---|---|---|---|---|---|---|---|---|---|---|
| atg | gga | aga | gga | aga | gta | gag | ctg | aag | agg | ata | gag | aac | aaa | atc | aac | 48 |
| Met | Gly | Arg | Gly | Arg | Val | Glu | Leu | Lys | Arg | Ile | Glu | Asn | Lys | Ile | Asn | |
| 1 | | | | 5 | | | | | 10 | | | | | 15 | | |
| aga | caa | gta | acg | ttt | gca | aag | cgt | agg | aac | ggt | ttg | ttg | aag | aaa | gct | 96 |
| Arg | Gln | Val | Thr | Phe | Ala | Lys | Arg | Arg | Asn | Gly | Leu | Leu | Lys | Lys | Ala | |
| | | | 20 | | | | | 25 | | | | | 30 | | | |
| tat | gaa | ttg | tct | gtt | ctc | tgt | gat | gct | gaa | gtt | gct | ctc | atc | atc | ttc | 144 |
| Tyr | Glu | Leu | Ser | Val | Leu | Cys | Asp | Ala | Glu | Val | Ala | Leu | Ile | Ile | Phe | |
| | | 35 | | | | | 40 | | | | | 45 | | | | |
| tcc | aac | cgt | gga | aag | ctc | tat | gag | ttt | tgc | agc | tcc | tca | aac | atg | ctc | 192 |
| Ser | Asn | Arg | Gly | Lys | Leu | Tyr | Glu | Phe | Cys | Ser | Ser | Ser | Asn | Met | Leu | |
| 50 | | | | | 55 | | | | | 60 | | | | | | |
| aag | aca | ctt | gat | cgg | tac | cag | aaa | tgc | agc | tat | gga | tcc | att | gaa | gtc | 240 |
| Lys | Thr | Leu | Asp | Arg | Tyr | Gln | Lys | Cys | Ser | Tyr | Gly | Ser | Ile | Glu | Val | |
| 65 | | | | | 70 | | | | | 75 | | | | | 80 | |
| aac | aac | aaa | cct | gcc | aaa | gaa | ctt | gag | aac | agc | tac | aga | gaa | tat | ctg | 288 |
| Asn | Asn | Lys | Pro | Ala | Lys | Glu | Leu | Glu | Asn | Ser | Tyr | Arg | Glu | Tyr | Leu | |
| | | | | 85 | | | | | 90 | | | | | 95 | | |
| aag | ctt | aag | ggt | aga | tat | gag | aac | ctt | caa | cgt | caa | cag | aga | aat | ctt | 336 |
| Lys | Leu | Lys | Gly | Arg | Tyr | Glu | Asn | Leu | Gln | Arg | Gln | Gln | Arg | Asn | Leu | |
| | | | 100 | | | | | 105 | | | | | 110 | | | |
| ctt | ggg | gag | gat | tta | gga | cct | ttg | aat | tca | aag | gag | tta | gag | cag | ctt | 384 |
| Leu | Gly | Glu | Asp | Leu | Gly | Pro | Leu | Asn | Ser | Lys | Glu | Leu | Glu | Gln | Leu | |
| | | 115 | | | | | 120 | | | | | 125 | | | | |
| gag | cgt | caa | ctg | gac | ggc | tct | ctc | aag | caa | gtt | cgg | tcc | atc | aag | aca | 432 |
| Glu | Arg | Gln | Leu | Asp | Gly | Ser | Leu | Lys | Gln | Val | Arg | Ser | Ile | Lys | Thr | |
| | 130 | | | | | 135 | | | | | 140 | | | | | |
| cag | tac | atg | ctt | gac | cag | ctc | tcg | gat | ctt | caa | aat | aaa | gag | caa | atg | 480 |
| Gln | Tyr | Met | Leu | Asp | Gln | Leu | Ser | Asp | Leu | Gln | Asn | Lys | Glu | Gln | Met | |
| 145 | | | | | 150 | | | | | 155 | | | | | 160 | |
| ttg | ctt | gaa | acc | aat | aga | gct | ttg | gca | atg | aag | ctg | gat | gat | atg | att | 528 |
| Leu | Leu | Glu | Thr | Asn | Arg | Ala | Leu | Ala | Met | Lys | Leu | Asp | Asp | Met | Ile | |
| | | | | 165 | | | | | 170 | | | | | 175 | | |
| ggt | gtg | aga | agt | cat | cat | atg | gga | gga | tgg | gaa | ggc | ggt | gaa | cag | aat | 576 |
| Gly | Val | Arg | Ser | His | His | Met | Gly | Gly | Trp | Glu | Gly | Gly | Glu | Gln | Asn | |
| | | | 180 | | | | | 185 | | | | | 190 | | | |
| gtt | acc | tac | gcg | cat | cat | caa | gct | cag | tct | cag | gga | cta | tac | cag | cct | 624 |
| Val | Thr | Tyr | Ala | His | His | Gln | Ala | Gln | Ser | Gln | Gly | Leu | Tyr | Gln | Pro | |
| | | 195 | | | | | 200 | | | | | 205 | | | | |
| ctt | gaa | tgc | aat | cca | act | ctg | caa | atg | ggg | tat | gat | aat | cca | gta | tgc | 672 |
| Leu | Glu | Cys | Asn | Pro | Thr | Leu | Gln | Met | Gly | Tyr | Asp | Asn | Pro | Val | Cys | |
| | 210 | | | | | 215 | | | | | 220 | | | | | |
| tct | gag | caa | atc | act | gcg | aca | aca | caa | gct | cag | gcg | cag | ccg | gga | aac | 720 |
| Ser | Glu | Gln | Ile | Thr | Ala | Thr | Thr | Gln | Ala | Gln | Ala | Gln | Pro | Gly | Asn | |
| 225 | | | | | 230 | | | | | 235 | | | | | 240 | |
| ggt | tac | att | cca | gga | tgg | atg | ctc | tga | | | | | | | | 747 |
| Gly | Tyr | Ile | Pro | Gly | Trp | Met | Leu | | | | | | | | | |
| | | | | 245 | | | | | | | | | | | | |

```
<210> SEQ ID NO 28
<211> LENGTH: 248
<212> TYPE: PRT
<213> ORGANISM: Arabidopsis thaliana
<220> FEATURE:
<223> OTHER INFORMATION: SEPALLATA1 (SEP1)

<400> SEQUENCE: 28

Met Gly Arg Gly Arg Val Glu Leu Lys Arg Ile Glu Asn Lys Ile Asn
 1               5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
         35                  40                  45

Ser Asn Arg Gly Lys Leu Tyr Glu Phe Cys Ser Ser Ser Asn Met Leu
     50                  55                  60

Lys Thr Leu Asp Arg Tyr Gln Lys Cys Ser Tyr Gly Ser Ile Glu Val
 65                  70                  75                  80

Asn Asn Lys Pro Ala Lys Glu Leu Glu Asn Ser Tyr Arg Glu Tyr Leu
                 85                  90                  95

Lys Leu Lys Gly Arg Tyr Glu Asn Leu Gln Arg Gln Arg Asn Leu
            100                 105                 110

Leu Gly Glu Asp Leu Gly Pro Leu Asn Ser Lys Glu Leu Glu Gln Leu
        115                 120                 125

Glu Arg Gln Leu Asp Gly Ser Leu Lys Gln Val Arg Ser Ile Lys Thr
    130                 135                 140

Gln Tyr Met Leu Asp Gln Leu Ser Asp Leu Gln Asn Lys Glu Gln Met
145                 150                 155                 160

Leu Leu Glu Thr Asn Arg Ala Leu Ala Met Lys Leu Asp Asp Met Ile
                165                 170                 175

Gly Val Arg Ser His His Met Gly Gly Trp Glu Gly Gly Glu Gln Asn
            180                 185                 190

Val Thr Tyr Ala His His Gln Ala Gln Ser Gln Gly Leu Tyr Gln Pro
        195                 200                 205

Leu Glu Cys Asn Pro Thr Leu Gln Met Gly Tyr Asp Asn Pro Val Cys
    210                 215                 220

Ser Glu Gln Ile Thr Ala Thr Thr Gln Ala Gln Ala Gln Pro Gly Asn
225                 230                 235                 240

Gly Tyr Ile Pro Gly Trp Met Leu
                245

<210> SEQ ID NO 29
<211> LENGTH: 753
<212> TYPE: DNA
<213> ORGANISM: Arabidopsis thaliana
<220> FEATURE:
<221> NAME/KEY: CDS
<222> LOCATION: (1)..(753)
<223> OTHER INFORMATION: SEPALLATA2 (SEP2)

<400> SEQUENCE: 29 atg gga aga gga aga gta gag ctc aag agg ata gag aac aaa atc aac      48
Met Gly Arg Gly Arg Val Glu Leu Lys Arg Ile Glu Asn Lys Ile Asn
 1               5                  10                  15 aga caa gtg acg ttt gct aaa cgt aga aat ggt ttg ctg aaa aaa gct      96
Arg Gln Val Thr Phe Ala Lys Arg Arg Asn Gly Leu Leu Lys Lys Ala
             20                  25                  30
```

| | | |
|---|---|---|
| tat gag ctt tct gtt ctc tgc gat gct gaa gtc tct ctc atc gtc ttc | | 144 |
| Tyr Glu Leu Ser Val Leu Cys Asp Ala Glu Val Ser Leu Ile Val Phe | | |
| 35 40 45 | | |
| tcc aac cgt ggc aag ctc tac gag ttc tgc agc acc tcc aac atg ctc | | 192 |
| Ser Asn Arg Gly Lys Leu Tyr Glu Phe Cys Ser Thr Ser Asn Met Leu | | |
| 50 55 60 | | |
| aag aca ctg gaa agg tat cag aag tgt agc tat ggc tcc att gaa gtc | | 240 |
| Lys Thr Leu Glu Arg Tyr Gln Lys Cys Ser Tyr Gly Ser Ile Glu Val | | |
| 65 70 75 80 | | |
| aac aac aaa cct gct aaa gag ctt gag aac agc tac aga gag tac ttg | | 288 |
| Asn Asn Lys Pro Ala Lys Glu Leu Glu Asn Ser Tyr Arg Glu Tyr Leu | | |
| 85 90 95 | | |
| aag ctg aaa ggt aga tat gaa aat ctg caa cgt cag cag aga aat ctt | | 336 |
| Lys Leu Lys Gly Arg Tyr Glu Asn Leu Gln Arg Gln Gln Arg Asn Leu | | |
| 100 105 110 | | |
| ctt gga gag gat ctt gga cct ctg aat tca aag gag cta gag cag ctt | | 384 |
| Leu Gly Glu Asp Leu Gly Pro Leu Asn Ser Lys Glu Leu Glu Gln Leu | | |
| 115 120 125 | | |
| gag cgt caa cta gac ggc tct ctg aag caa gtt cgc tgc atc aag aca | | 432 |
| Glu Arg Gln Leu Asp Gly Ser Leu Lys Gln Val Arg Cys Ile Lys Thr | | |
| 130 135 140 | | |
| cag tat atg ctt gac cag ctc tct gat ctt caa ggt aag gag cat atc | | 480 |
| Gln Tyr Met Leu Asp Gln Leu Ser Asp Leu Gln Gly Lys Glu His Ile | | |
| 145 150 155 160 | | |
| ttg ctt gat gcc aac aga gct ttg tca atg aag ctg gaa gat atg atc | | 528 |
| Leu Leu Asp Ala Asn Arg Ala Leu Ser Met Lys Leu Glu Asp Met Ile | | |
| 165 170 175 | | |
| ggc gtg aga cat cac cat ata gga gga gga tgg gaa ggt ggt gat caa | | 576 |
| Gly Val Arg His His His Ile Gly Gly Gly Trp Glu Gly Gly Asp Gln | | |
| 180 185 190 | | |
| cag aat att gcc tat gga cat cct cag gct cat tct cag gga cta tac | | 624 |
| Gln Asn Ile Ala Tyr Gly His Pro Gln Ala His Ser Gln Gly Leu Tyr | | |
| 195 200 205 | | |
| caa tct ctt gaa tgt gat ccc act ttg caa att gga tat agc cat cca | | 672 |
| Gln Ser Leu Glu Cys Asp Pro Thr Leu Gln Ile Gly Tyr Ser His Pro | | |
| 210 215 220 | | |
| gtg tgc tca gag caa atg gct gtg acg gtg caa ggt cag tcc caa caa | | 720 |
| Val Cys Ser Glu Gln Met Ala Val Thr Val Gln Gly Gln Ser Gln Gln | | |
| 225 230 235 240 | | |
| gga aac ggc tac atc cct ggc tgg atg ctg tga | | 753 |
| Gly Asn Gly Tyr Ile Pro Gly Trp Met Leu | | |
| 245 250 | | |

<210> SEQ ID NO 30
<211> LENGTH: 250
<212> TYPE: PRT
<213> ORGANISM: Arabidopsis thaliana
<220> FEATURE:
<223> OTHER INFORMATION: SEPALLATA2 (SEP2)

<400> SEQUENCE: 30

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ser Leu Ile Val Phe
            35                  40                  45

Ser Asn Arg Gly Lys Leu Tyr Glu Phe Cys Ser Thr Ser Asn Met Leu
        50                  55                  60

Lys Thr Leu Glu Arg Tyr Gln Lys Cys Ser Tyr Gly Ser Ile Glu Val

```
                65                  70                  75                  80
Asn Asn Lys Pro Ala Lys Glu Leu Glu Asn Ser Tyr Arg Glu Tyr Leu
                        85                  90                  95

Lys Leu Lys Gly Arg Tyr Glu Asn Leu Gln Arg Gln Gln Arg Asn Leu
                100                 105                 110

Leu Gly Glu Asp Leu Gly Pro Leu Asn Ser Lys Glu Leu Glu Gln Leu
                115                 120                 125

Glu Arg Gln Leu Asp Gly Ser Leu Lys Gln Val Arg Cys Ile Lys Thr
            130                 135                 140

Gln Tyr Met Leu Asp Gln Leu Ser Asp Leu Gln Gly Lys Glu His Ile
145                 150                 155                 160

Leu Leu Asp Ala Asn Arg Ala Leu Ser Met Lys Leu Glu Asp Met Ile
                165                 170                 175

Gly Val Arg His His His Ile Gly Gly Trp Glu Gly Gly Asp Gln
                180                 185                 190

Gln Asn Ile Ala Tyr Gly His Pro Gln Ala His Ser Gln Gly Leu Tyr
                195                 200                 205

Gln Ser Leu Glu Cys Asp Pro Thr Leu Gln Ile Gly Tyr Ser His Pro
    210                 215                 220

Val Cys Ser Glu Gln Met Ala Val Thr Val Gln Gly Gln Ser Gln Gln
225                 230                 235                 240

Gly Asn Gly Tyr Ile Pro Gly Trp Met Leu
                245                 250

<210> SEQ ID NO 31
<211> LENGTH: 714
<212> TYPE: DNA
<213> ORGANISM: Arabidopsis thaliana
<220> FEATURE:
<221> NAME/KEY: CDS
<222> LOCATION: (1)..(714)
<223> OTHER INFORMATION: SEPALLATA3 (SEP3)

<400> SEQUENCE: 31 atg gga aga ggg aga gta gaa ttg aag agg ata gag aac aag atc aat      48
Met Gly Arg Gly Arg Val Glu Leu Lys Arg Ile Glu Asn Lys Ile Asn
  1               5                  10                  15 agg caa gtg acg ttt gca aag aga agg aat ggt ctt ttg aag aaa gca      96
Arg Gln Val Thr Phe Ala Lys Arg Arg Asn Gly Leu Leu Lys Lys Ala
                20                  25                  30 tac gag ctt tca gtt cta tgt gat gca gaa gtt gct ctc atc atc ttc     144
Tyr Glu Leu Ser Val Leu Cys Asp Ala Glu Val Ala Leu Ile Ile Phe
            35                  40                  45 tca aat aga gga aag ctg tac gag ttt tgc agt agt tcg agc atg ctt     192
Ser Asn Arg Gly Lys Leu Tyr Glu Phe Cys Ser Ser Ser Ser Met Leu
        50                  55                  60 cgg aca ctg gag agg tac caa aag tgt aac tat gga gca cca gaa ccc     240
Arg Thr Leu Glu Arg Tyr Gln Lys Cys Asn Tyr Gly Ala Pro Glu Pro
 65                  70                  75                  80 aat gtg cct tca aga gag gcc tta gca gtt gaa ctt agt agc cag cag     288
Asn Val Pro Ser Arg Glu Ala Leu Ala Val Glu Leu Ser Ser Gln Gln
                85                  90                  95 gag tat ctc aag ctt aag gag cgt tat gac gcc tta caa aga acc caa     336
Glu Tyr Leu Lys Leu Lys Glu Arg Tyr Asp Ala Leu Gln Arg Thr Gln
                100                 105                 110 agg aat ctg ttg gga gaa gat ctt gga cct cta agt aca aag gag ctt     384
Arg Asn Leu Leu Gly Glu Asp Leu Gly Pro Leu Ser Thr Lys Glu Leu
            115                 120                 125
```

```
gag tca ctt gag aga cag ctt gat tct tcc ttg aag cag atc aga gct    432
Glu Ser Leu Glu Arg Gln Leu Asp Ser Ser Leu Lys Gln Ile Arg Ala
130                 135                 140 ctc agg aca cag ttt atg ctt gac cag ctc aac gat ctt cag agt aag    480
Leu Arg Thr Gln Phe Met Leu Asp Gln Leu Asn Asp Leu Gln Ser Lys
145                 150                 155                 160 tta gct gat ggg tat cag atg cca ctc cag ctg aac cct aac caa gaa    528
Leu Ala Asp Gly Tyr Gln Met Pro Leu Gln Leu Asn Pro Asn Gln Glu
                165                 170                 175 gag gtt gat cac tac ggt cgt cat cat cat caa caa caa caa cac tcc    576
Glu Val Asp His Tyr Gly Arg His His His Gln Gln Gln Gln His Ser
            180                 185                 190 caa gct ttc ttc cag cct ttg gaa tgt gaa ccc att ctt cag atc ggg    624
Gln Ala Phe Phe Gln Pro Leu Glu Cys Glu Pro Ile Leu Gln Ile Gly
        195                 200                 205 tat cag ggg cag caa gat gga atg gga gca gga cca agt gtg aat aat    672
Tyr Gln Gly Gln Gln Asp Gly Met Gly Ala Gly Pro Ser Val Asn Asn
    210                 215                 220 tac atg ttg ggt tgg tta cct tat gac acc aac tct att tga            714
Tyr Met Leu Gly Trp Leu Pro Tyr Asp Thr Asn Ser Ile
225                 230                 235

<210> SEQ ID NO 32
<211> LENGTH: 237
<212> TYPE: PRT
<213> ORGANISM: Arabidopsis thaliana
<220> FEATURE:
<223> OTHER INFORMATION: SEPALLATA3 (SEP3)

<400> SEQUENCE: 32

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Ser Ser Ser Met Leu
        50                  55                  60

Arg Thr Leu Glu Arg Tyr Gln Lys Cys Asn Tyr Gly Ala Pro Glu Pro
65                  70                  75                  80

Asn Val Pro Ser Arg Glu Ala Leu Ala Val Glu Leu Ser Ser Gln Gln
                85                  90                  95

Glu Tyr Leu Lys Leu Lys Glu Arg Tyr Asp Ala Leu Gln Arg Thr Gln
            100                 105                 110

Arg Asn Leu Leu Gly Glu Asp Leu Gly Pro Leu Ser Thr Lys Glu Leu
        115                 120                 125

Glu Ser Leu Glu Arg Gln Leu Asp Ser Ser Leu Lys Gln Ile Arg Ala
130                 135                 140

Leu Arg Thr Gln Phe Met Leu Asp Gln Leu Asn Asp Leu Gln Ser Lys
145                 150                 155                 160

Leu Ala Asp Gly Tyr Gln Met Pro Leu Gln Leu Asn Pro Asn Gln Glu
                165                 170                 175

Glu Val Asp His Tyr Gly Arg His His His Gln Gln Gln Gln His Ser
            180                 185                 190

Gln Ala Phe Phe Gln Pro Leu Glu Cys Glu Pro Ile Leu Gln Ile Gly
        195                 200                 205

Tyr Gln Gly Gln Gln Asp Gly Met Gly Ala Gly Pro Ser Val Asn Asn
    210                 215                 220
```

```
Tyr Met Leu Gly Trp Leu Pro Tyr Asp Thr Asn Ser Ile
225                 230                 235

<210> SEQ ID NO 33
<211> LENGTH: 645
<212> TYPE: DNA
<213> ORGANISM: Arabidopsis thaliana
<220> FEATURE:
<221> NAME/KEY: CDS
<222> LOCATION: (1)..(645)
<223> OTHER INFORMATION: AGL20 (SUPPRESSOR OF CONSTANS (CO)
      OVEREXPRESSION
      1 (SOC1))

<400> SEQUENCE: 33 atg gtg agg ggc aaa act cag atg aag aga ata gag aat gca aca agc         48
Met Val Arg Gly Lys Thr Gln Met Lys Arg Ile Glu Asn Ala Thr Ser
 1               5                  10                  15 aga caa gtg act ttc tcc aaa aga agg aat ggt ttg ttg aag aaa gcc         96
Arg Gln Val Thr Phe Ser Lys Arg Arg Asn Gly Leu Leu Lys Lys Ala
            20                  25                  30 ttt gag ctc tca gtg ctt tgt gat gct gaa gtt tct ctt atc atc ttc        144
Phe Glu Leu Ser Val Leu Cys Asp Ala Glu Val Ser Leu Ile Ile Phe
        35                  40                  45 tct cct aaa ggc aaa ctt tat gaa ttc gcc agc tcc aat atg caa gat        192
Ser Pro Lys Gly Lys Leu Tyr Glu Phe Ala Ser Ser Asn Met Gln Asp
    50                  55                  60 acc ata gat cgt tat ctg agg cat act aag gat cga gtc agc acc aaa        240
Thr Ile Asp Arg Tyr Leu Arg His Thr Lys Asp Arg Val Ser Thr Lys
 65                  70                  75                  80 ccg gtt tct gaa gaa aat atg cag cat ttg aaa tat gaa gca gca aac        288
Pro Val Ser Glu Glu Asn Met Gln His Leu Lys Tyr Glu Ala Ala Asn
                 85                  90                  95 atg atg aag aaa att gaa caa ctc gaa gct tct aaa cgt aaa ctc ttg        336
Met Met Lys Lys Ile Glu Gln Leu Glu Ala Ser Lys Arg Lys Leu Leu
            100                 105                 110 gga gaa ggc ata gga aca tgc tca atc gag gag ctg caa cag att gag        384
Gly Glu Gly Ile Gly Thr Cys Ser Ile Glu Glu Leu Gln Gln Ile Glu
        115                 120                 125 caa cag ctt gag aaa agt gtc aaa tgt att cga gca aga aag act caa        432
Gln Gln Leu Glu Lys Ser Val Lys Cys Ile Arg Ala Arg Lys Thr Gln
    130                 135                 140 gtg ttt aag gaa caa att gag cag ctc aag caa aag gag aaa gct cta        480
Val Phe Lys Glu Gln Ile Glu Gln Leu Lys Gln Lys Glu Lys Ala Leu
145                 150                 155                 160 gct gca gaa aac gag aag ctc tct gaa aag tgg gga tct cat gaa agc        528
Ala Ala Glu Asn Glu Lys Leu Ser Glu Lys Trp Gly Ser His Glu Ser
                165                 170                 175 gaa gtt tgg tca aat aag aat caa gaa agt act gga aga ggt gat gaa        576
Glu Val Trp Ser Asn Lys Asn Gln Glu Ser Thr Gly Arg Gly Asp Glu
            180                 185                 190 gag agt agc cca agt tct gaa gta gag acg caa ttg ttc att ggg tta        624
Glu Ser Ser Pro Ser Ser Glu Val Glu Thr Gln Leu Phe Ile Gly Leu
        195                 200                 205 cct tgt tct tca aga aag tga                                            645
Pro Cys Ser Ser Arg Lys
    210                 215

<210> SEQ ID NO 34
<211> LENGTH: 214
<212> TYPE: PRT
<213> ORGANISM: Arabidopsis thaliana
```

```
<220> FEATURE:
<223> OTHER INFORMATION: AGL20 (SUPPRESSOR OF CONSTANS (CO)
      OVEREXPRESSION
      1 (SOC1))

<400> SEQUENCE: 34

Met Val Arg Gly Lys Thr Gln Met Lys Arg Ile Glu Asn Ala Thr Ser
 1               5                  10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ser Leu Ile Ile Phe
        35                  40                  45

Ser Pro Lys Gly Lys Leu Tyr Glu Phe Ala Ser Ser Asn Met Gln Asp
 50                  55                  60

Thr Ile Asp Arg Tyr Leu Arg His Thr Lys Asp Arg Val Ser Thr Lys
 65                  70                  75                  80

Pro Val Ser Glu Glu Asn Met Gln His Leu Lys Tyr Glu Ala Ala Asn
                85                  90                  95

Met Met Lys Lys Ile Glu Gln Leu Glu Ala Ser Lys Arg Lys Leu Leu
            100                 105                 110

Gly Glu Gly Ile Gly Thr Cys Ser Ile Glu Glu Leu Gln Gln Ile Glu
        115                 120                 125

Gln Gln Leu Glu Lys Ser Val Lys Cys Ile Arg Ala Arg Lys Thr Gln
130                 135                 140

Val Phe Lys Glu Gln Ile Glu Gln Leu Lys Gln Lys Glu Lys Ala Leu
145                 150                 155                 160

Ala Ala Glu Asn Glu Lys Leu Ser Glu Lys Trp Gly Ser His Glu Ser
                165                 170                 175

Glu Val Trp Ser Asn Lys Asn Gln Glu Ser Thr Gly Arg Gly Asp Glu
            180                 185                 190

Glu Ser Ser Pro Ser Ser Glu Val Glu Thr Gln Leu Phe Ile Gly Leu
        195                 200                 205

Pro Cys Ser Ser Arg Lys
    210

<210> SEQ ID NO 35
<211> LENGTH: 633
<212> TYPE: DNA
<213> ORGANISM: Arabidopsis thaliana
<220> FEATURE:
<221> NAME/KEY: CDS
<222> LOCATION: (1)..(633)
<223> OTHER INFORMATION: AGL22 (SHORT VEGETATIVE PHASE (SVP))
<220> FEATURE:
<221> NAME/KEY: modified_base
<222> LOCATION: (213)
<223> OTHER INFORMATION: n = g, a, c or t

<400> SEQUENCE: 35 atg gcg aga gaa aag att cag atc agg aag atc gac aac gca acg gcg      48
Met Ala Arg Glu Lys Ile Gln Ile Arg Lys Ile Asp Asn Ala Thr Ala
 1               5                  10                  15 aga caa gtg acg ttt tcg aaa cga aga aga ggg ctt ttc aag aaa gct      96
Arg Gln Val Thr Phe Ser Lys Arg Arg Arg Gly Leu Phe Lys Lys Ala
            20                  25                  30 gaa gaa ctc tcc gtt ctc tgc gac gcc gat gtc gct ctc atc atc ttc     144
Glu Glu Leu Ser Val Leu Cys Asp Ala Asp Val Ala Leu Ile Ile Phe
        35                  40                  45 tct tcc acc gga aaa ctg ttc gag ttc tgt agc tcc agc atg aag gaa     192
Ser Ser Thr Gly Lys Leu Phe Glu Phe Cys Ser Ser Ser Met Lys Glu
```

```
                50                  55                  60
gtc cta gag agg cat aac ttn cag tca aag aac ttg gag aag ctt cat    240
Val Leu Glu Arg His Asn Xaa Gln Ser Lys Asn Leu Glu Lys Leu His
 65                  70                  75                  80 cag cca tct ctt gag tta cag ctg gtt gag aac agt gat cac gcc cga    288
Gln Pro Ser Leu Glu Leu Gln Leu Val Glu Asn Ser Asp His Ala Arg
                 85                  90                  95 atg agt aaa gaa att gcg gac aag agc cac cga cta agg caa atg aga    336
Met Ser Lys Glu Ile Ala Asp Lys Ser His Arg Leu Arg Gln Met Arg
            100                 105                 110 gga gag gaa ctt caa gga ctt gac att gaa gag ctt cag cag cta gag    384
Gly Glu Glu Leu Gln Gly Leu Asp Ile Glu Glu Leu Gln Gln Leu Glu
        115                 120                 125 aag gcc ctt gaa act ggt ttg acg cgt gtg att gaa aca aag agt gac    432
Lys Ala Leu Glu Thr Gly Leu Thr Arg Val Ile Glu Thr Lys Ser Asp
    130                 135                 140 aag att atg agt gag atc agc gaa ctt cag aaa aag gga atg caa ttg    480
Lys Ile Met Ser Glu Ile Ser Glu Leu Gln Lys Lys Gly Met Gln Leu
145                 150                 155                 160 atg gat gag aac aag cgg ttg agg cag caa gta tgt gtc tta ccc tct    528
Met Asp Glu Asn Lys Arg Leu Arg Gln Gln Val Cys Val Leu Pro Ser
                165                 170                 175 ctg ttg ata aca aat ccc ttt ctt ttg tct acc att aac gta cac act    576
Leu Leu Ile Thr Asn Pro Phe Leu Leu Ser Thr Ile Asn Val His Thr
            180                 185                 190 cct aaa ttt aat ccc cag ttg tct aca aca cat atg ttt gat cat act    624
Pro Lys Phe Asn Pro Gln Leu Ser Thr Thr His Met Phe Asp His Thr
        195                 200                 205 gtg aga taa                                                        633
Val Arg
    210

<210> SEQ ID NO 36
<211> LENGTH: 210
<212> TYPE: PRT
<213> ORGANISM: Arabidopsis thaliana
<220> FEATURE:
<221> NAME/KEY: MOD_RES
<222> LOCATION: (71)
<223> OTHER INFORMATION: AGL22 (SHORT VEGETATIVE PHASE (SVP))
<223> OTHER INFORMATION: Xaa = Phe or Leu

<400> SEQUENCE: 36

Met Ala Arg Glu Lys Ile Gln Ile Arg Lys Ile Asp Asn Ala Thr Ala
 1               5                  10                  15

Arg Gln Val Thr Phe Ser Lys Arg Arg Gly Leu Phe Lys Lys Ala
                20                  25                  30

Glu Glu Leu Ser Val Leu Cys Asp Ala Asp Val Ala Leu Ile Ile Phe
            35                  40                  45

Ser Ser Thr Gly Lys Leu Phe Glu Phe Cys Ser Ser Met Lys Glu
        50                  55                  60

Val Leu Glu Arg His Asn Xaa Gln Ser Lys Asn Leu Glu Lys Leu His
 65                  70                  75                  80

Gln Pro Ser Leu Glu Leu Gln Leu Val Glu Asn Ser Asp His Ala Arg
                85                  90                  95

Met Ser Lys Glu Ile Ala Asp Lys Ser His Arg Leu Arg Gln Met Arg
            100                 105                 110

Gly Glu Glu Leu Gln Gly Leu Asp Ile Glu Glu Leu Gln Gln Leu Glu
        115                 120                 125
```

```
Lys Ala Leu Glu Thr Gly Leu Thr Arg Val Ile Glu Thr Lys Ser Asp
    130                 135                 140

Lys Ile Met Ser Glu Ile Ser Glu Leu Gln Lys Lys Gly Met Gln Leu
145                 150                 155                 160

Met Asp Glu Asn Lys Arg Leu Arg Gln Gln Val Cys Val Leu Pro Ser
                165                 170                 175

Leu Leu Ile Thr Asn Pro Phe Leu Leu Ser Thr Ile Asn Val His Thr
            180                 185                 190

Pro Lys Phe Asn Pro Gln Leu Ser Thr Thr His Met Phe Asp His Thr
        195                 200                 205

Val Arg
    210

<210> SEQ ID NO 37
<211> LENGTH: 663
<212> TYPE: DNA
<213> ORGANISM: Arabidopsis thaliana
<220> FEATURE:
<221> NAME/KEY: CDS
<222> LOCATION: (1)..(663)
<223> OTHER INFORMATION: AGL24

<400> SEQUENCE: 37
```

| | | | | | | | | | | | | | | | | |
|---|---|---|---|---|---|---|---|---|---|---|---|---|---|---|---|---|
| atg gcg aga gag aag ata agg ata aag aag att gat aac ata aca gcg | | | | | | | | | | | | | | | | 48 |
| Met Ala Arg Glu Lys Ile Arg Ile Lys Lys Ile Asp Asn Ile Thr Ala | | | | | | | | | | | | | | | | |
| 1 | | | 5 | | | | | 10 | | | | | 15 | | | |
| aga caa gtt act ttc tca aag aga aga aga gga atc ttc aag aaa gcc | | | | | | | | | | | | | | | | 96 |
| Arg Gln Val Thr Phe Ser Lys Arg Arg Arg Gly Ile Phe Lys Lys Ala | | | | | | | | | | | | | | | | |
| | | | 20 | | | | | 25 | | | | | 30 | | | |
| gat gaa ctt tca gtt ctt tgc gat gct gat gtt gct ctc atc atc ttc | | | | | | | | | | | | | | | | 144 |
| Asp Glu Leu Ser Val Leu Cys Asp Ala Asp Val Ala Leu Ile Ile Phe | | | | | | | | | | | | | | | | |
| | | | | 35 | | | | | 40 | | | | | 45 | | |
| tct gcc acc gga aag ctc ttc gag ttc tcc agc tca aga atg aga gac | | | | | | | | | | | | | | | | 192 |
| Ser Ala Thr Gly Lys Leu Phe Glu Phe Ser Ser Ser Arg Met Arg Asp | | | | | | | | | | | | | | | | |
| | 50 | | | | | 55 | | | | | 60 | | | | | |
| ata ttg gga agg tat agt ctt cat gca agt aac atc aac aaa ttg atg | | | | | | | | | | | | | | | | 240 |
| Ile Leu Gly Arg Tyr Ser Leu His Ala Ser Asn Ile Asn Lys Leu Met | | | | | | | | | | | | | | | | |
| 65 | | | | | 70 | | | | | 75 | | | | | 80 | |
| gat cca cct tct act cat ctc cgg ctt gag aat tgt aac ctc tcc aga | | | | | | | | | | | | | | | | 288 |
| Asp Pro Pro Ser Thr His Leu Arg Leu Glu Asn Cys Asn Leu Ser Arg | | | | | | | | | | | | | | | | |
| | | | | 85 | | | | | 90 | | | | | 95 | | |
| cta agt aag gaa gtc gaa gac aaa acc aag cag cta cgg aaa ctg aga | | | | | | | | | | | | | | | | 336 |
| Leu Ser Lys Glu Val Glu Asp Lys Thr Lys Gln Leu Arg Lys Leu Arg | | | | | | | | | | | | | | | | |
| | | | 100 | | | | | 105 | | | | | 110 | | | |
| gga gag gat ctt gat gga ttg aac tta gaa gag ttg cag cgg ctg gag | | | | | | | | | | | | | | | | 384 |
| Gly Glu Asp Leu Asp Gly Leu Asn Leu Glu Glu Leu Gln Arg Leu Glu | | | | | | | | | | | | | | | | |
| | | | | 115 | | | | | 120 | | | | | 125 | | |
| aaa cta ctt gaa tcc gga ctt agc cgt gtg tct gaa aag aag ggc gag | | | | | | | | | | | | | | | | 432 |
| Lys Leu Leu Glu Ser Gly Leu Ser Arg Val Ser Glu Lys Lys Gly Glu | | | | | | | | | | | | | | | | |
| | 130 | | | | | 135 | | | | | 140 | | | | | |
| tgt gtg atg agc caa att ttc tca ctt gag aaa cgg gga tcg gaa ttg | | | | | | | | | | | | | | | | 480 |
| Cys Val Met Ser Gln Ile Phe Ser Leu Glu Lys Arg Gly Ser Glu Leu | | | | | | | | | | | | | | | | |
| 145 | | | | | 150 | | | | | 155 | | | | | 160 | |
| gtg gat gag aat aag aga ctg agg gat aaa cta gag acg ttg gaa agg | | | | | | | | | | | | | | | | 528 |
| Val Asp Glu Asn Lys Arg Leu Arg Asp Lys Leu Glu Thr Leu Glu Arg | | | | | | | | | | | | | | | | |
| | | | 165 | | | | | 170 | | | | | 175 | | | |
| gca aaa ctg acg acg ctt aaa gag gct ttg gag aca gag tcg gtg acc | | | | | | | | | | | | | | | | 576 |
| Ala Lys Leu Thr Thr Leu Lys Glu Ala Leu Glu Thr Glu Ser Val Thr | | | | | | | | | | | | | | | | |
| | | | | 180 | | | | | 185 | | | | | 190 | | |
| aca aat gtg tca agc tac gac agt gga act ccc ctt gag gat gac tcc | | | | | | | | | | | | | | | | 624 |
| Thr Asn Val Ser Ser Tyr Asp Ser Gly Thr Pro Leu Glu Asp Asp Ser | | | | | | | | | | | | | | | | |

```
Thr Asn Val Ser Ser Tyr Asp Ser Gly Thr Pro Leu Glu Asp Asp Ser
        195                 200                 205 gac act tcc ctg aag ctt ggg ctt cca tct tgg gaa tga                   663
Asp Thr Ser Leu Lys Leu Gly Leu Pro Ser Trp Glu
        210                 215                 220

<210> SEQ ID NO 38
<211> LENGTH: 220
<212> TYPE: PRT
<213> ORGANISM: Arabidopsis thaliana
<220> FEATURE:
<223> OTHER INFORMATION: AGL24

<400> SEQUENCE: 38

Met Ala Arg Glu Lys Ile Arg Ile Lys Lys Ile Asp Asn Ile Thr Ala
1               5                   10                  15

Arg Gln Val Thr Phe Ser Lys Arg Arg Gly Ile Phe Lys Lys Ala
            20                  25                  30

Asp Glu Leu Ser Val Leu Cys Asp Ala Asp Val Ala Leu Ile Ile Phe
        35                  40                  45

Ser Ala Thr Gly Lys Leu Phe Glu Phe Ser Ser Ser Arg Met Arg Asp
    50                  55                  60

Ile Leu Gly Arg Tyr Ser Leu His Ala Ser Asn Ile Asn Lys Leu Met
65                  70                  75                  80

Asp Pro Pro Ser Thr His Leu Arg Leu Glu Asn Cys Asn Leu Ser Arg
                85                  90                  95

Leu Ser Lys Glu Val Glu Asp Lys Thr Lys Gln Leu Arg Lys Leu Arg
            100                 105                 110

Gly Glu Asp Leu Asp Gly Leu Asn Leu Glu Glu Leu Gln Arg Leu Glu
        115                 120                 125

Lys Leu Leu Glu Ser Gly Leu Ser Arg Val Ser Glu Lys Lys Gly Glu
    130                 135                 140

Cys Val Met Ser Gln Ile Phe Ser Leu Glu Lys Arg Gly Ser Glu Leu
145                 150                 155                 160

Val Asp Glu Asn Lys Arg Leu Arg Asp Lys Leu Glu Thr Leu Glu Arg
                165                 170                 175

Ala Lys Leu Thr Thr Leu Lys Glu Ala Leu Glu Thr Glu Ser Val Thr
            180                 185                 190

Thr Asn Val Ser Ser Tyr Asp Ser Gly Thr Pro Leu Glu Asp Asp Ser
        195                 200                 205

Asp Thr Ser Leu Lys Leu Gly Leu Pro Ser Trp Glu
        210                 215                 220

<210> SEQ ID NO 39
<211> LENGTH: 687
<212> TYPE: DNA
<213> ORGANISM: Arabidopsis thaliana
<220> FEATURE:
<221> NAME/KEY: CDS
<222> LOCATION: (1)..(687)
<223> OTHER INFORMATION: AGL27

<400> SEQUENCE: 39 atg gga aga aga aaa atc gag atc aag cga atc gag aac aaa agc agt    48
Met Gly Arg Arg Lys Ile Glu Ile Lys Arg Ile Glu Asn Lys Ser Ser
1               5                   10                  15 cga caa gtc act ttc tcc aaa cga cgc aat ggt ctc atc gac aaa gct    96
Arg Gln Val Thr Phe Ser Lys Arg Arg Asn Gly Leu Ile Asp Lys Ala
            20                  25                  30
```

| | | |
|---|---|---|
| cga caa ctt tcg att ctc tgt gaa tcc tcc gtc gct gtt gtc gtc gta<br>Arg Gln Leu Ser Ile Leu Cys Glu Ser Ser Val Ala Val Val Val Val<br>             35                         40                        45 | | 144 |
| tct gcc tcc gga aaa ctc tat gac tct tcc tcc ggt gac gac att tcc<br>Ser Ala Ser Gly Lys Leu Tyr Asp Ser Ser Ser Gly Asp Asp Ile Ser<br> 50                       55                      60 | | 192 |
| aag atc att gat cgt tat gaa ata caa cat gct gat gaa ctt aga gcc<br>Lys Ile Ile Asp Arg Tyr Glu Ile Gln His Ala Asp Glu Leu Arg Ala<br>65                      70                       75                     80 | | 240 |
| tta gat ctt gaa gaa aaa att cag aat tat ctt cca cac aag gag tta<br>Leu Asp Leu Glu Glu Lys Ile Gln Asn Tyr Leu Pro His Lys Glu Leu<br>                    85                         90                     95 | | 288 |
| cta gaa aca gtc caa agc aag ctt gaa gaa cca aat gtc gat aat gta<br>Leu Glu Thr Val Gln Ser Lys Leu Glu Glu Pro Asn Val Asp Asn Val<br>                         100                       105                     110 | | 336 |
| agt gta gat tct cta att tct ctg gag gaa caa ctt gag act gct ctg<br>Ser Val Asp Ser Leu Ile Ser Leu Glu Glu Gln Leu Glu Thr Ala Leu<br>             115                       120                       125 | | 384 |
| tcc gta agt aga gct agg aag gca gaa ctg atg atg gag tat atc gag<br>Ser Val Ser Arg Ala Arg Lys Ala Glu Leu Met Met Glu Tyr Ile Glu<br>130                     135                       140 | | 432 |
| tcc ctt aaa gaa aag gag aaa ttg ctg aga gaa gag aac cag gtt ctg<br>Ser Leu Lys Glu Lys Glu Lys Leu Leu Arg Glu Glu Asn Gln Val Leu<br>145                     150                       155                   160 | | 480 |
| gct agc cag ctg tca gag aag aaa ggt atg tct cac cga tga aag ata<br>Ala Ser Gln Leu Ser Glu Lys Lys Gly Met Ser His Arg     Lys Ile<br>             165                       170                       175 | | 528 |
| ctc aaa acc cga tgg gaa aga ata cgt tgc tgg caa cag atg atg aga<br>Leu Lys Thr Arg Trp Glu Arg Ile Arg Cys Trp Gln Gln Met Met Arg<br>               180                       185                     190 | | 576 |
| gag gaa tgt ttc cgg gaa gta gct ccg gca aca aaa tac cgg aga ctc<br>Glu Glu Cys Phe Arg Glu Val Ala Pro Ala Thr Lys Tyr Arg Arg Leu<br>                   195                       200                     205 | | 624 |
| tcc cgc tgc tca att agc cac cat cat caa cgg ctg agt ttt cac ctt<br>Ser Arg Cys Ser Ile Ser His His His Gln Arg Leu Ser Phe His Leu<br>210                     215                       220 | | 672 |
| aaa ctc aaa gcc tga<br>Lys Leu Lys Ala<br>225 | | 687 |

<210> SEQ ID NO 40
<211> LENGTH: 173
<212> TYPE: PRT
<213> ORGANISM: Arabidopsis thaliana
<220> FEATURE:
<223> OTHER INFORMATION: AGL27

<400> SEQUENCE: 40

Met Gly Arg Arg Lys Ile Glu Ile Lys Arg Ile Glu Asn Lys Ser Ser
1                  5                    10                    15

Arg Gln Val Thr Phe Ser Lys Arg Arg Asn Gly Leu Ile Asp Lys Ala
                   20                    25                    30

Arg Gln Leu Ser Ile Leu Cys Glu Ser Ser Val Ala Val Val Val Val
             35                       40                    45

Ser Ala Ser Gly Lys Leu Tyr Asp Ser Ser Ser Gly Asp Asp Ile Ser
 50                      55                      60

Lys Ile Ile Asp Arg Tyr Glu Ile Gln His Ala Asp Glu Leu Arg Ala
65                      70                       75                     80

Leu Asp Leu Glu Glu Lys Ile Gln Asn Tyr Leu Pro His Lys Glu Leu
                    85                         90                     95

```
Leu Glu Thr Val Gln Ser Lys Leu Glu Glu Pro Asn Val Asp Asn Val
                100                 105                 110

Ser Val Asp Ser Leu Ile Ser Leu Glu Glu Gln Leu Glu Thr Ala Leu
            115                 120                 125

Ser Val Ser Arg Ala Arg Lys Ala Glu Leu Met Met Glu Tyr Ile Glu
        130                 135                 140

Ser Leu Lys Glu Lys Glu Lys Leu Leu Arg Glu Glu Asn Gln Val Leu
145                 150                 155                 160

Ala Ser Gln Leu Ser Glu Lys Lys Gly Met Ser His Arg
                165                 170

<210> SEQ ID NO 41
<211> LENGTH: 54
<212> TYPE: PRT
<213> ORGANISM: Arabidopsis thaliana
<220> FEATURE:
<223> OTHER INFORMATION: AGL27

<400> SEQUENCE: 41

Lys Ile Leu Lys Thr Arg Trp Glu Arg Ile Arg Cys Trp Gln Gln Met
 1               5                  10                  15

Met Arg Glu Glu Cys Phe Arg Glu Val Ala Pro Ala Thr Lys Tyr Arg
            20                  25                  30

Arg Leu Ser Arg Cys Ser Ile Ser His His Gln Arg Leu Ser Phe
        35                  40                  45

His Leu Lys Leu Lys Ala
    50

<210> SEQ ID NO 42
<211> LENGTH: 5171
<212> TYPE: DNA
<213> ORGANISM: Arabidopsis thaliana
<220> FEATURE:
<223> OTHER INFORMATION: SEP1 genomic sequence

<400> SEQUENCE: 42
cagatctctt ggcatgtgtc gaaaatgtgg agatcttaag aatgtagctt gtggccgttg      60
caaaggaaca ggaacaatca atcaggagg attctttggt ttcagtgact catcaaacac     120
aagatcagtg gcttgcgata attgccaagc caaaggttgt ttcccttgcc ctgaatgctc     180
aaaatcttga ccattttctc ggtatttat agttgtttca tcttcttgac actatgataa     240
gtgtaatcgg tccattggta atggtaatgt taaagttgaa gaatgtcttg tttattcgag     300
aagtctctta ttccaattct tgatctgtta ctgcaaataa ggcactttgc ttagatgtac     360
cggatgctta tgaattactg agtaggttaa ctttaaccgg gttttatcgt cattaaaccg     420
gagaaattca tctagtaacc aaatgctctg ctggaccttt ctttcagtga gcaactatag     480
gtgggttttt ggcagttgat gtaccataat tggtgcaaac acacattttt cttgaatttt     540
tgtttaactt aaataaagtt acttcgtttt cttgtttttt ttaatatgaa taaaaaaaat     600
caaccataac tgatagtagg ttggttatct ttatcaaaac aaataaagtt aataggcaga     660
aaaataattg tctatagaat caattatgaa aatgccattt tttgggatgg catttgtgga     720 ttttgcccctt tttttaatag tttgtgaatt ttgccatttt tcaggttacg tgaatgaata     780
tacgttttat tcattatgtt tgggtttact cggttgtggt tgttcttagg gtttagtatt     840
ttgtgtaaac tacgtatttt taccaaaaaa agtccgaaat ccatatattt ttaaatctta     900
gaaaatggct tatccgtaag atttagtaa aaatggcaat ttcaaaagat ctctataaaa     960
```

-continued

```
aatggcaaaa tcaacaataa tcccttgtct atatggtggt atttctgcta aaagtgactt    1020
atgggtagat ttttagctt catagattct ttgtcgaaaa aaaattactt tgtacatttt    1080
agtggagtta tttaaatttc ccaattgaac aaaaccatat attgatgaaa ttcgcaaatg    1140
caatccaaaa ataaatatgt tccactcttt tggttagctt ttaactaaag atgcgtttta    1200
ctttatgtaa gtggttgatc ttttggcaat gggggacaat gactatacaa tctaagagat    1260
cattttaacg aatatcattc atatttcatc ctcttcttca aatttcagtt tcactaatta    1320
accacgtttc aattgtagtg tatcgcgagc tgtaaatatt atctaattta tgttacataa    1380
tcataactgt aatctttatt agacaaaaac atatatacct cactgcaaac accttcaaac    1440
atggataact tgattaggc atacaaatat tatttctcat ttatttgata tgacctatat    1500
tatgtggcta ttttatcagt tttagtgttt tttatgataa ttgaaccact taaatgttta    1560
tctcattttt caatttattt taaactgaat taaaaagtaa gaaagtatga tccaataagg    1620
catcgacaca tggaaaccca ttttaaggta gaagatgctt ttctgcggct tctgaaaaca    1680
actagaaaat gatatgatac gttgctttca tttattgtaa gtattattta gttttaattc    1740
acgcgcttca tatccagctg caagactact acaacttgca attatgagac tctcgttaga    1800
aaattaccag gtataattta aaaacaaaaa gaactagaat atattggcaa ttatttgaag    1860
taagaaaata tgagattctt gaccgagttg ttaaactatc aaacccaaaa gttttggtta    1920
aaaaataagc tagtactatg tacatatgtt ttatgttgaa aatatattaa actgtatgta    1980
agagggagtg tactttcatt ttagatatac atttccagct agtacgaggt ctctatatat    2040
aaactttctt aatatcgcta aacaaatttt actttcaagt ttgtaatgtg ataagtgaaa    2100
gaccgtatat acatacacat gttaatcaac tgataacctt tgtgcctcgt gtgtctagtt    2160
actagtcaac catcaaacgt gcatgatgct gttttttctta gagtactatt gttgtgttat    2220
atataactaa acataaacaa tttgctatta tgatataaac atagaatttt caagcaatga    2280
tatgtttaga tgttttgtat aaatattcca taaatagtag acacccatat atacacaaac    2340
atgaattcta cctgaggaga aacacataga tgttcaaatt aaataataac cctataatga    2400
aaactctaaa gtaagtaata cgaaataaaa atttatcctt taaataacat ataaacatat    2460
atatacaagt ttaattggta attgtatcac aagagccaat tatttggtga ctgtatcaca    2520
cgtgcttaaa gagagcgtgg gaatgaaagt aaagaagaat aaagaagcag agagatgggc    2580
tagaaatgag aaaacacacc aaaccctaac ctcaccctca cacatttctt atcttttgct    2640
ctcaatagat tccattgatt caaaacaaaa ttttcattaa gatttcacaa cctccacaca    2700
cttccaaaca caattaaaga gaggaaaaag aatcaataac cctataaata aaaaatcaga    2760
caaacagaag tttcctcttc ttcttcctta agctagtacc ttttgttctt gaaattaggg    2820
ttaatttctt ttttccaaat accatcaatt ctccagacca taaaaactca aaaagatcag    2880
atctttcctc tgaaaagag atacccaact tatgttttg tgtgtctgta tatagataaa    2940
cattacatac ccatatttgt gtatagacat aaaaagtgga aattaaggta acaaaaagaa    3000
atgggaagag gaagagtaga gctgaagagg atagagaaca aaatcaacag acaagtaacg    3060
tttgcaaagc gtaggaacgg tttgttgaag aaagcttatg aattgtctgt tctctgtgat    3120
gctgaagttg ctctcatcat cttctccaac cgtggaaagc tctatgagtt ttgcagctcc    3180
tcaaagtaaa caactctctc actctttatc agtttcttga ttgagttttt gctagatctg    3240
agcttagatc tttgtctcaa ggacttgtta tatatagatc acacgatctt gatttctacg    3300
```

```
aagttgagtt aattagattt cttgatttca ttttctaggg ttttttttcca attcttgaaa    3360 tttaagatct ggttttttg ttgtcaatga tttagaactg tgaattttgt aatcgaatag      3420
attccaaatc ctgatatgca atctgaaaag ttttatataa ttaatatatg tctgtgtgat     3480
tggaaactta aaagttgttc acagatttct atgaaaatta caagtatcca acgtagaatg     3540
ataatatatg gttacatgca ttaaccattt gttagttcat catactttat ggtggttaaa    3600
acttcaaacg cgtgtatatc tgtgaaggct ttgattgttt gttttttctt aaaaacaatg    3660
tttaatagat ttttaattat atgttaaaat agttttgctt acatgcattc aagaaaatat    3720
agcgattaat tccttttttc aaatcacaat ttgtgaatca aacgaaaacg taagatattg    3780
cttgcaaatg ataggattga actattgata tttgtaaata taaatacgaa actttacgtt    3840
tgaaagttga aacaatcaaa tccaaatcaa ctcgtatata atcagataaa taatggaaac    3900
aatcttcaat tttgatggaa gaatacttta aaacttgaag agcttttttt ttatggtgat    3960
ttataggttt agatctccaa agtcaagtat gatcttttta ataaactctt attctctctt    4020
tttgagttat tttcagcatg ctcaagacac ttgatcggta ccagaaatgc agctatggat    4080
ccattgaagt caacaacaaa cctgccaaag aacttgaggt gttcttaatt caaatactat    4140
tttagattcc tatcatatca tttcaagaaa gatctttttt aaaagtttgt tttcgtgaaa    4200
tatttcagaa cagctacaga gaatatctga agcttaaggg tagatatgag aaccttcaac    4260
gtcaacagag gtacatatct gtctacctcc gtatatttac tcaattctgt atccatgtag    4320
attcatattt gtaggtgtgt gtggcttttg ttggtgcaga atcttcttg gggaggattt     4380 aggacctttg aattcaaagg agttagagca gcttgagcgt caactggacg gctctctcaa    4440
gcaagttcgg tccatcaagg tatctttata catggaatca atgattcaaa tgagattaat    4500
ttgtgttgtt taattataac tactatggtg gtatgatgat tgtttgcaga cacagtacat    4560
gcttgaccag ctctcggatc ttcaaaataa agagcaaatg ttgcttgaaa ccaatagagc    4620
tttggcaatg aaggtataat tacagaataa atgcatttgg tgccttgcga tcaatctctt    4680
tcacagagtt taagtttcta acatttttg gaaacatctc tagttttctt gtttctgatt     4740
atagtctttt ggtgaaatgt aaatgtttag ctggatgata tgattggtgt gagaagtcat    4800
catatgggag gaggaggagg atgggaaggt ggtgaacaga atgttaccta cgcgcatcat    4860
caagctcagt ctcagggact ataccagcct cttgaatgca atccaactct gcaaatgggg    4920
taaatccttt gccttaaaca atcatctgca aatcagcttg tgtacttcac tactaagatt    4980
gtacttatat aaggttcttt agttacttgg tgtaaagagg atcatcaatg tgtgtgaacc    5040
ttttaagttg ctgttttggt gatgatgatg atgatgacag gtatgataat ccggtatgct    5100
cagagcaaat aactgcgaca acccaagctc aggcgcagca gggaaacggt tacatcccgg    5160
ggtggatgct c                                                          5171
```

<210> SEQ ID NO 43  
<211> LENGTH: 5131  
<212> TYPE: DNA  
<213> ORGANISM: Arabidopsis thaliana  
<220> FEATURE:  
<223> OTHER INFORMATION: SEP2 genomic sequence

<400> SEQUENCE: 43

```
acgctctaac caactgagct aatgggccat ttgcgaatgg tagtgtctat tttacttatt      60
cgaatctaaa tcgtcatagg taattaagaa gacatgcaaa gcttaatcaa tgatggattc     120
tttgattcta cttctaggtg ccaccattga cgcattcata aaatcataac cggtcgttta    180
```

-continued

| | |
|---|---|
| caaaacatat tgcttgaatg attctaaaca aataatagtt ttttgttgaa attttcaaaa | 240 |
| catatgttag gtaaggtcag gttttgccaa taagccttac tatatacagt ggcaacatgt | 300 |
| ttcttctact ttggaggatt tgggtgaat atgaaaccca tgtgagcatg atacatgtgt | 360 |
| ttcttcttct attgaaattt cccccaatgg tcatttgctc tttgcgttcg tgttgcgctt | 420 |
| tccggtatca aatcatatat atatataacc taaatgagac tagacaattt gaatcattgt | 480 |
| aaaaggtata agaagagat tatagtccac aattaacaaa gtaataagac ggtaaaatat | 540 |
| caaacaaatt gaaagggtaa aaaaaaaaca agagggacaa gtcactgtta gaaaggtgac | 600 |
| tcctcccttt gggccagccc cctaccacaa aagtcaaagc ttacttacta ttcagtcata | 660 |
| tatcgacacg tgtacttcga accacatcac ccatcctatt acgtaatttc cactgtctag | 720 |
| acttttttt tttttttttt tttacttttt taacgttttt tagctgtctc tctaaattac | 780 |
| tacatacgga cttgctacgt cacctgagaa gaaagatctt tgctcgtaga ttctttgtct | 840 |
| gaaggaaaat tatttgtatt tagttatta caattgcata attgtgtgta gtaaatccgc | 900 |
| cagaatgata ttagagtgat actgagacga cgaatggtgt aacttgtaac atatatacta | 960 |
| ataaacacga ttgattaaaa atttactata cagtatatcc aaaacattat gattgagagt | 1020 |
| gtacatatac aataagtaat taaacctcaa aaccaaacag ttttttttt ttttggtcaa | 1080 |
| caataattag aaatgagaat aaactattta acttataaat tctagaccca aaaactcata | 1140 |
| ttttacccctt cttggtctca cctaaaaaga ctttaattcc caaaactctt gcaaacaatg | 1200 |
| gccaaacata gaagattgga aaacaaattt aaatctactt tcacttttat aaagaataat | 1260 |
| caacgaacca attaagttaa acctacatat attcgtatgt gatcacatat gtgttatatt | 1320 |
| cctcacgttc tcttccattt agctaataac cttaattact tcaagaaatc atatatcaac | 1380 |
| cgaaaactag taaataaat atacatactg aaagcgcgca aaattttag caatatttta | 1440 |
| aaataccccta catcatagtc ttaactaatt aatctttctg atcaaaattt attttcataa | 1500 |
| tattcataaa tacttatgga ttacctaaac caggatactt atccctataa atctgtcaat | 1560 |
| catcatggat tcatggagac atggtcagat atcccacgtc cagatacaat gtaacatatt | 1620 |
| gatatactgc ggctgattat tatttttttac attagaacga gtttagatcc aaaacaaaat | 1680 |
| tggtattctc aaacaaaaat taaaattga atacgaaagt aatagaacaa acttcaatg | 1740 |
| ttgtcgaata gataggaagc aatagaaag cgacacgtac atgtccattt taaggtagga | 1800 |
| gaggcttttc tgcggcttgt gaagtaagaa aagaaaatg atgatagctg ctttcgtttc | 1860 |
| attcattgca gaagaaacca atgtttcccc aatctcacgc gcctcctcct atctaccacc | 1920 |
| acttggacaa atcccctttt cagtattagt tttttttcc ggacattgta cattcaaaag | 1980 |
| cattccaagt gtctaataaa cataactaac cactccaaga tgcaaaatct agctacgaac | 2040 |
| aaattttaaa ctatagagat gaactttaaa ttcgggcatt aattagtgga acttgagcta | 2100 |
| ttgatgagtt ttctgacttt ttgaagctta attgagtttt atatacacta tatataggct | 2160 |
| tgtaataata tggatcaaac aagaaatata taaactacaa attgggaatt aggttttaaa | 2220 |
| acgttatcgt tctatttaa ttcaggcacc tttagaatat caagatccat gcatgtttca | 2280 |
| atatttctgt tgacaaataa ataaagatgt ctcaaatatg aagtttgggc aacgtacgtg | 2340 |
| tagacctaaa agagtcgaaa cattggtatc taagtcatat atctagatgt atatggacat | 2400 |
| ggattatata actagacaac gtttgttttta aaaacttaat tcattttct taattagtag | 2460 |
| caactagcaa ctaactactc atggcaaata atggtgtctg cgtggcacgc acttgggaga | 2520 |

-continued

```
gaaggtgtga gaatgttttt tactttctgt gtaaaagatg gaagagagag aaagagtaaa    2580
gaagtagaga gagagatatt gtatcaccaa accctaatga tctctcaccc tcacaaattt    2640
tcttatcttt atagctttta tagattcaca aaaacttttc ttcagattca caatctcatc    2700
acaacccttc aaaagagaa aagatctaaa gaataaacaa gagccctaat atcaaatcac    2760
aaccaaaaaa accaagaaaa gctaattaaa gttttctctc tagctattcc tcttcttttc    2820
ttgttcttga aaactagggt ttacttcacc aaaagataag atctttcccc agaaaaagca    2880
atacccaagt catgtttctg tgtgtctgta tatagataaa acattacata ccctaataag    2940
gttacacaaa tagctataaa agagggaaaa taagataggg attttttggg gtgaggaaag    3000
atgggaagag gaagagtaga gctcaagagg atagagaaca aaatcaacag acaagtgacg    3060
tttgctaaac gtagaaatgg tttgctgaaa aaagcttatg agctttctgt tctctgcgat    3120
gctgaagtct ctctcatcgt cttctccaac cgtggcaagc tctacgagtt ctgcagcacc    3180
tccaagtact tctctttctt tatacactta ttagatctgt gtgtagatct ttcattttc    3240 tagtcttgtg atgagtttta tctttcttga ttgcttttta acaaaatact tgatatattt    3300
tcagtttctt aatctgatct ctaattaggt tttgattata aagaataat tcagtacttt    3360 caagtgattg aatttcgaga tctgatctta atttaatcat catgtcaaat tcttagggat    3420
ttaattgcaa tctatttta gatttatcgg agctaggaaa gtatcataat gatatactat    3480
tattatcatg taatttcatt gtctctacac ggatatatat gtgattagaa cttggtaaag    3540
taaactaaag attcacagtc ttcaatgaaa tttaaaagat ccaacgtaga ataattagtg    3600
gttccatgca ttaaccagtc taattaaagc tcatgcagac atttaagcac cacatgaatt    3660
taatatcttt ttaattaagg gatcttcttt ttataaattt tcttttgtta gttttaaaa    3720 ttttagtttg ttcattaaat ttatagattc ttcttctcct gatttgtgtt tttgatctt    3780 tcagcatgct caagacactg gaaaggtatc agaagtgtag ctatggctcc attgaagtca    3840
acaacaaacc tgctaaagag cttgaggttt aatctccaac atctcttcga tcttaattat    3900
ttatcctttt ttaattttat ctaaagaaaa tgtttgattt tgagacaaaa gcccttcaaa    3960
gtttcttaca tagatattca attgtctatt atcttcgcaa ttttcagaac agctacagag    4020
agtacttgaa gctgaaaggt agatatgaaa atctgcaacg tcagcagagg tatatacatt    4080
aatgtggatg atgatcattt ataaacagca tatatatata tatatatata tatatatata    4140
gtttgtattg atcatgaaag tgtgttgctg cagaaatctt cttggagagg atcttggacc    4200
tctgaattca aaggagctag agcagcttga gcgtcaacta gacggctctc tgaagcaagt    4260
tcgctgcatc aaggtgattt acttctgtac atacactgaa agattcacac aaatctttct    4320
ctatatatag actgagacac atgcatgaaa tgtttttgat gcgtgaggtt atctgaaaat    4380
gcctcttctt ttttgcagac acagtatatg cttgaccagc tctctgatct tcaaggtaag    4440
gagcatatct tgcttgatgc caacagagct ttgtcaatga aggtatatga tgatgtttct    4500
ctctctctcc tccagtttct atttatagat ggaaacttta aatagtccaa tttatatata    4560
tgagtctaaa tttcacattc ttcaactgct acatgtttct tttgtattat ttctatgata    4620
tcttcaggaa agtttgaaaa atattgtgtt tgtttagct ggaagatatg atcggcgtga    4680
gacatcacca tataggagga ggatgggaag gtggtgatca acagaatatt gcctatggac    4740
atcctcaggc tcattctcag ggactatacc aatctcttga atgtgatccc actttgcaaa    4800
ttgggtaaat caaacaactt ttcttgcctt aagacatcaa cttaggttat aaacagttag    4860
cagtttgctt taagcccaac attgtctttg tttcatagag gctttggtta aaactcgtgt    4920
```

-continued

```
tgtttagtct aaggattcag cactttgatg tctgaagtat ggaaaatcaa tatctcagac    4980
ttgaaaatgt gggtttctat tgttgacttc gaaactatgt tgttgtggtg ttgcaaacag    5040
atatagccat ccagtgtgct cagagcaaat ggctgtgacg gtgcaaggtc agtcccaaca    5100
aggaaacggc tacatccctg ctggatgctg                                    5131
```

<210> SEQ ID NO 44
<211> LENGTH: 5070
<212> TYPE: DNA
<213> ORGANISM: Arabidopsis thaliana
<220> FEATURE:
<223> OTHER INFORMATION: SEP3 genomic sequence

<400> SEQUENCE: 44

```
gtccccttcc cattacgtct tgacgtggac cctgtccgtc tatttttagc agattaatcc      60
aacggttctt attctttctt cgacccttca cgacattgcc tcaaagccgt ccgattctca     120
tctcacgccc aatggaccac atatatcacc agtactccgc aacttagctg tcgtgtagga     180
tttcacgtgg catttatttg ttctagtttg tagtgcaaac attgcaagtt gatatggtcc     240
cctatcgatc accgtcgtct ctttagcttc acatcgagat tcttctttct ttcctacgtg     300
taatagcatt tttgattttg agaatttctt tagaaccgtt ggatctctca tcgttggttg     360
atccatccat ccaaatggga cctgtgtgtg ctccatccag ggcatatgat cccaaagcca     420
aaagagtatt tccaagtgct ttctttcttt ctttctttct ttcttactaa ccttttttt      480
tcttatgctt tagactaaga aatttattcg gccatatcca cttttacgaa tatacttctt     540
acaagatcta gattttttg agttaattcg gtgtatataa cattggcatg gactgcaatt     600
aagtaatggt aatgtgatca tgatgcgatg tgtcgttatc agtagtataa tattgatggg     660
ctaccctgga aaacaaaatt acgtgttata tgtacacaat ttggtagaac cgtagaaatt     720
aaactgaata aaaccttcta taatgttcaa aattatatgg tacagattaa tacggaaaaa     780
cattcacgct ttacgtaaca attaagtgga agtaaaatt atcccaaaaa tatttatatc      840
acatcattgt tatatttcta agtttttta tatctctaat ggtatatgtt ttacagattg      900
tttttttggga aaattcttaa agagacttga agaatgtttt tttttattt tcttgaaatg     960
tttgacactt gaaaccgttt aaaaactcaa atatagtata tatcattgtt ggtctctac    1020
cttgtaattc accacatata ttatcaatgg ggaagatttg aaaattttg ggggatcaca    1080
aaacgaagga aagagtacaa aaagagaagg aaaagataga agatatatgt ttttaacttc    1140
attggtatga catcaataaa taaatagttg aatgtacttt agtttctctt ttggtttaat    1200
gcacatcatc tcgatcaatt gtcatcatct tacattgaat tatacgacca gatctgataa    1260
caagtgaatt cgtacttgcc cttcccttc ttctcatacg tccttctaac taattttgat    1320
tgtaacttat aattatataa ccatatttaa ttttatttta tctaaaacca attgaagcaa    1380
attaaaatat cataaatctt gagtcccaca tgaagacaat atataaaact cgtgcaaatt    1440
tgcttaaaat gcttctatga gaccatgacc aagtgagatt aataagcgat tcaatgtgca    1500
aatcaaaaga gaaagaagc taatgggttt aaatataacc aaacagaata ataatgctat    1560
gtttagtttt tctaattgaa tcataccttt gtgtccatca cctacttacc ggtcagaata    1620
aagcaattac gtctgcaacc aaaaagcact aagactttcg gtcagacatg atctctaaca    1680
tcggacgaac cctaagataa ccaaaataaa ctatatctta tattcaaatc tctgtttatt    1740
ttatccattt atgttttctt tctttcccat aatttttttt gtgtctcatc agactctctt    1800
```

```
accaaactga atttatcaac atggttttt ttttggccac atcaaaatgg tggtttataa   1860
agtagactaa tacaaaagac atttctgtta atttcactaa caaaaataat cttagcagta   1920
ctatagattg gaaaaggaaa agcaaatcta gcagtaagat ttatcaaaac tagcagtaag   1980
agttttagat atcatgaaaa catcacaaac gagtagtgtt ttactttaca tttttaacca   2040
atcacaaggg tagttccgta agttgggaaa atcgtacgag gcttcaccta gttaaggtta   2100
ggtcacatga ttccctgaac tcgattttat aagtaaaaaa gaaaaattta taaaatcaaa   2160
attttttata taaaaaaatc aggtggattt atcagaccct accatcgaga tgtcgacacg   2220
tgtccaaact cattcattgc cctactattt tctgtttagg gttgcaatca ctcatcgcac   2280
acgcgccatc tccaccttcc attattaatc tctcattttc aacatcacac tcttacgaat   2340
catacgattt taatatctct gtctctctca acgtattaaa taaaaatggt tttaaatgtt   2400
agggtttttt gtaggatttt caattattaa tctctataat tcgatgaact aagtaaaaaa   2460
gcatcaaact ttcttggcag atcacatttt tctctaaact aaatatggac tgaaattgaa   2520
aaattaaacc actagctaga ataaagtgtt ggtgagagtg gaactctaat ttctctcctt   2580
tactaattat gtataaacac aaaaatgcac caaatttta ggtttgaaaa tatctaagca   2640
tggatagggt aattaacatt ttttctttca attttgcaat atttgaataa atcctatgag   2700
ggtctttggt acacaataat tggagggtat atagttgagt ctgagagtat attagaaaga   2760
gaatatttca agtaatgaag ctgacatgtt tatatgtact ttgagagaag tgttgtgaga   2820
tttgtacaaa tgtatatgta cactttaaaa agcaatataa gatagataaa aaaaatataa   2880
agaaaaaaag aaagaaagaa agaaagaaag agagaggctc atatatatat agaattgctt   2940
gcaaggaaag agagagagag agattgagat atcttttggg agaggagaaa gaaaagaaa   3000
atgggaagag ggagagtaga attgaagagg atagagaaca agatcaatag gcaagtgacg   3060
tttgcaaaga gaaggaatgg tcttttgaag aaagcatacg agctttcagt tctatgtgat   3120
gcagaagttg ctctcatcat cttctcaaat agaggaaagc tgtacgagtt ttgcagtagt   3180
tcgaggtata tatctacttt tgtatatata ttacttataa cataaacatt ttatatacat   3240
attaagtaac acaaaaatgt cttgtatgta tgggtctctc tgtgatgtgt tgttgtgtcg   3300
tacgtacgtg ttctatcata tccttttaaa agaagcaaag aggaaaaaaa atttgggata   3360
ccccaaatct gtatcatttt ataacaagtt tgcttttttg atgttctttt gtgtttctct   3420
ttgatttcca tttttgtttt tgattttttt tctatttctc tttacatcta tcaaagtttt   3480
ttttcttata ttttattgct tatttgtttg tctacttaat tcacattatc tgagagaaga   3540
acaatctatc tgatatgaaa ttagggttaa tttctcttgt gagtactctt taattcacat   3600
aagcttaaag tttccacctt tgattctgg gggtcgtcca attcgatcaa atcactcaat   3660
tttgttgtca gattgatata agttcatagg gggatattgt ttccacgaca atccattta   3720
gtaacccta ggggtttcca attttgggtt ttgaattgac gctaatgtca aattcatcta   3780
aagtccgttg gatatgtata cttggggatg ggattcatcc ttttttctgg gttctttaga   3840
tcttctctta aaagactaac agattttgtt gtaaacccta ggaaacagtt aaaaatccca   3900
tttttaaaaa catgttttga acttgatgag taagattaat ggaagaaatg atgttttgt   3960
gtggtgtgaa gcatgcttcg gacactggag aggtaccaaa agtgtaacta tggagcacca   4020
gaacccaatg tgccttcaag agaggcctta gcagttgtac ccaattctct tctctttctt   4080
ctaattacct taattaatta ctctcaattt ttactttgat ttttagagtc aaatgattaa   4140
tgttataatt tgtcatatac ttcaggaact tagtagccag caggagtatc tcaagcttaa   4200
```

-continued

```
ggagcgttat gacgccttac agagaaccca aagtaaaact aattagcttc ttcagctacc    4260
ttcagagagt gtttgttttt ttagtagatt tttttgatgg ttttgatgtt gaaataggaa    4320
tctgttggga gaagatcttg gacctctaag tacaaaggag cttgagtcac ttgagagaca    4380
gcttgattct tccttgaagc agatcagagc tctcagggta ctactttgtt catcaatatc    4440
tttatacact gatctatttc catagtaaga ttaaatttgg tgtttaattc tgcagacaca    4500
gtttatgctt gaccagctca acgatcttca gagtaaggta aataaagaaa cactcattct    4560
cctctctaaa ttcctcatct aaaagtaatg taaccaagaa aacacaaata tttggagcag    4620
gaacgcatgc tgactgagac aaataaaaact ctaagactaa gggtaattaa tatacattct    4680
catatcacca aattaatgca tcactaaatt tggttataat gtgtgtgtgt atatacatat    4740
gtgacagtta gctgatgggt atcagatgcc actccagctg aaccctaacc aagaagaggt    4800
tgatcactac ggtcgtcatc atcatcaaca acaacaacac tcccaagctt tcttccagcc    4860 tttgaatgt gaacccattc ttcagatcgg gtaactttag actagtataa ccaatttgat    4920
ttgagttcta ttataagctt ttcttaagaa agtatctcaa actactaaat tttatggagc    4980
aggtatcagg ggcaacaaga tggaatggga gcaggaccaa gtgtgaataa ttacatgttg    5040
ggttggttac cttatgacac caactctatt                                    5070
```

<210> SEQ ID NO 45
<211> LENGTH: 5392
<212> TYPE: DNA
<213> ORGANISM: Arabidopsis thaliana
<220> FEATURE:
<223> OTHER INFORMATION: AGL20 (SUPPRESSOR OF CONSTANS (CO) OVEREXPRESSION
    1 (SOC1)) genomic sequence

<400> SEQUENCE: 45

```
gaaaaaaaaa acacctaaag aagtgaatat aataggcata tacatatgag gaaaatgaaa      60
acaaaaggag cgaaaaatag atttaaccta aagaggaag taagagggtt ataagaggta     120
agaaaagtag gaccatataa tagctatatt gtagaatttt attatttgga gatatggcaa     180 ttttttgtgag ggtcccatga agactaaagt gtggagcacg atttatcttt gtaattaata    240
aaataataaa tatattatta ttgtctcggg attttttcgat tgatgagaaa aagtaagagg    300
tgcgttttcg aattatcatt ggctaacgtt tgtacgtgac tgtacggacg acgttgatgt    360
atttctaata ttgtactctt ttttcccacc cttatttctc taattcttgt acattaaccc    420
caaactaatt ttacaaacac attggtgttt aatcattgtg aaattttgat ttatctaaaa    480
tacactttat atgttatgat tttgcatgag cttatgactg gtaaactcat gagatttcca    540
tatcaccatg ttggaagtta ctaaccatac atcttttaaa tgcaaattca catcattcct    600
agactgctag acagacatgt acttacttat acaaggtttt tctaatctaa tggcaacaaa    660
gaaacttgtg actaaacgca tacgtatctc tcatatagtg tagactagaa ctctacgtat    720
ctctcatata gtcatatttt taaaaaaatt atactttggg atctcgaagc gaaaattaga    780
ttagtttata tgattatgta caaaaaaaat cggatattac taccacttaa aaataattgt    840
agtggtcaat catatctaaa attaatcgca gtgaacaaaa acctgaagca tagcctggtt    900
ctatcttact ttcgatgtga cacattacta acacgattgt tttaatctat aggacgaatc    960 cttttaagtaa tgtatagttg gttcagttac gttagatact ttttgttttg gatttgtctc   1020
aaccagttaa gaagtgatcg tatttactag tggtatacga tgatgtttct ttaaatctga   1080
```

-continued

```
attgggtcta caaaatacat aactaaactt caaaccgggt ttatacttta tacaaacacg      1140
aaaatataaa gatagagaca attcaccaga gaagatgtgt atttatataa aaattatcca      1200
tacagatttt cggacctatc tgtttgatat ttaatatata taaatacgtt aacatatttc      1260
accagagaag atgtgtattt ttcgaaataa ttagtttgtg tggtcctcct cccgatatag      1320 ataaagatc attagatatc gattaacaat tttatctcca aaaaggata ttttttggt        1380 gccactagct agacaagacg ttcgataagc tgaattatta ttggatttct aagttacgtt     1440
ttctttagta atccgaggga ccaaaaatag caaatgcctc tttagacacg tcgctactta    1500
acgccattgc cccattgtct ctgtactagc ctccaaatat ttggattaat ggtcacttag    1560
gtaatgagga aattgtagta ttttgtaatg tggttttgtc caacttataa aaacttacaa    1620
ttgcaagtaa ttaattattc acatggagat gtaagattat gtcatataac taaaaacaca    1680
atttaagaac aacaataaga aacaatggac aaacaagcat agaaaatata caaatcaaat    1740
gaattttatc tgttgggatg gaaagatatt ataaaaattg attaaaacca atatagttgt    1800
attactcaca ggtaagaaaa aacgatattc ttatttttca tatcaattac aagtgggggc    1860
atataggtac gagagagtgt ttgtgtccac attaaaaaca aaaaaagatt tttgttagaa    1920
gaaatttaat aaaaataatt tgacaggcat ttccatccaa ctagatattt atgggaggga    1980
aaaagatgtg tatgtaaaaa tgtccatatg tatcaaaata tgctattttt ggtctttctt     2040
aaggcttttt tccaaaataa gtaaaggatg aggtttcaag cgtccatcat atttgcgaca    2100
catatgactg actatttagc tcctccctct ttctttctct tatttttatta tctttctcca    2160 agaaataaaa tagaaaagaa aatatatatg gtttcacaaa caccattacc ataactacaa    2220
cgagaagagg atctttttta aggagaaaag cagagagaga agagacgagt gtgtgaagtt    2280
tttttgtctt ttgtttcttt tattacacac aaatagatga aacgaggaaa gctacttctt    2340
ttgctacttc cataaaaagg ttcttccttt cgcagagaat caactttgat catcttcttc    2400 cttctcttc tttcttcttc tccctccagt aatgcttata tagtctcctc ctatatctct     2460
acctatacat acacaaaccc tttatcctcg aaagcttcct cctggttagg tttttatcaa    2520
acccttttag ccaatcggta agatctcttc gtcatgatct tttctttttt cttttgcttt    2580
gtactctgat ggatctataa acttatatgg gtttggtttc atttggttcg atttgatgtg    2640 tttggttct ttgtcctaaa tctcatgaaa ggaggttgca tccttcaatt aaaccgataa     2700
caaaagtttc cattacagac ttatagatca gatactttag attgttttgc ttttggggta    2760
cttaatcttt cgttgacttc atcagtcttc tcccacccaa acaaaaaagt catatttcga    2820
tcatatcttc atttttttaa cctactctct ttgattcata tatgaaatgg gttgttttat    2880
gtgtgtgact aatcttgtta ttgaggtggt tgcaccattg atctaccgtt ttcttcaatt    2940
tttgaaaaaa taattttatt ttttttctgt gtgcaaggga aattaactaa agaagaagat    3000
atggtgaggg gcaaaactca gatgaagaga atagagaatg caacaagcag acaagtgact    3060
ttctccaaaa gaaggaatgg tttgttgaag aaagcctttg agctctcagt gctttgtgat    3120
gctgaagttt ctcttatcat cttctctcct aaaggcaaac tttatgaatt cgccagctcc    3180
aagtacgttc ttttttgtctt tcttacaaat catccataga aagagagaga gagagagatc    3240
tcattaacct ctctatttgt atcttaattt tttttggttt atatatggat ttgattggcc    3300
ttttgtggaa tcacatctct ttgacgtttg ctttgagagg tgtgtttaaa tgagtttctt    3360
ggtttctgca aaaattagggc tattattaaa gtagtatcaa gtacatatac cctcttattt    3420 attgttttt tatttccgct agtatatcat cttgtttaat catctgtctc tctctttctc     3480
```

-continued

| | |
|---|---|
| aattagtttc tcaagttatg atataaataa aatgtgctct ttcgtagcca atttacactt | 3540 |
| gttatatatt tgatcttctt agagatcatg atcacatagt attaataaaa caactttcaa | 3600 |
| ttagtattct tttggtttga actaatcttt gtcttgttat tgctttaagc aaaacatgtt | 3660 |
| gttctaattt ctaagtgatg attaggaagt tgtttcatca ttcctgattt attaatccct | 3720 |
| catgcttcat ttcatgctca ttcctaattt agttcaattt gtttgaatat tgttcctga | 3780 |
| ttttgacata gaaactcaaa gctagctagc caaacctaaa tgttgattgt ttttgagaat | 3840 |
| caaaagagtt ttatcttgta ctgttaggta gtagggaaac caaacttact tttgatgaat | 3900 |
| cattacttct gtaaatgaaa atgccagctt tgatcagat gtttcagaca tttggtccat | 3960 |
| ttgggaaagt acttctttct ctcgaaccta ctaaatataa agataagacc tcacatgttt | 4020 |
| ttgattttct aaaatagggg gaaaaagtac aagactttc aagctatgtc cttgattaag | 4080 |
| tctagtgata tcttcaataa gaaatgtttt gagaacacca ttgggatcta aatttgatct | 4140 |
| ctgatgattt actttaatgt tccaattata tatgttttg acagtatgca agataccata | 4200 |
| gatcgttatc tgaggcatac taaggatcga gtcagcacca accggtttc tgaagaaaat | 4260 |
| atgcaggttt attcttatg atcttcttgc ctatatatca attcttgcta attaatactt | 4320 |
| ttactatata atatcaaaga gcggtaatga atataaccac aatatgtata taatctcaag | 4380 |
| gtcacaggat caagtcacat atttataatt aggatatata tgtacatgca ataacatttc | 4440 |
| tgtgatataa ccaacagcat ttgaaatatg aagcagcaaa catgatgaag aaaattgaac | 4500 |
| aactcgaagc ttctaaacgg tttgtgatat atacatatat acaaacacat tattcatcac | 4560 |
| ttgtatatat ctatttcatg atgcatagga gagtttgatc aattagtgtt ttgttttgt | 4620 |
| aatcagtaaa ctcttgggag aaggcatagg aacatgctca atcgaggagc tgcaacagat | 4680 |
| tgagcaacag cttgagaaaa gtgtcaaatg tattcgagca agaaaggtat gtgtatatat | 4740 |
| ttatctgtta tatctccaca ttataagtat tgttcgaatc atcttctgaa accactcata | 4800 |
| attataactc aatttctcat ctcttttaga ctcaagtgtt taaggaacaa attgagcagc | 4860 |
| tcaagcaaaa ggtaaagtag ttttttatgag tgtatataaa cagatataag tatgtatgca | 4920 |
| aattgtgtaa tattccaagt aagtaagcct cttgtgcttg cttttttacaa attggaatct | 4980 |
| aaaacttttg caggagaaag ctctagctgc agaaaacgag aagctctctg aaaaggtata | 5040 |
| atatattctt atgggtctca agttagggtt gcacattcgt ttttttattc ggtaaagata | 5100 |
| agaaagttgg ggttctttttt gggggttatt aggttaggag agtccttact agttttttctt | 5160 |
| ggttatcttc aatcatcaac cttctttaat ttatgtattg ttctatatat cttctaatttt | 5220 |
| gcatctatta atttttgtgta ataattctat ttgaatgcag tgggatctc atgaaagcga | 5280 |
| agtttggtca aataagaatc aagaaagtac tggaagaggt gatgaagaga gtagcccaag | 5340 |
| ttctgaagta gagacgcaat tgttcattgg gttaccttgt tcttcaagaa ag | 5392 |

<210> SEQ ID NO 46
<211> LENGTH: 5134
<212> TYPE: DNA
<213> ORGANISM: Arabidopsis thaliana
<220> FEATURE:
<223> OTHER INFORMATION: AGL22 (SHORT VEGETATIVE PHASE (SVP)) genomic
      sequence

<400> SEQUENCE: 46

| | |
|---|---|
| tacaagtcat cgccgccgtc gtcatttca ggatccggcg agaaactgaa ccaaaataat | 60 |
| acttattta ctcgtaagga aaatttgggc ctaataaaag cccaataata ataaaaagcc | 120 |

-continued

```
cattagggac tccgctttat gataacggtg actgtagttt ccttgatgtg tcagagagag    180
tgtgtagtgt agggactgtg tagaaagaaa gaagcctaaa atggctaaaa ggttaggtgc    240
aatgtttcat tagagaggct tggaactgtt aagggaaagg tcacgagtcg tctactcata    300
aaaactctga cactttgacc aatcaaaact caaagacctc accagttgtg tcacgtgcgc    360
ctctaaacac tattcaattt caaatataaa tgattcatgc ggttccaaac gccaattgat    420
ggatgttcta ccaaatttaa tctacttttta ccaaccatg acaaatatga ataaacatta    480
cttgataata atttttgtgag tgaacaaact ttttttttt cgaaaccaaa ccaagctgaa    540
aaaaactcaa cgattttctt tgtttaaaat acgttagaaa ggaatatgta ttatgccgaa    600
ataagtaata tcgatcaggc cacctctctt atagttattc tcctagcaac tttaaccact    660
agaaggtttt gttttctagt gttttctaat atacgtcatc aaaattttca aaaaatacta    720
cattttgtt ttaaaaactt ccataattcc attactcgta gaacacaaac gcaaaccata    780
ttaatatttt gttgtcaaca aaatttcaa attataattc aactatattt gcttgattac    840
ccaattagat agaaaagagt taagaagaa aagaaaagag tttacagtaa attaacgcaa    900
accataatta tatttaacac cgtattaatc acatcaacca tatgactttt ttaccgtttg    960
caacttcata attcatatag tatcataata aattcgcaat aatacaacac aagagtttcg    1020
tcggaagagt aaataatact caaatagggg gtgagtgata cgagccacat gtattcttga    1080
agggtagatt attgcaaact tggagtaata aagagaagaa gaatgggttt gtagtagttg    1140
cgtggagtat ctttatttgg gtaaaacttt aatttagaaa taaaattctg tacggacaat    1200
ggatcgtgtc ccaatcagat ttcttgtggc tgcttcgggt ctggttttgg gtcccttttga   1260
aaaatttttag tggtcgacac tttttatttt actctggctc gtgcctcgag ggtccctcta   1320
ttcactgttt cttcgtatga aggtatgctt aaacattatt ttatttttaa aaacccttta   1380
attttatttt cttacccttta atcacggttt tgtaaattgc ttttttagtct atggaatgat   1440
gattgtggcg attgaaatca tatgtttggt tctgttgttg acgttggtga agtatatgtg   1500
atttgtaatg ttgagcttat gtattaaaat gttaaatgat aaataacctc gtaagaaagt   1560
gatttcattt aaattttatt ttgagttaca tattcaattg gttttataaa aaaatacttc   1620
agtgatgatt gataccccca ttgtgtgtgt aattgttact gggattgaac aaaatttat    1680
tgtgcatgac aaactttcca aattagtgca tagattgtaa ttgtataatg gactacatgt   1740
atctgagtag atatggttca ttaggttaca aacctctttt tttaaggaca caattttcg    1800
acaagttata tgccacatga ttgactacta aattttcaaa aattattgca ctaatgtctt   1860
tgaaattaac aaaattatttt gtcatttccg agttggattc ttacaaacca aggccgaact   1920
cacaaactta tttctttcag taaaaacaaa acattgtcct cagaaaaatt ctgaaatgtc   1980
atcttcccaa atgttttac ataaataaaa ataatataca gttgatatta ttttgttctt    2040
tctgaatttt gttatgaggt accattacca tatagtacgt agatttacaa aaatgaaaat   2100
acgttgtagc ccttgatgtt cttcaggtct tctagttagt ttttgcagta ataccaacc    2160
aattagttac aaggagtata agtgaacaaa gtgagacaac tcattttatg cttccctata   2220
aaagaaattt ccccactgac ccaaacacac acttctcttc tctctctcat ctcattggag   2280
acttataaat cctattacct caccatatcc aataaccacc acacacagac caatatccaa   2340
aaaaaaaact aaaactaaaa atataatata tatcgttttc tttccaaaaa taatcattta   2400
agaaacccca tcatcttgat agtattataa aattaataaa cctctccctg aaaatatctc   2460
```

```
atccttcacc aatcaaaacc ttctcatgtc ttcttctctc ctcgaccttt gaggtggaaa    2520
attaaatata ttcccttagc ttttttttctc ctttagtttt cttcttcttc ttgagttttt    2580
tttcttttga tcctctctaa tttccttgtt gattcatcga ctagatctaa ttcttctcac    2640
aaaagactga gtgtgttctt tctttcaaat cttttcaaaaa ctagggtttt tactgtcttg    2700
aaatcatatt tattcttcta aatttagcaa aaagaacacg atttactttc catttcagtc    2760
gtcttgtcac tctctctctc ttctttaaag tctcccttttt tagcaaaaat tctctctctc    2820
acaaaattta tttcctctgg cttcttcttc ctcctcctcc atctcttctc tttactctct    2880
ctttaatcat ctctcattct tgaatcttga tccatcaaaa tcaatcccgt tctcgaaaga    2940
tccattaaaa tcaaaaccta agctctctct cttgcttcta gggttttttt gttcgttgtg    3000
atggcgagag aaaagattca gatcaggaag atcgacaacg caacggcgag acaagtgacg    3060
ttttcgaaac gaagaagagg gcttttcaag aaagctgaag aactctccgt tctctgcgac    3120
gccgatgtcg ctctcatcat cttctcttcc accggaaaac tgttcgagtt ctgtagctcc    3180
aggtctttct ttctctctct aacttccctc tctatagatt tctcataact catcgaagga    3240
atcttgtcta gatccagaca aaaaacttta aagagttttt agatgtatat ctgatacata    3300
ggagtttact gtatcaatct ttataggacc actaactatt tatataatta aaatagttgt    3360
tagaaacatt aatcatgacc ataaatgaca tatataaagt gtagtaaaa actctgtatt    3420 tagataaatt aaggtatcta actacggtaa tattcaaaaa gatgtaaatc tggatatgca    3480
tatatgtata ttattagtat ataaatacat gctctatagt aggtatttgt gtcaaccatg    3540
tataaatcta tgtatataga tattgtggta tgatatgttt aagccgtcaa tgtcatattt    3600
atatagaaat atgtgggtac cataacatga ggaagtatct atatgtgtgg atgtataaag    3660
ctttcccttt gaagaagtaa tctaaaaata atatatatat atatatgtat atgtatagat    3720
atgttggaat cttttattagt gttgggaaaa gtcatttaga gagatattat tgatattagg    3780
gatctaaaat gacttatcgt attacagaga tacgattttg gattttttgac ccactagtta    3840 tcagctcagt tcctatcttc ggggacatac acactttcac agataattgt gtatatatgt    3900
aactgaaaac gatagtgtta acatgaaata atgtacatgt ttgggattaa atgtgttttg    3960
tggatttggt ttgcatcttt tgattttaga ttttggtata ttgtcggtgt ttacatatgc    4020
acattgttaa tatcaacagt atagttgttt ataataagtt atttattgga atgtgtttat    4080
attatgaagc atgaaggaag tcctagagag gcataacttg cagtcaaaga acttggagaa    4140
gcttgatcag ccatctcttg agttacaggt tagctacatt ctcgaaacga ccacacattt    4200
tctttcccga tttctgtaac ttgcaaaatc gagtattact ccgttgaatt accaatatgt    4260
tttagattgt tgtatttatt gaccaagaat ctcttaaaac tttgtattaa taggtacaaa    4320 acttatatatt attgcatatg attaattaga ctcgatccat gtagtagtca tgtagagtag    4380
tcctgtgtag agagttgagc tttagatcat tatggatatg attaagagct taaatcaatg    4440
ttttattctg ttagctggtt gagaacagtg atcacgcccg aatgagtaaa gaaattgcgg    4500
acaagagcca ccgactaagg tacgttatat atgtatattc tatgacttt gaactaacta    4560 tcatttccta actaattttt tttttgatca accactatca ttttctaact gtgtgtttac    4620 atgatccatat ataggcaaat gagaggagag gaacttcaag gacttgacat tgaagagctt    4680
cagcagctag agaaggccct tgaaactggt ttgacgcgtg tgattgaaac aaaggttgtt    4740
aagaaaatta cttgatacca tgtataagtt tctctaagct tacgagtatg caatttacta    4800
atacgagatg tgtttgcaga gtgacaagat tatgagtgag atcagcgaac ttcagaaaaa    4860
```

-continued

| | |
|---|---|
| ggtaataatt aaccaaaata acgtttattc tttacttgat gatttcaata ttaattttgg | 4920 |
| cagtttcaag atccaaaatt ttcatcttct tctcttttt tttggtgttc agggaatgca | 4980 |
| attgatggat gagaacaagc ggttgaggca gcaagtatgt gtcttaccct ctctgttgat | 5040 |
| aacaaatccc tttcttttgt ctaccattaa cgtacacacc cctaaattta atccccagtt | 5100 |
| gtctacaaca catatgtttg atcatactgt gaga | 5134 |

<210> SEQ ID NO 47
<211> LENGTH: 5483
<212> TYPE: DNA
<213> ORGANISM: Arabidopsis thaliana
<220> FEATURE:
<223> OTHER INFORMATION: AGL24 genomic sequence

<400> SEQUENCE: 47

| | |
|---|---|
| agacttacaa taacttcatc aagcaactca tacgagca caaagttttt cctgaatgaa | 60 |
| tcttcattca gaacaccaag ataatcctta ataacacgag caatcctttg tagaagctcc | 120 |
| aaaacaagag agggtgacac gttaactctc gttgtcgcaa caaatatag accaacaacc | 180 |
| ttgacatgga agtagttcac gccatcgaca ttctataagc acaaaaaata agttagatga | 240 |
| aatcattaca gctcacaacc aaacagaaag tataatacct acaaagatag gtggcgcctc | 300 |
| tgcattgcca tcctccttcc agaacttgac tttacggaag aatgtctctg tacttccttt | 360 |
| gggtacctca gcccggtctg tagcaataaa acgttacaca tcttgaaact tgtattggat | 420 |
| ccaaccaaat cgtataatct caaacaaat agctttcttc tactacatta catacagata | 480 |
| ctctgcccaa actaattgaa tagttttgct atatttgtac aatctgattt ggaaattcag | 540 |
| ctcaacataa tttgtcatcg ataagaaat gttggtagat caaacagatc aatgagctta | 600 |
| gagaagattt caatggaaaa ttctcatgaa acagtgacat aagactcgac tctgaagaga | 660 |
| aaaagcaaaa caggaagaag cagagaggat cagatcgaga aagagagctt acagtcacgg | 720 |
| aagacgatgt tatctcctcg ctgagataag acgaagaatt gggagatcat catcgttcct | 780 |
| tatagcggtg gattccgact gtttcaccgc gagtttggtt aagtctactg atcgccgatc | 840 |
| ggtctcgtct ttttgtgtgt ctggtggtga ggtggttcac gtttaccat tgccgtcgt | 900 |
| tatcgtgaag cttcttcatg agacggaggg ttctgtgttt ttgtgaatta tgatttcttg | 960 |
| ttcttatatg ggcctatttt taagacatca atatggccca aatttcgaac ttgttatgag | 1020 |
| tttaaggaaa taagtagtaa gtactataaa tgatggttcg atctcggagg agaaaaaaaa | 1080 |
| aaacattgtt tacgaggaag caaaatgtga gttgatataa agggtacaac acataattta | 1140 |
| tttttggaag tcaaaacttt gaggattaag ctgacaacga aggttagtga agactttcgg | 1200 |
| gatcgagcaa tcgggagata tacatgagcc tagagggctg acaagatgac caagcattcc | 1260 |
| aaatgaaagg cttaagattt ttctttttct aaactcaagt aagaaacaca agatatatga | 1320 |
| aagggtaaca agggtcaaca acaagtctaa gcttttaaa cgtgttagat gattcttctt | 1380 |
| gaacactatt acaattactg tttagtttca catttatatg accttgggag tcttctagct | 1440 |
| cgtcccaaat atattttcaa catattacta taagatccta aagaccaata acattgatct | 1500 |
| acaccaaaaa ctctcacttt ctgattttgc actcgctttt tttcctccca taaacaaaac | 1560 |
| caaaggctta caatactaaa tctgtctcac attcttagtg cttatttgtt ttagtcataa | 1620 |
| agaacttaat cttatacaga ttgaagtctt aaagtcatct atattacttt tcacatgtat | 1680 |
| cattatgaga tggtacgttt cccacgaatt ttatcagttt agtttaattt tcagttgtac | 1740 |

```
tttgggagaa aaaatttaca agatacttgt cggccatgat atcaccctag agttaccgga    1800
gtccggtgat atatcatttc taattagggt taaaacttaa aagggtataa atggctgatc    1860
aaacccaaaa ataaaagata atgatgacgg tgggagacga gtgatcttat caggtgtcgc    1920
atctagcata tataggtgaa agactataaa aaagacatga atatttaat agacacaact     1980 tttgtaataa accaaaacca aaaggtaga tgaactgatg aacagcatct tctaattacg     2040
aataaaaaaa gtaaccaaac tttctttcca ttagaattgg tacgtagttc cttgtgtatt    2100
gtgatttctt tcattttcca attatgtttt tttattttat catgttacat ttttgatagt    2160
gggtaacttt tgtatcattt tatttgacct agccatatat aaatctatta acttatacgg    2220
agtagtattt cacgtcattt atttttattt tgttttaga tgggaagtta ttcaaaacta     2280
gactaaaaca gtaaaactag gaaacccgct actgaataaa gttacaattc cacattattc    2340
catgacagac taattgaatt agaaggttag gtaaattatt aaatcataac tgtagcagtc    2400
tcttcgtctg gcagctcagt cagacaaaac acaaagtgtg tttatgtgtt attttttaatg   2460 attatagttt gggaaaaaga cataatcaaa agggatacaa acatatggc ccattgataa     2520 gtatagatca ctgtttagct aaaaaaagca gactctttt tccaatcttg aacacaaaca     2580
cagtcaccat ctctctctct cttctctct cactcacaca ttagggagta aacagctacc     2640
agaaaaacct tttttatctt ctcacaaatt taataaagtg ggtgctgaga ttgaataacg    2700
taatccaaga tcctccaact cacagaaagg taaaagctgt gaatctgtgt tctttcttct    2760
taagcaaagt gtttgatgaa ttcatctagt cctgtccatt cttttgcttc tcatggttta    2820
tggatctgat ctctctttct ctctctctct agccattagg gtttcctaag aatattatat    2880
aaactctctt tagctaacac cgttccaatt ggtttctttc tttgttcttg gtctaaaatc    2940
taaatggtgt tatgggtata ggcagattca agaacagtag tgaaggagag atctggtaaa    3000
atggcgagag agaagataag gataaagaag attgataaca taacagcgag acaagttact    3060
ttctcaaaga gaagaagagg aatcttcaag aaagccgatg aactttcagt tctttgcgat    3120
gctgatgttg ctctcatcat cttctctgcc accggaaagc tcttcgagtt ctccagctca    3180
aggtatattc tatcttttg ttagtagttg tcttattttt ttcaatccat gtttgtgttt     3240
ttgagaatat ggttggataa atatattaag atatgtattt aaatgagatt tttattttct    3300
cgtttactct ctaaagttaa ttatcagtag gctcggagat ctcatgtacg gcataatttg    3360
atgacctaaa ttattatact ttaaagtata ggattgatgt tttattactt ttatgtataa    3420
cacatcatgt atttaattcc gtttaacata atatggtttt ttaacgtgta attttcaat    3480 cattttcatt tagactcatg gttaagattt ctgtactggg aaataagaga gcagaatatt    3540
atagtgtgat ttttgttaat taggaaagca tatgtatata tggatacata gtacttacca    3600
caattagaat gaatttcttt tcccttttt catttgactt tgtgtattac aaaagtctt     3660 gacactgtca cttggtatga ttggggatta attcttaacc actcgtttag tttatcttgg    3720
gaagcattac cataattggg aaacgagtca tctgtctgta tcgtgatggc tacttctgat    3780 tactttctt ttattataac caaaaggct tctaatgtac ttaattaatt ttacaaatgt      3840
aatatggacg aaggaaatgt ttataagaaa gatggattgt tgttgaaac gtgtagaatg     3900 agagacatat tgggaaggta tagtcttcat gcaagtaaca tcaacaaatt gatggatcca    3960
ccttctactc atctccgggt attttcgata tcacttactc tttttttttt ttgtggattt    4020
taaactctct gctctttta ccaaacccctt ctcttttat caaacccttc tctctataat     4080
attatccgat gttcactttg ttacacgtgt ttgttataat ttttagctgt aagtctaaat    4140
```

-continued

```
atagaaacat tgagtggcat ataatcatta atcttgaagc atctaattaa ttggttttac    4200
atattaatag cagaatcctg aaactgttga ctttgcatct agcagcttga gaattgtaac    4260
ctctccagac taagtaagga agtcgaagac aaaaccaagc agctacggta tggctccatt    4320
gatatgttat gcagataaac ctatttcat ataggctata gctgtaagag atcatctatt    4380
tcatgtgtgt ggtttttttt tttatgtttt ttcaatgatg tgtgcatgct attttaggt    4440 tttagaatct atttcatgga aattgaagat atttcatttc acgtgtaagt tcgtcaagtt    4500
gtggcgtgtg tcttggaaat tgatgttttg tttgtagatt ttaagagcta cttctaaaat    4560
ttacaagagt tttgtaattt tcaattatgg cccattattc tcattaattc attaaaaaaa    4620
ttatatacat tactatctat atctagcata ggtagttttt tttttctttt tctttggtag    4680
acctactgaa caaatatctg atatatcact gactggataa atatctatag agatattttt    4740
gatagaaatg agtgttaatt taacgtaaaa caggaaactg agaggagagg atcttgatgg    4800
attgaactta gaagagttgc agcggctgga gaaactactt gaatccggac ttagccgtgt    4860
gtctgaaaag aaggtttact actatacata aactaatagc atgcatattt tccttaacgt    4920
ggcatataaa taataagctg tacatatata aaagtttgac tttgttgttg ttattggtaa    4980 ataggcgag tgtgtgatga gccaaatttt ctcacttgag aaacgggtta gtagttagta    5040
catacaattc gtataactaa tggatcataa gcctatctat agctagtgac tttcttaata    5100
agtgaaacag ggatcggaat tggtggatga aataagaga ctgagggata aagtacggct    5160 ctaaacccctt atagatatca tggaataacc ttaatctatt ttttatgta taagaaaata    5220 tgatgaggga acgtatatta tatatcggca gctagagacg ttggaaaggg caaaactgac    5280
gacgcttaaa gaggctttgg agacagagtc ggtgaccaca aatgtgtcaa gctacgacag    5340
tggaactccc cttgaggatg actccgacac ttccctgaag cttgggtata atttgtttaa    5400
ctgaacatat ttcaaacttt ttgttgacat tttgtatgtg gatgtttact aactgtttgt    5460
tggttaggct tccatcttgg gaa                                            5483
```

<210> SEQ ID NO 48
<211> LENGTH: 7200
<212> TYPE: DNA
<213> ORGANISM: Arabidopsis thaliana
<220> FEATURE:
<223> OTHER INFORMATION: AGL27 genomic sequence

<400> SEQUENCE: 48

```
caaccagcag caccagctgc aatcaaatcc tttacggttc tttgaatgtt tagcgcattt      60
cctccaccgg tatcttgaaa agatcaaaag aaacctatga agagaactat aaccaagcaa     120
atccactatt ttcaaaaagc tatgaagaga actataagca agcaagcgac tctaaccaag     180
aaagattgat actttcaatc tttggtaaag aatcaacgac tcaatgtttt taaatgtttt     240
ttttcctttt ttggttttag ttaagcttct tgcattcttt aatgatgtct ttattatact     300
atcaaaattt tgcaacttta ccagcatctg caatgatggg tatattagga gctgacgcac     360
acaccgacct tgccgtcgca gccatctccg tggtctaaa acgacgaaag aacacaaata     420
aaacgaaagc atacaaacaa aaaattacta agaaagaaa aaaaaaagg tggcgcacgt     480 tagcaaaccg aaatcgggtt ttcccaggag agaagcggat aaggcgtaac cggatataaa     540
accagcggag aatccggttt gctgcacaat agccgcggat aaggcatcgt agcatccagg     600
cataagcaca atgccttgtt cttcaatcag gcgatgaaaa cgtgtttgga ttctcgctgt     660
```

```
cggattcacc aatctcgccg cgcgtgggtt ccgtcggaat gttggtgaag ctgtaaggtt    720
taagctgcta caacagagtg aagttgtttt gacagccatt aacatcgaca ttcttcgaag    780
cctcgaacaa gttttttctt ctctctaatc gagttagact ctgacccaca cgcttgggat    840
tttaatagag agcacgtggt tattatatct cggtcttatc ttatggtaac agtatctcaa    900
agactcaaac cacaaggtat tgtgaaaatg ttagaggcaa tctaacaata aatgtataat    960
ttggttagct taagctcatc atagaaatgg gcctttatgt caccaaacct atttcacaac   1020
ataacacaag agcccacaaa acaacgactc ctttctccac cagaacaagc acgacaaagg   1080
caagagagtt gcaaaagacc tataagatga taacaatcga aaagatgtaa attttgagaa   1140
aaatcaaaat aaacaagaaa gatttcattg ttttttcactt tttctccatt tctactttga   1200
ttttacatac tctatgggcc aaccaatttc caacctaatg cttgataaaa aatgattcgg   1260
ttttactatc tcaacaaatt gggcctacaa catccaattt catgtagtga cttgttttg    1320 ccttttcac atctcaacaa attgggtcgt ttgtatttaa gaaattgtta cagctttta    1380 gactgaattt tactttatgg ctttatgctc tcttttccg ttttgattaa gggtgaatat    1440
gtaaactgtt gataccatct gatttttttt attttttatt tttcttgtgt gcaactatac   1500
catctgaatt caattgacat tttagccaaa taaaaagat tggtccactt ggatggctgt    1560 aaaaagttt agtggaagta tttataggc ttgttggcaa tcttcaccaa cggctataat     1620
gttgatcttt ttaaaattaa acttaccgtt cgactgtctt ctcaacgatt tgacaattag   1680
ccgttagatt agtattactg atttattatt aacaaaccca tttctttct tatttttgaa   1740 taagctaaat caggccaata aaagggacaa gtagagatgg gctatttctt tttttctctt   1800 ttttttttc ttatgtagta gagaaaagcc tttattctta gagctatcat ttaccaccca    1860
ttaaccagaa gctgagaaat gaagcaagcc gaaacgaatt tgtagttttg gacggtgaaa   1920
ttatatcggg cctttaatgg gcatgtgaat agagttgaga gtcttttttgc cccaaaataat   1980 cgtttaaggg agtattggct cgttggttta atattgggcc gaaacgagat tgggaagaag   2040
aacaatgtcg gtttaatccg gttagggtcg tgggctgatt ctggttcacc tttatagcgt   2100
aagcgaacaa acattgaaaa tggggaagcc aaattagtta ccatccctaa ctcagttttg   2160
agacgtagta tgaatgagcc acggcagaac ctacgaccta actcgataaa gtaatggtta   2220
ctcttggaga cggaagaaag cacaaagatt ttgataaggc tttctagttg gtgaaatggt   2280
caaaatcgct cggagagcca tcataggagc ggggaggtgc tatctgaata tcccaatgca   2340
tcaagacaag atggattcag aaaacaaaga aattaaacaa acattttaaa atatgctctt   2400
agttttagat aatataatgt tttcaatacc aattatctta cactgatagt ggtcaagtta   2460
ctaatcactt ttaataaatt ggtgatagtc aaacgtattg aaaattatcg atttaaaaat   2520
atttgaattc aaaccatttt tagtgaaagt ttgcattgta gttttgatta tccgatcaat   2580
ctttaatata attacgtcaa taataactga atccttgaa ttaaccgtta cccgattcat    2640
aagcactact ttccgatcaa aaccaatgag ataaaataac ttttaaaccc tccaaataaa   2700
aagagaaaac cttaaaaacc aatttctgtt cggtggggat gatgatcgga ctcggaccgg   2760
tctaaccgac tggattaaaa agtctttaac aacgacaagc ttaaaaattt gcctcttagt   2820
ggcttcaaaa cgcaatcgtt tcgcttaata ctattatttt ctctatctcg tttaaccaaa   2880
aaaaaaaacg agttggagga aaaaaaaaac caagaaaaaa gaataaaaag caaaaagcat   2940
tgagcgtctc cggagattag gattaaatta gggcataacc cttatcggag atttgaagcc   3000
atgggaagaa gaaaaatcga gatcaagcga atcgagaaca aaagcagtcg acaagtcact   3060
```

-continued

```
ttctccaaac gacgcaatgg tctcatcgac aaagctcgac aactttcgat tctctgtgaa    3120
tcctccgtcg ctgttgtcgt cgtatctgcc tccggaaaac tctatgactc ttcctccggt    3180
gacgagtaag aagatacttt ccttttctgg gtctcactcg attttgtgc ttttttactt    3240
tgtttaatta ctttctccat atagaagctt caaatctagg gcttttgat tccatcaaat    3300
caactgagat tttctccttg ttttctgtat gaagatagca gatgcgtaag ctttaaccta    3360
atttaagact aaacattttg atcgccaaga tatgttcttg atgttcgttt cgtgtttttt    3420
ttttcgtgtt tttttttttt tcattttaaa atcattttta tctctttttt taccttcatt    3480
tgtgacgaaa tttaatattg catgttattc aagaaacttt tctacacgtg gtgattcgtt    3540
cttgatgttg tttaagtaat ctttgtattg ctagttccat ctgttgttca ctttgaagct    3600
tcgttttttc atataagaaa caatatgttt agattgttca aattttgaga tttggtaatt    3660
atattcaata ttgcaatgca cttcaagtag ttttgttgag agattatttg gggttagtgg    3720
taacattaat cgaatatctt tggttcaaat tggttaacac attgtacttt atgttgatcc    3780
aaaatgtatt gtagatcttt tcttttgtaa ttctctttaa ggaataaggt ttatctagtt    3840
gattttgatg gtttattgta gtgctgggat aagtttccac attgatactc gccacacatt    3900
cttcattact taactaattg gatatcgatt ttaaccctt taatcgtaat tgttgtgtg    3960
tttatgacac catacaagat acattatgtc ttactgagtg actctttgtt gctctctaag    4020
atgttgtagt ttggatttct ttgctaaaga aactcaaact ataactgatt ttactgctac    4080
catatatatg tcagtggcct agtaggttca ttaagtagaa atcggtcgcc aattttacta    4140
attgggagaa accactagac tacaaccaaa tgttcaatga ctttaatagt cttctgttat    4200
ttgtcgtgga tatttttaac cccatgaact tttgtatcta gaaaaatctc atccacttct    4260
cttttagaat actttgaatg cgactaaaag tgagtttttt ttttctaata gacctaagat    4320
aaaatcatca atggataagt aggaaatgga aaggtaactc ttgtcagtat gtgtatatat    4380
acagctcctt ctcatttcct tgatgttgac tccataaatg cttgatcatg aaagcaaatt    4440
tgttaaattt gtaaccaaca aaatgcacag actatagacg aagtattagg aaccgtatct    4500
atctgtctcc attttacaat agtcaagctc tagttgtagc tagtttcttt atttagttct    4560
tataccttaa caaagtggca ctatgcaaag tgttttagt tgagattagt cgtcttatgc    4620
gtcttactaa ttgttcattt tttcttcttt ttgtgattga tgtaaaatta ctaagtcaca    4680
acttgagatg ttactaaaaa gataagaacg tgtaataact gaagtgaatt tgaagccagt    4740
ctctattcat atcatagcat taatagatca tggacaacac atatatagga ttagagctgt    4800
catgaccttc ccggaaatgc taaatcagtt tcttggttta tccttttgg agtatcatga    4860
tatcatttag ccaaaggttt ttggtttcag tattccgatt cgtttgacgt tatgtgtgaa    4920
agcgtcaata actaaaactt ggattgacta gtcaaaatat aaactgattg cattgaattc    4980
ttgaaaattt tcccttaaaa tgaacatgaa tttcatcaag attttgtctt ttggaaggat    5040
gtgatttata atctatacaa tcatacattt tgcatgatat tagtttttg aagaaccaaa    5100
aatagagctt ctttataaaa ctgatttagc cttgataaga aaagaaggt agataatcga    5160
actcatgggg atgagttaaa aatgtgtgca cttagtttct aaaaccttt gaagtcgaaa    5220
caatgacaat attggctgcg aagttgatat ataacaggat cttaaagttg aaattgtaaa    5280
ttcagatttt aattttagag caccagatga tcagagtttc agatttacat ttgaagtata    5340
aaacattttg aacacatata tctaaagcag taacttcaaa aataggtaa ctaatagtaa    5400
```

-continued

```
cttacattgt ttttttttaat gcttttatac ttactatcat ttttatatat agatgcctgg      5460
ttaagtaaag atgattatca aaactgttg gttagtaaca gaaattgttg caaatgtaac       5520
atattatata agctttcttt cactttggtg cattctctct aaataatggc ctctattgat      5580
gcagtatctg attcttagtt ttgaaatggt ttttgcataa attattgttc taatgcattt     5640
ttgttttatc tccagcattt ccaagatcat tgatcgttat gaaatacaac atgctgatga      5700
acttagagcc ttagtaagta attagctaag aacgtcattc taatattctt ctggatgcgg     5760
tttttggtgt tatgaaggat agaagcgctg ttcaagccgg agaaacctca atgttttgaa     5820
ctcgtaacac cgaacttaat tctctagagt tacagttatt gtgtctactg gaaaatacaa    5880
gaacttcaca atctttctga ccattccttt tcttcatgtg caggatcttg aagaaaaaat    5940
tcagaattat cttccacaca aggagttact agaaacagtc caaaggttag cagtacgaca     6000 cattttctc ccctcttctt ctgataaaaa aaatgttttt tttcttttgt ctacttgtga     6060
atacagcaag cttgaagaac caaatgtcga taatgtaagt gtagattctc taatttctct    6120
ggaggaacaa cttgagactg ctctgtccgt aagtagagct aggaaggtat atgtgctgct     6180
actaagtgat tcaaccaatt actccacaaa accttctttt tagttagtta tcctagaaca    6240
atcttttgac ataaatctta atgtcttgtt ataggcagaa ctgatgatgg agtatatcga    6300
gtcccttaaa gaaaaggtta gtgctttggt ttttattttc gataaaggcc atattctagg     6360
ctatgatgat tcttgaattc tattaacctg ctgagtctac agattactat atatatat    6420 atatatcttt tggtcttgtc ttagttcctg atttagtatt ggcttcattc aggtgaaacc    6480
ctaatgagaa ttaaaaaaac aagcagtttt aaactcttga tcaaatccaa cctttccctc    6540
ataaagtgtc gaatttggat gaggatgatt tatgtttcga gaaggaaaca tgtttggaaa   6600
tagctataga agttgttaga aactaatgac cttatgatct tttccaaaca ggagaaattg    6660
ctgagagaag agaaccaggt tctggctagc caggtaacaa tgaccacaat atcttctgct    6720
cttgaagcta attaatcact ttatacgtcc ccgttataga gagatacaca tatacacgta    6780
catgaaaact aaaagttgaa ggactttgat ggatactaga caattatagt gaaaccctaa    6840
atatgtgata agtgataaca aaatgctttt aaaatctatc tttcttgtta atttagtagc    6900
tgtcagagaa gaaaggtatg tctcaccgat gaaagatact caaaacccgg tatttttaat    6960
ttgtgaaatt tgcaaataaa aaaaatgctt tctacaagat agattaattt cttgcaatgt    7020
ttagtagctg tagaaaaaaa agaaatgtaa gaaagtttct tacagatggg aaagaatacg    7080
ttgctggcaa cagatgatga gagaggaatg tttccgggaa gtagctccgg caacaaaata    7140
ccggagactc tcccgctgct caattagcca ccatcatcaa cggctgagtt ttcaccttaa    7200
```

<210> SEQ ID NO 49
<211> LENGTH: 579
<212> TYPE: DNA
<213> ORGANISM: Arabidopsis thaliana
<220> FEATURE:
<221> NAME/KEY: CDS
<222> LOCATION: (1)..(579)
<223> OTHER INFORMATION: alternatively spliced AGL27

<400> SEQUENCE: 49

```
atg gga aga aga aaa atc gag atc aag cga atc gag aac aaa agc agt      48
Met Gly Arg Arg Lys Ile Glu Ile Lys Arg Ile Glu Asn Lys Ser Ser
 1               5                  10                  15 cga caa gtc act ttc tcc aaa cga cgc aat ggt ctc atc gac aaa gct      96
Arg Gln Val Thr Phe Ser Lys Arg Arg Asn Gly Leu Ile Asp Lys Ala
            20                  25                  30
```

-continued

| | | |
|---|---|---|
| cga caa ctt tcg att ctc tgt gaa tcc tcc gtc gct gtt gtc gtc gta<br>Arg Gln Leu Ser Ile Leu Cys Glu Ser Ser Val Ala Val Val Val Val<br>    35      40      45 | | 144 |
| tct gcc tcc gga aaa ctc tat gac tct tcc tcc ggt gac gag ata gaa<br>Ser Ala Ser Gly Lys Leu Tyr Asp Ser Ser Ser Gly Asp Glu Ile Glu<br>50      55      60 | | 192 |
| gcg ctg ttc aag ccg gag aaa cct caa tgt ttt gaa ctc gat ctt gaa<br>Ala Leu Phe Lys Pro Glu Lys Pro Gln Cys Phe Glu Leu Asp Leu Glu<br>65      70      75      80 | | 240 |
| gaa aaa att cag aat tat ctt cca cac aag gag tta cta gaa aca gtc<br>Glu Lys Ile Gln Asn Tyr Leu Pro His Lys Glu Leu Leu Glu Thr Val<br>      85      90      95 | | 288 |
| caa agc aag ctt gaa gaa cca aat gtc gat aat gta agt gta gat tct<br>Gln Ser Lys Leu Glu Glu Pro Asn Val Asp Asn Val Ser Val Asp Ser<br>    100      105      110 | | 336 |
| cta att tct ctg gag gaa caa ctt gag act gct ctg tcc gta agt aga<br>Leu Ile Ser Leu Glu Glu Gln Leu Glu Thr Ala Leu Ser Val Ser Arg<br>115      120      125 | | 384 |
| gct agg aag gca gaa ctg atg atg gag tat atc gag tcc ctt aaa gaa<br>Ala Arg Lys Ala Glu Leu Met Met Glu Tyr Ile Glu Ser Leu Lys Glu<br>130      135      140 | | 432 |
| aag gag aaa ttg ctg aga gaa gag aac cag gtt ctg gct agc cag atg<br>Lys Glu Lys Leu Leu Arg Glu Glu Asn Gln Val Leu Ala Ser Gln Met<br>145      150      155      160 | | 480 |
| gga aag aat acg ttg ctg gca aca gat gat gag aga gga atg ttt ccg<br>Gly Lys Asn Thr Leu Leu Ala Thr Asp Asp Glu Arg Gly Met Phe Pro<br>      165      170      175 | | 528 |
| gga agt agc tcc ggc aac aaa ata ccg gag act ctc ccg ctg ctc aat<br>Gly Ser Ser Ser Gly Asn Lys Ile Pro Glu Thr Leu Pro Leu Leu Asn<br>    180      185      190 | | 576 |
| tag | | 579 |

```
<210> SEQ ID NO 50
<211> LENGTH: 192
<212> TYPE: PRT
<213> ORGANISM: Arabidopsis thaliana
<220> FEATURE:
<223> OTHER INFORMATION: alternatively spliced AGL27

<400> SEQUENCE: 50
```

Met Gly Arg Arg Lys Ile Glu Ile Lys Arg Ile Glu Asn Lys Ser Ser
1      5         10        15

Arg Gln Val Thr Phe Ser Lys Arg Arg Asn Gly Leu Ile Asp Lys Ala
      20         25        30

Arg Gln Leu Ser Ile Leu Cys Glu Ser Ser Val Ala Val Val Val Val
    35        40        45

Ser Ala Ser Gly Lys Leu Tyr Asp Ser Ser Ser Gly Asp Glu Ile Glu
50        55        60

Ala Leu Phe Lys Pro Glu Lys Pro Gln Cys Phe Glu Leu Asp Leu Glu
65        70        75        80

Glu Lys Ile Gln Asn Tyr Leu Pro His Lys Glu Leu Leu Glu Thr Val
      85         90        95

Gln Ser Lys Leu Glu Glu Pro Asn Val Asp Asn Val Ser Val Asp Ser
    100        105        110

Leu Ile Ser Leu Glu Glu Gln Leu Glu Thr Ala Leu Ser Val Ser Arg
      115        120        125

Ala Arg Lys Ala Glu Leu Met Met Glu Tyr Ile Glu Ser Leu Lys Glu
130        135        140

```
Lys Glu Lys Leu Leu Arg Glu Glu Asn Gln Val Leu Ala Ser Gln Met
145                 150                 155                 160

Gly Lys Asn Thr Leu Leu Ala Thr Asp Asp Glu Arg Gly Met Phe Pro
                165                 170                 175

Gly Ser Ser Ser Gly Asn Lys Ile Pro Glu Thr Leu Pro Leu Leu Asn
            180                 185                 190
```

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence:PCR oligo
      primer SEP3-5'K

<400> SEQUENCE: 51
ccgtcgaccc atgagccagc aggagtatct c                           31

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence:PCR oligo
      primer SEP3-3'Kbox

<400> SEQUENCE: 52
ccgcggccgc cttactctga agatcgtt                               28

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence:PCR oligo
      primer SOC1-5'K

<400> SEQUENCE: 53
ccgtcgaccc atgaaatatg aagcagcaaa c                           31

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence:PCR oligo
      primer SOC1-3'Kbox

<400> SEQUENCE: 54
ccgcggccgc ctcctttttgc ttgagctg                              28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence:PCR oligo
      primer SOC1-C/2

<400> SEQUENCE: 55
ccgcggccgc actttcttga ttcttatt                               28

<210> SEQ ID NO 56
<211> LENGTH: 31
<212> TYPE: DNA

```
<213> ORGANISM: Artificial Sequence
<220> FEATURE:
<223> OTHER INFORMATION: Description of Artificial Sequence:PCR oligo
      primer SVP-5'K

<400> SEQUENCE: 56
ccgtcgaccc atgagtgatc acgcccgaat g                                    31

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:PCR oligo
      primer SVP-3'Kbox

<400> SEQUENCE: 57
ccgcggccgc tccctttttc tgaagttc                                        28

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence:PCR oligo
      primer AGL24-5'K

<400> SEQUENCE: 58
ccgtcgaccc atgcttgaga attgtaacct c                                    31

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence:PCR oligo
      primer AGL24-3'Kbox

<400> SEQUENCE: 59
ccgcggccgc ctcaagtgag aaaatttg                                        28

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence:RT-PCR oligo
      OAM37

<400> SEQUENCE: 60
tagaaacatc atcttaaaaa t                                               21

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence:RT-PCR oligo
      SEP3-5'

<400> SEQUENCE: 61
ccggatccaa aatgggaaga gggaga                                          26
```